United States Patent
Kim et al.

(10) Patent No.: US 10,084,141 B2
(45) Date of Patent: *Sep. 25, 2018

(54) ANTIAROMATIC COMPOUND AND ORGANIC LIGHT-EMITTING DEVICE INCLUDING THE SAME

(71) Applicants: SAMSUNG DISPLAY CO., LTD., Yongin, Gyeonggi-Do (KR); INDUSTRY-ACADEMIC COOPERATION FOUNDATION GYEONGSANG NATIONAL UNIVERSITY, Gyeongnam (KR)

(72) Inventors: Mikyung Kim, Yongin (KR); Yunhi Kim, Gyeongnam (KR); Soonki Kwon, Gyeongnam (KR); Boram Kim, Gyeongnam (KR); Yongjin Yoon, Gyeongnam (KR)

(73) Assignees: Samsung Display Co., Ltd., Yongin-si (KR); Industry-Academic Cooperation Foundation Gyeongsang National University, Jinju (KR)

( * ) Notice: Subject to any disclaimer, the term of this patent is extended or adjusted under 35 U.S.C. 154(b) by 317 days.

This patent is subject to a terminal disclaimer.

(21) Appl. No.: 14/738,721

(22) Filed: Jun. 12, 2015

(65) Prior Publication Data

US 2015/0364700 A1    Dec. 17, 2015

(30) Foreign Application Priority Data

Jun. 13, 2014  (KR) .................. 10-2014-0072303
Apr. 21, 2015  (KR) .................. 10-2015-0056005

(51) Int. Cl.
*H01L 51/00*    (2006.01)
*C07D 245/04*    (2006.01)
(Continued)

(52) U.S. Cl.
CPC ........ *H01L 51/0072* (2013.01); *C07D 245/04* (2013.01); *C09K 11/06* (2013.01);
(Continued)

(58) Field of Classification Search
None
See application file for complete search history.

(56) References Cited

U.S. PATENT DOCUMENTS 3,409,608 A * 11/1968 Topliss ............... C07D 245/04
                                                540/460
2005/0197337 A1    9/2005 Malherbe et al.
(Continued)

FOREIGN PATENT DOCUMENTS

KR    10-2006-0116240 A    11/2006
KR    10-2009-0059842 A    6/2009
(Continued)

OTHER PUBLICATIONS

Zhao et al. (Tetrahedon, 68, 2012, 9665).*
(Continued)

*Primary Examiner* — Kevin M Bernatz
(74) *Attorney, Agent, or Firm* — Lewis Roca Rothgerber Christie LLP

(57) ABSTRACT

Provided are an antiaromatic compound and an organic light-emitting device including the same. The antiaromatic compound is represented by Formula 1, where the substituents of Formula 1 are described herein. The organic light-emitting device light includes a first electrode, a second electrode, and an organic layer between the first electrode and the second electrode. The organic layer includes the antiaromatic compound represented by Formula 1.

(Continued)

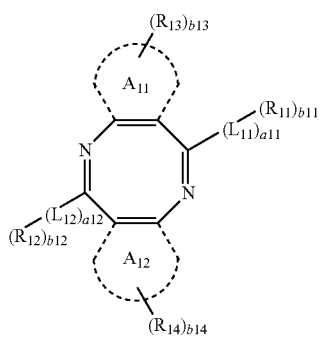

Formula 1

3 Claims, 4 Drawing Sheets

(51) Int. Cl.
  *C09K 11/06* (2006.01)
  *H01L 51/50* (2006.01)
(52) U.S. Cl.
  CPC ...... *H01L 51/0052* (2013.01); *H01L 51/0054* (2013.01); *H01L 51/0058* (2013.01); *C09K 2211/1007* (2013.01); *C09K 2211/1011* (2013.01); *C09K 2211/1044* (2013.01); *H01L 51/006* (2013.01); *H01L 51/0061* (2013.01); *H01L 51/0067* (2013.01); *H01L 51/0077* (2013.01); *H01L 51/5012* (2013.01)

(56) References Cited

U.S. PATENT DOCUMENTS

| | | | |
|---|---|---|---|
| 2006/0058499 A1* | 3/2006 | Lee | C08G 61/12 528/373 |
| 2009/0146554 A1 | 6/2009 | Lee et al. | |
| 2011/0037063 A1 | 2/2011 | Buesing et al. | |
| 2011/0240969 A1 | 10/2011 | Kim et al. | |
| 2012/0126180 A1 | 5/2012 | Parham et al. | |
| 2012/0235123 A1 | 9/2012 | Lee et al. | |
| 2012/0283407 A1* | 11/2012 | Hoppin | C07D 245/04 528/337 |
| 2015/0357578 A1* | 12/2015 | Kim | C07D 401/14 257/40 |

FOREIGN PATENT DOCUMENTS

| | | |
|---|---|---|
| KR | 10-2009-0081478 A | 7/2009 |
| KR | 10-2010-0133485 A | 12/2010 |
| KR | 10-2011-0015836 A | 2/2011 |
| KR | 10-2011-0049244 A | 5/2011 |
| KR | 10-2011-0088118 A | 8/2011 |
| KR | 10-2011-0111103 A | 10/2011 |
| KR | 10-2012-0038530 A | 4/2012 |
| KR | 10-2012-0056418 A | 6/2012 |
| KR | 10-2012-0107996 A | 10/2012 |
| WO | WO 2011/055912 A1 | 5/2011 |
| WO | WO 2011/093609 A1 | 8/2011 |

OTHER PUBLICATIONS

Wang et al. (Org. Let., 13(4), 2011, 709).*
U.S. Office Action dated Mar. 9, 2017, issued in cross-reference U.S. Appl. No. 14/533,028 (11 pages).

* cited by examiner

_US 10,084,141 B2_

ANTIAROMATIC COMPOUND AND ORGANIC LIGHT-EMITTING DEVICE INCLUDING THE SAME

CROSS-REFERENCE TO RELATED APPLICATIONS

This application claims priority to and the benefit of Korean Patent Application No. 10-2014-0072303, filed on Jun. 13, 2014, and Korean Patent Application No. 10-2015-0056005, filed on Apr. 21, 2015, in the Korean Intellectual Property Office, the entire contents of both of which are incorporated herein by reference.

BACKGROUND

1. Field

One or more example embodiments relate to an antiaromatic compound and an organic light-emitting device including the same.

2. Description of the Related Art

Organic light-emitting devices (OLEDs) are self-emitting devices that have wide viewing angles, high contrast ratios, and short response times. OLEDs also exhibit excellent brightness, driving voltage, and response speed characteristics, and produce multicolored images.

The OLED may include a first electrode disposed on a substrate, and a hole transport region, an emission layer, an electron transport region, and a second electrode, which are sequentially disposed on the first electrode. Holes provided from the first electrode move toward the emission layer through the hole transport region, and electrons provided from the second electrode move toward the emission layer through the electron transport region. Carriers, such as holes and electrons, are recombined in the emission layer to produce excitons. These excitons change from an excited state to a ground state, thereby generating light.

SUMMARY

One or more example embodiments include an antiaromatic compound and an organic light-emitting device including the same.

Additional aspects will be set forth in part in the description which follows and, in part, will be apparent from the description, or may be learned by practice of the presented embodiments.

According to an embodiment of the present disclosure, there is provided an antiaromatic compound represented by Formula 1:

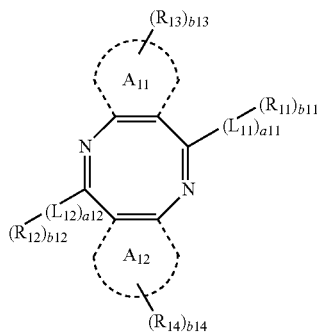

Formula 1

In Formula 1, $A_{11}$ and $A_{12}$ are each independently a $C_6$-$C_{60}$ arene;

$L_{11}$ and $L_{12}$ are each independently selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, a substituted or unsubstituted divalent non-aromatic condensed antiaromatic compound, and a divalent non-aromatic condensed heteropolycyclic group;

a11 and a12 are each independently an integer selected from 0 to 6;

$R_{11}$ and $R_{12}$ are each independently selected from a substituted or unsubstituted $C_6$-$C_{60}$ aryl group, a substituted or unsubstituted monovalent non-aromatic condensed antiaromatic compound, and a monovalent non-aromatic condensed heteropolycyclic group;

b11 and b12 are each independently selected from 1, 2, and 3;

$R_{13}$ and $R_{14}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_1$-$C_{60}$ alkoxy group, a substituted or unsubstituted $C_3$-$C_{10}$ cycloalkyl group, a substituted or unsubstituted $C_6$-$C_{60}$ aryl group, a substituted or unsubstituted $C_6$-$C_{60}$ aryloxy group, a substituted or unsubstituted monovalent non-aromatic condensed antiaromatic compound, and a monovalent non-aromatic condensed heteropolycyclic group;

b13 and b14 are each independently selected from 1, 2, 3, 4, 5, 6, 7, 8, 9, and 10; and at least one substituent of the substituted $C_3$-$C_{10}$ cycloalkylene group, the substituted $C_3$-$C_{10}$ cycloalkenylene group, the substituted $C_6$-$C_{60}$ arylene group, the substituted divalent non-aromatic condensed polycyclic group, the substituted divalent non-aromatic condensed heteropolycyclic group, the substituted $C_1$-$C_{60}$ alkyl group, the substituted $C_1$-$C_{60}$ alkoxy group, the substituted $C_3$-$C_{10}$ cycloalkyl group, the substituted $C_6$-$C_{60}$ aryl group, the substituted monovalent non-aromatic condensed polycyclic group, and the substituted monovalent non-aromatic condensed heteropolycyclic group are selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group;

a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group; and a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group.

According to another embodiment of the present disclosure, there is provided an organic light-emitting device including a first electrode; a second electrode; and an organic layer between the first electrode and the second electrode, wherein the organic layer includes an emission layer and at least one of the antiaromatic compound of Formula 1.

BRIEF DESCRIPTION OF THE DRAWINGS

These and/or other aspects will become apparent and more readily appreciated from the following description of the example embodiments, taken in conjunction with the accompanying drawings in which.

DETAILED DESCRIPTION

Figure 1:
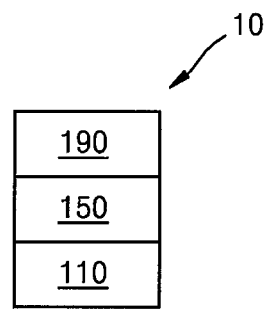
FIG. 1 illustrates a schematic view of an organic light-emitting device according to an embodiment.

Reference will now be made in detail to example embodiments, examples of which are illustrated in the accompanying drawings, wherein like reference numerals refer to like elements throughout. In this regard, the present example embodiments may have different forms and should not be construed as being limited to the descriptions set forth herein. Accordingly, the example embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

As used herein, the singular forms "a," "an" and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

It will be understood that when a layer, region, or component is referred to as being "formed on" another layer, region, or component, it can be directly or indirectly on or formed on the other layer, region, or component. That is, for example, intervening layers, regions, or components may be present.

Sizes of elements in the drawings may be exaggerated for convenience of explanation. In other words, since sizes and thicknesses of components in the drawings may be arbitrarily illustrated for convenience of explanation, the sizes and thicknesses of components are not limited thereto.

As used herein, the term "substantially," "about," and similar terms are used as terms of approximation and not as terms of degree, and are intended to account for the inherent deviations in measured or calculated values that would be recognized by those of ordinary skill in the art. Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. § 112(a), and 35 U.S.C. § 132(a).

There is provided an antiaromatic compound represented by Formula 1:

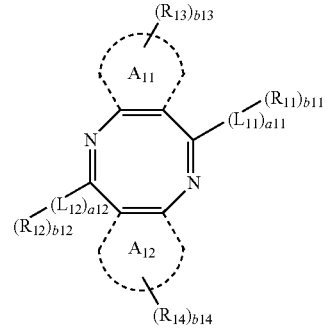

Formula 1

In Formula 1, $A_{11}$ and $A_{12}$ may be each independently a $C_6$-$C_{60}$ arene.

In an example embodiment, $A_{11}$ and $A_{12}$ in Formula 1 may be each independently a $C_6$-$C_{20}$ arene, but $A_{11}$ and $A_{12}$ not limited thereto.

In another example embodiment, $A_{11}$ and $A_{12}$ in Formula 1 may be each independently selected from a benzene, a naphthalene, a phenanthrene, an anthracene, a triphenylene, a pyrene, and a chrysene, but $A_{11}$ and $A_{12}$ not limited thereto.

In another example embodiment, $A_{11}$ and $A_{12}$ in Formula 1 may be each independently selected from a benzene and a naphthalene, but $A_{11}$ and $A_{12}$ are not limited thereto.

In another example embodiment, $A_{11}$ and $A_{12}$ in Formula 1 may be each independently selected from groups represented by Formulae 10-1 to 10-3, but $A_{11}$ and $A_{12}$ are not limited thereto:

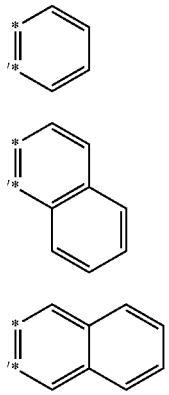

10-1

10-2

10-3

In Formulae 10-1 to 10-3,

* and *' may each be a carbon atom binding to a core of 1,5-diazocine of

Formula 1 (e.g., two carbon atoms of the core of 1,5-diazocine may be shared with the groups of Formulae 10-1 to 10-3).

In Formula 1, $L_{11}$ and $L_{12}$ may be each independently selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, a substituted or unsubstituted divalent non-aromatic condensed antiaromatic compound, and a divalent non-aromatic condensed heteropolycyclic group, at least one substituent of the substituted $C_3$-$C_{10}$ cycloalkylene group, the substituted $C_3$-$C_{10}$ cycloalkenylene group, the substituted $C_6$-$C_{60}$ arylene group, the substituted divalent non-aromatic condensed polycyclic group, and the substituted divalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group;

a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group; and a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group.

In an example embodiment, $L_{11}$ and $L_{12}$ in Formula 1 may be each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a carbazolylene group, a benzocarbazolylene group, a dibenzocarbazolylene group, a dibenzofuranylene group, and a dibenzothiophenylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a carbazolylene group, a benzocarbazolylene group, a dibenzocarbazolylene group, a dibenzofuranylene group, and a dibenzothiophenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a carbazolyl group, a benzocarbazolyl group, and a dibenzocarbazolyl group, but $L_{11}$ and $L_{12}$ are not limited thereto.

In another example embodiment, $L_{11}$ and $L_{12}$ in Formula 1 may be each independently selected from groups represented by Formulae 3-1 to 3-9, but $L_{11}$ and $L_{12}$ are not limited thereto:

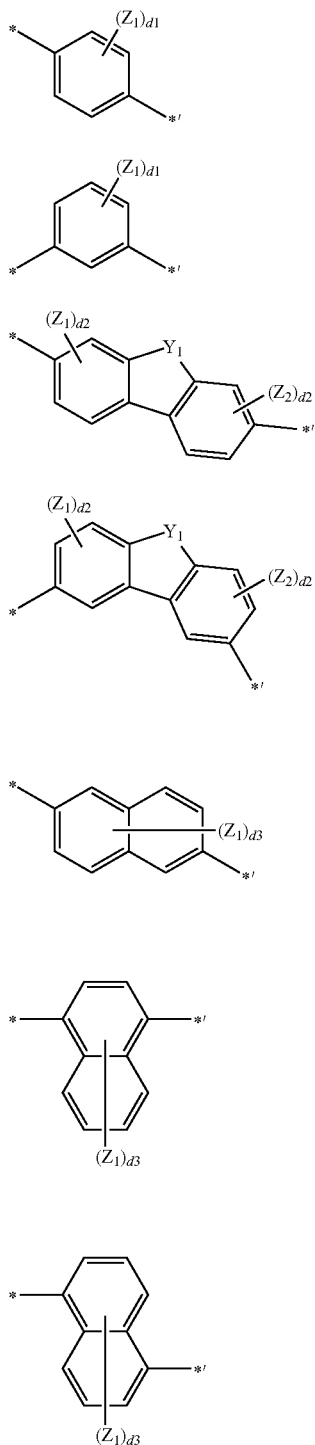

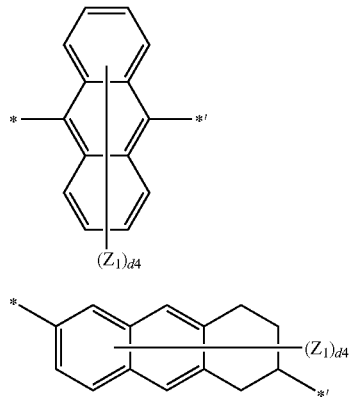

In Formulae 3-1 to 3-9, $Y_1$ may be selected from $C(Z_1)(Z_2)$, $N(Z_1)$, an oxygen atom (O), and a sulfur atom (S);

$Z_1$ and $Z_2$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a carbazolyl group, a benzocarbazolyl group, and a dibenzocarbazolyl group;

d1 may be selected from 1, 2, 3, and 4;

d2 may be selected from 1, 2, and 3;

d3 may be selected from 1, 2, 3, 4, 5, and 6;

d4 may be selected from 1, 2, 3, 4, 5, 6, 7, and 8;

* and *' may each indicate a binding site to a neighboring atom.

In another example embodiment, $L_{11}$ and $L_{12}$ in Formula 1 may be each independently selected from groups represented by Formulae 4-1 to 4-6, but $L_{11}$ and $L_{12}$ are not limited thereto:

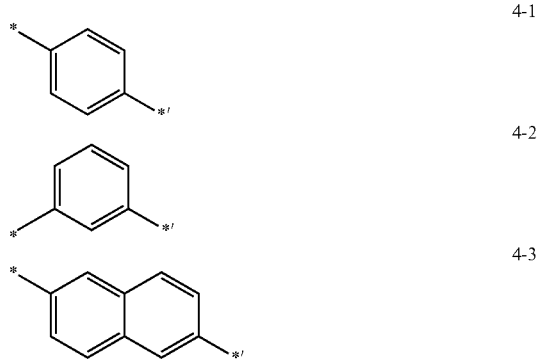

-continued 4-4
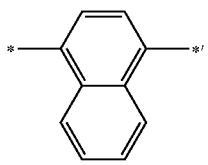

4-5
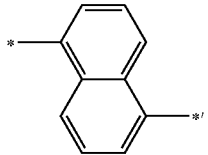

4-6
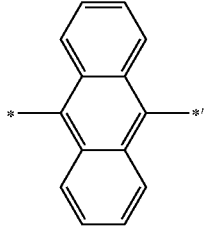

In Formulae 4-1 to 4-6,

* and *' may each indicate a binding site to different atoms from each other.

In Formula 1, a11 indicates the number of $L_{11}$, and may be selected from 0, 1, 2, 3, 4, 5, and 6. When a11 is 0, $(L_{11})_{a11}$ indicates a single bond. When a11 is 2 or more, a plurality of $L_{11}$s may be identical to or different from each other. For example, a11 in Formula 1 may be selected from 0 and 1, but it is not limited thereto.

In Formula 1, a12 indicates the number of $L_{12}$, and may be selected from 0, 1, 2, 3, 4, 5, and 6. When a12 is 0, $(L_{12})_{a12}$ indicates a single bond. When a12 is 2 or more, a plurality of $L_{12}$s may be identical to or different from each other. For example, a12 in Formula 1 may be selected from 0 and 1, but it is not limited thereto.

In an example embodiment, $(L_{11})_{a11}$ and $(L_{12})_{a12}$ in Formula 1 may be each independently selected from a single bond and groups represented by Formulae 4-21 to 4-28, but $(L_{11})_{a11}$ and $(L_{12})_{a12}$ are not limited thereto:

4-21
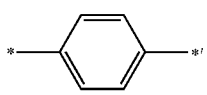

4-22
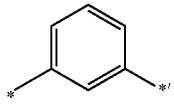

4-23
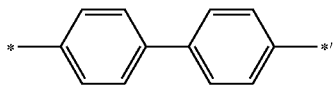

4-24
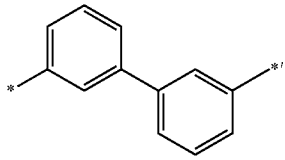

4-25
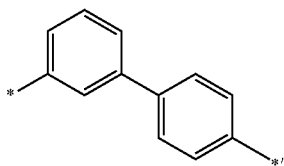

4-26
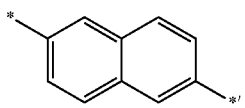

4-27
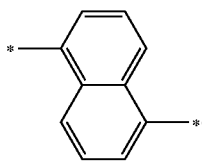

4-28
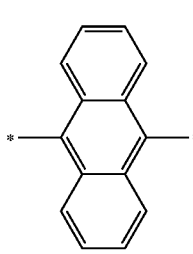

In Formulae 4-21 to 4-28,

* and *' may each indicate a binding site to a neighboring atom.

In Formula 1, $R_{11}$ and $R_{12}$ may be each independently selected from a substituted or unsubstituted $C_6$-$C_{60}$ aryl group, a substituted or unsubstituted monovalent non-aromatic condensed antiaromatic compound, and a monovalent non-aromatic condensed heteropolycyclic group; and at least one substituent of the substituted $C_6$-$C_{60}$ aryl group, the substituted monovalent non-aromatic condensed polycyclic group, and the substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group;

a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group; and a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group.

In an example embodiment, $R_{11}$ and $R_{12}$ in Formula 1 may be each independently selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a carbazolyl group, a benzocarbazolyl group, a dibenzocarbazolyl group, a dibenzofuranyl group, and a dibenzothiophenyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a carbazolyl group, a benzocarbazolyl group, a dibenzocarbazolyl group, a dibenzofuranyl group, and a dibenzothiophenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a carbazolyl group, a benzocarbazolyl group, and a dibenzocarbazolyl group, but $R_{11}$ and $R_{12}$ are not limited thereto.

In another example embodiment, $R_{11}$ and $R_{12}$ in Formula 1 may be each independently selected from a phenyl group, a naphthyl group, an anthracenyl group, a triphenylenyl group, a phenanthrenyl group, a pyrenyl group, a fluorenyl group, and a carbazolyl group; and a phenyl group, a naphthyl group, an anthracenyl group, a triphenylenyl group, a phenanthrenyl group, a pyrenyl group, a fluorenyl group, and a carbazolyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a carbazolyl group, a benzocarbazolyl group, and a dibenzocarbazolyl group, but $R_{11}$ and $R_{12}$ are not limited thereto.

In another example embodiment, $R_{11}$ and $R_{12}$ in Formula 1 may be each independently selected from groups represented by Formulae 5-1 to 5-29, but $R_{11}$ and $R_{12}$ are not limited thereto:

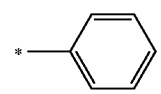

5-1

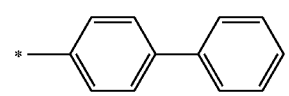

5-2

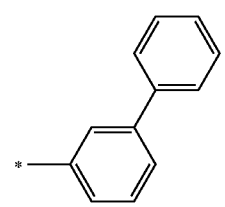

5-3

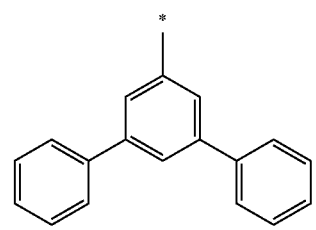

5-4

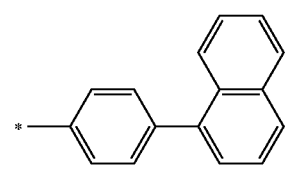

5-5

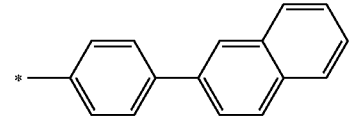

5-6

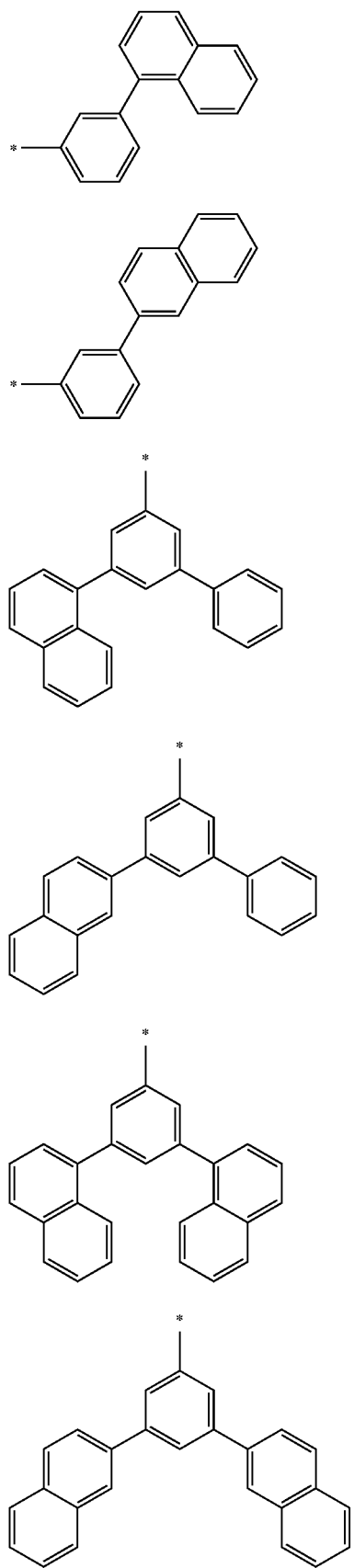
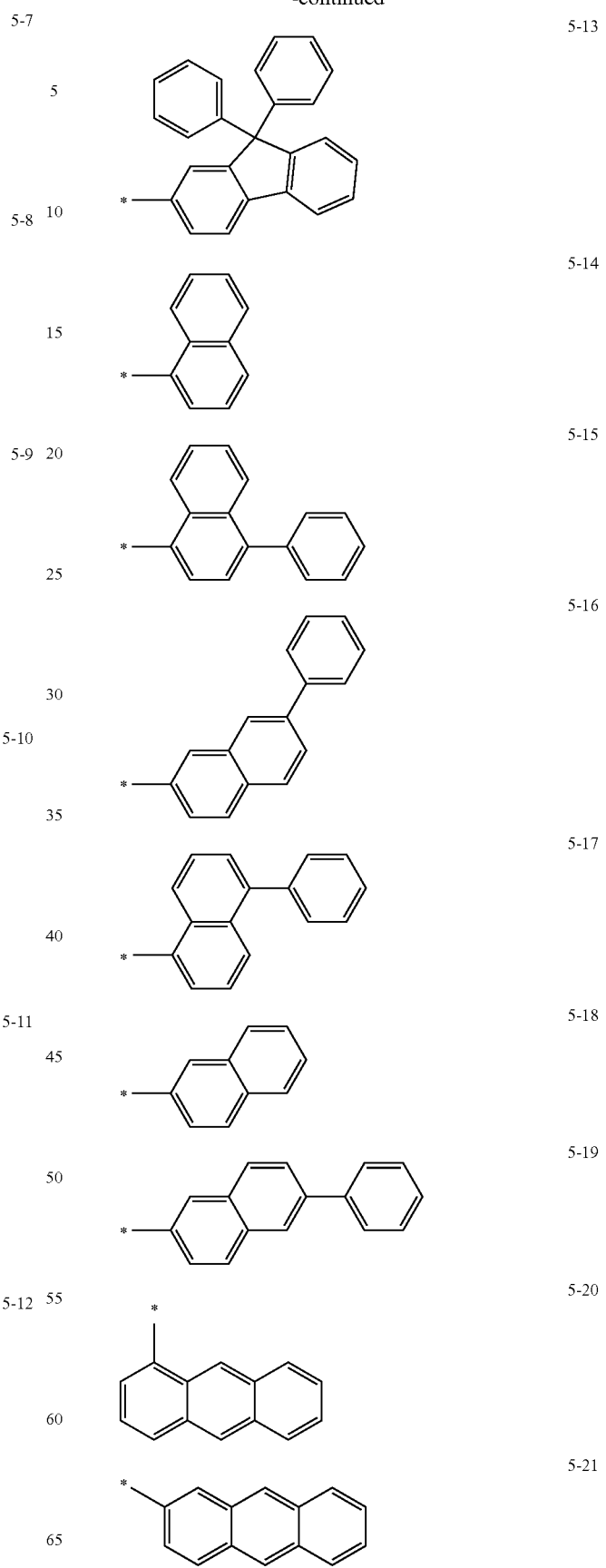

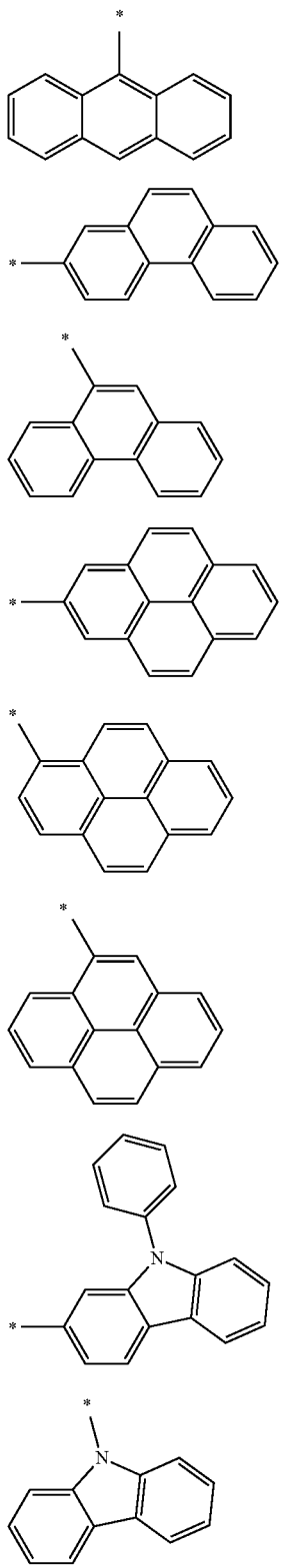

In Formulae 5-1 to 5-29,

* may indicate a binding site to a neighboring atom.

In Formula 1, b11 indicates the number of $R_{11}$, and may be selected from 1, 2, and 3. When b11 is 2 or more, a plurality of $R_{11}$s may be identical to or different from each other. For example, b11 in Formula 1 may be 1, but it is not limited thereto.

In Formula 1, b12 indicates the number of $R_{12}$, and may be selected from 1, 2, and 3. When b12 is 2 or more, a plurality of $R_{12}$s may be identical to or different from each other. For example, b12 in Formula 1 may be 1, but it is not limited thereto.

In an example embodiment, $R_{13}$ and $R_{14}$ in Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_1$-$C_{60}$ alkoxy group, a substituted or unsubstituted $C_3$-$C_{10}$ cycloalkyl group, a substituted or unsubstituted $C_6$-$C_{60}$ aryl group, a substituted or unsubstituted $C_6$-$C_{60}$ aryloxy group, a substituted or unsubstituted monovalent non-aromatic condensed antiaromatic compound, and a monovalent non-aromatic condensed heteropolycyclic group; and at least one substituent of the substituted $C_1$-$C_{60}$ alkyl group, the substituted $C_1$-$C_{60}$ alkoxy group, the substituted $C_3$-$C_{10}$ cycloalkyl group, the substituted $C_6$-$C_{60}$ aryl group, the substituted $C_6$-$C_{60}$ aryloxy group, the substituted monovalent non-aromatic condensed polycyclic group, and the substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group;

a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group; and a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group.

In another example embodiment, $R_{13}$ and $R_{14}$ in Formula 1 may be each independently selected from a hydrogen, a deuterium, —F, —Cl, —Br, —I, $C_1$-$C_{60}$ alkyl group, a $C_6$-$C_{60}$ aryl group, a monovalent non-aromatic condensed polycyclic group, and a monovalent non-aromatic condensed heteropolycyclic group, but $R_{13}$ and $R_{14}$ are not limited thereto.

In another example embodiment, $R_{13}$ and $R_{14}$ in Formula 1 may be each independently selected from a hydrogen, a deuterium, —F, —Cl, —Br, —I, a methyl group, an ethyl group, an n-propyl group, an iso-propyl group, an n-butyl group, iso-butyl group, a sec-butyl group, a tert-butyl group, a phenyl group, and a naphthyl group, but $R_{13}$ and $R_{14}$ are not limited thereto.

In Formula 1, b13 indicates the number of $R_{13}$, and may be selected from 1, 2, 3, 4, 5, 6, 7, 8, 9, and 10. When b13 is 2 or more, a plurality of $R_{13}$s may be identical to or different from each other.

In Formula 1, b14 indicates the number of $R_{14}$, and may be selected from 1, 2, 3, 4, 5, 6, 7, 8, 9, and 10. When b14 is 2 or more, a plurality of $R_{14}$s may be identical to or different from each other.

In an example embodiment, the antiaromatic compound of Formula 1 may be represented by one of Formulae 1A to 1D, but it is not limited thereto:

Formula 1A

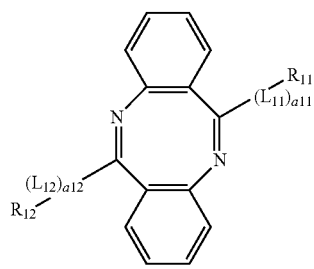

Formula 1B

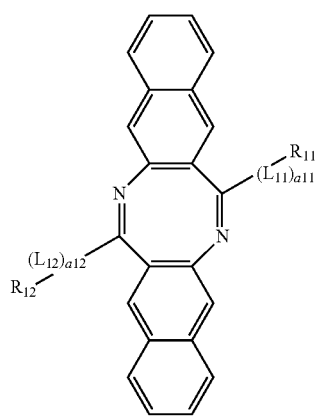

Formula 1C

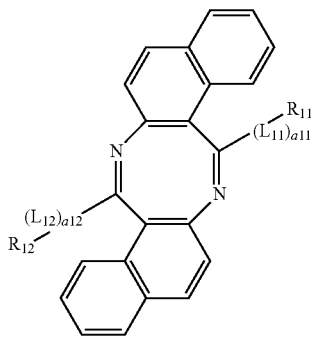

Formula 1D

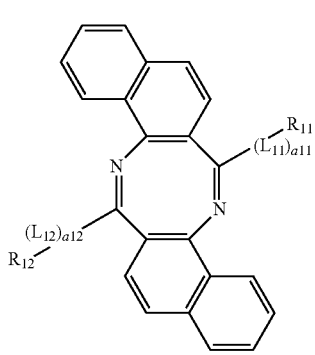

In Formulae 1A to 1D, descriptions of $L_{11}$, $L_{12}$, a11, a12, $R_{11}$, and $R_{12}$ may be each independently as referred to in the descriptions provided in connection with Formula 1.

In another example embodiment, the antiaromatic compound of Formula 1 may be represented by one of Formulae 1A to 1D, but it is not limited thereto:

Formula 1A

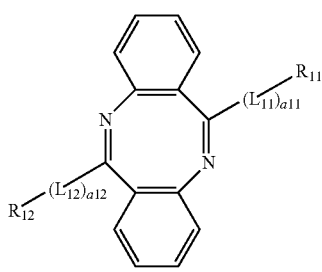

Formula 1B

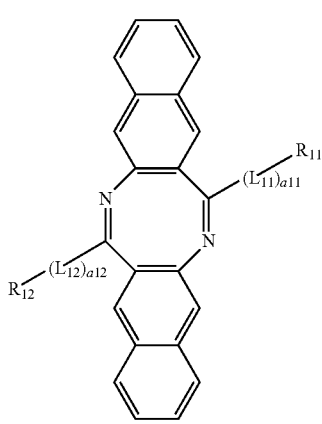

Formula 1C
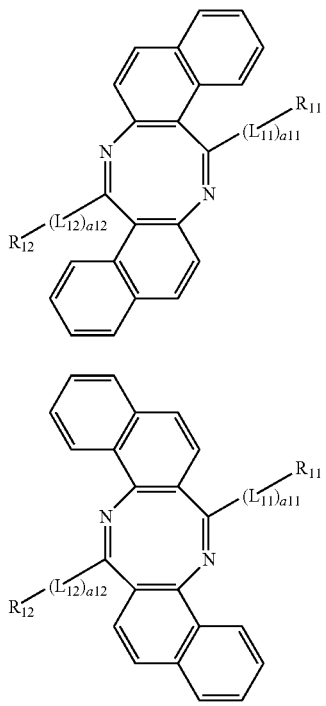
Formula 1D
wherein, in Formulae 1A to 1D,
$(L_{11})_{a11}$ and $(L_{12})_{a12}$ may be each independently selected from a single bond and groups represented by Formulae 4-21 to 4-28 and Formulae 5-1 to 5-29:
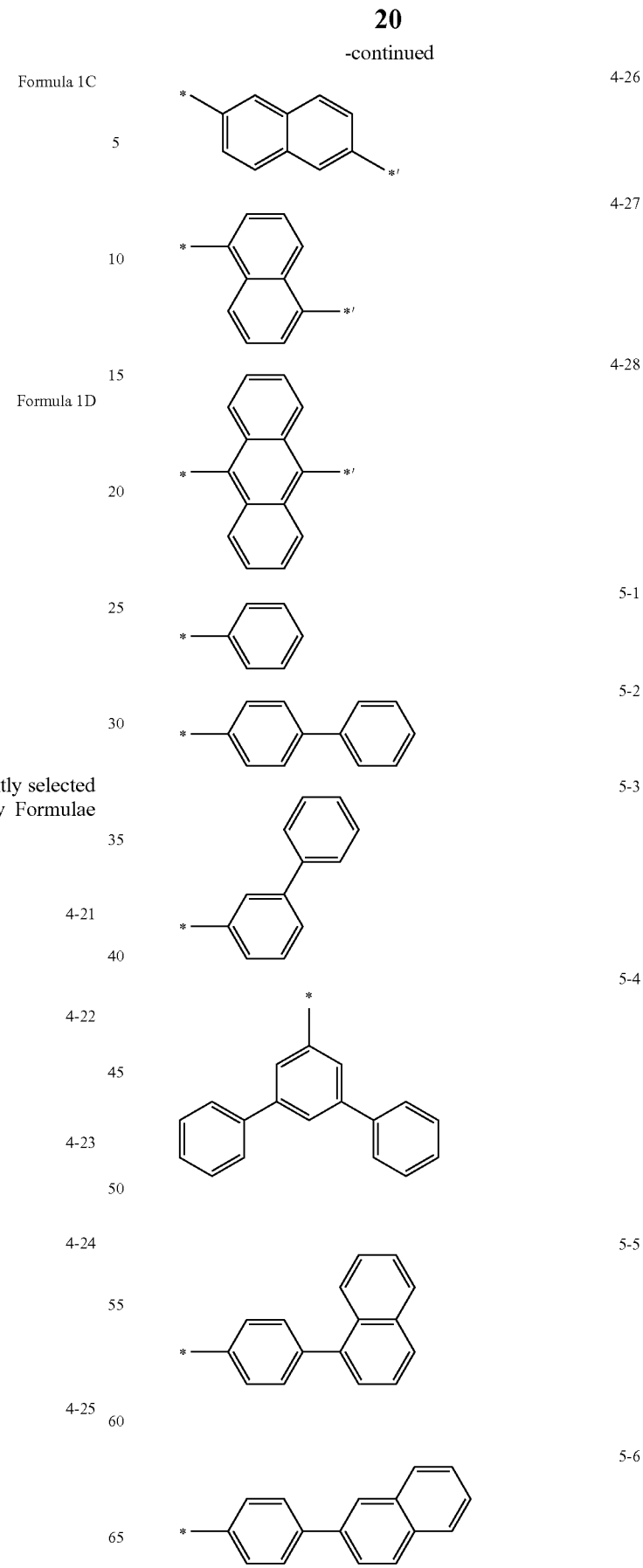

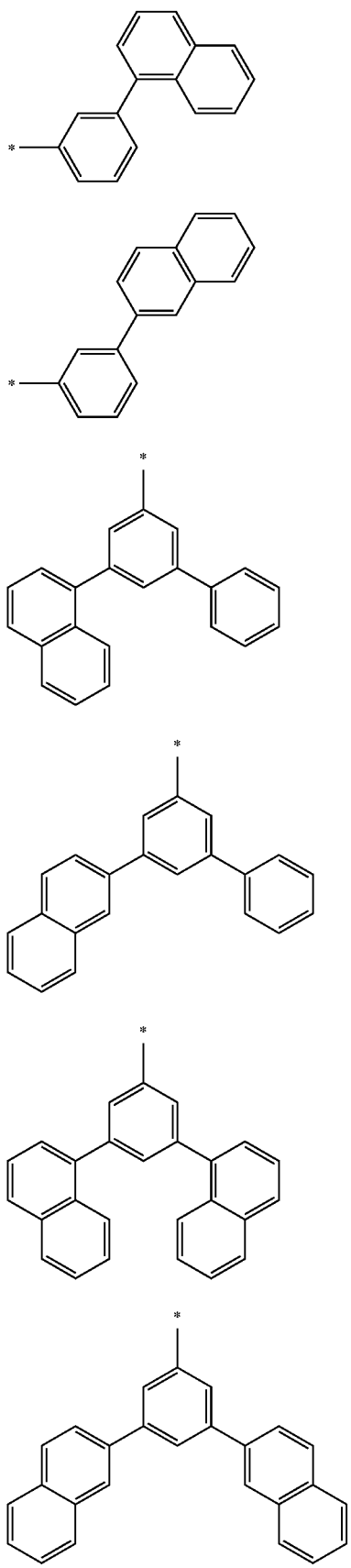
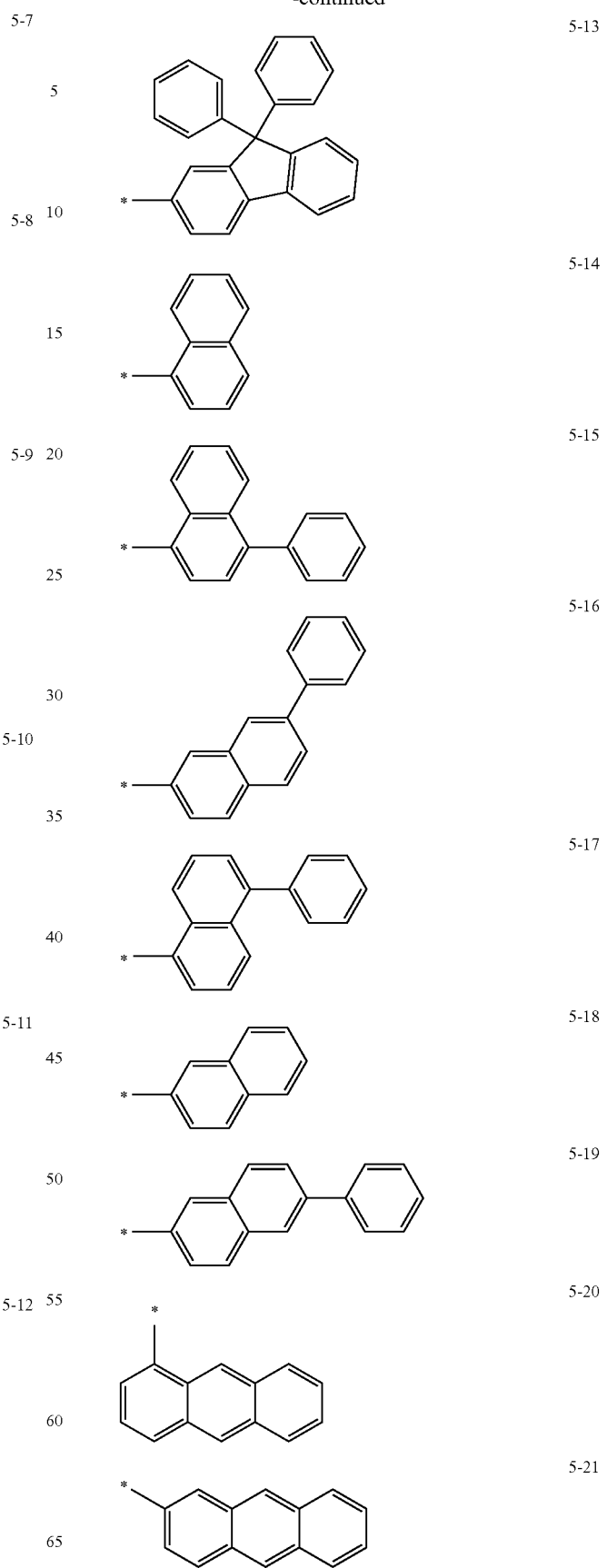

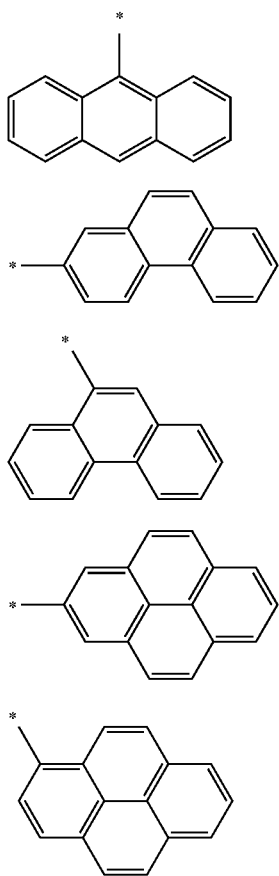
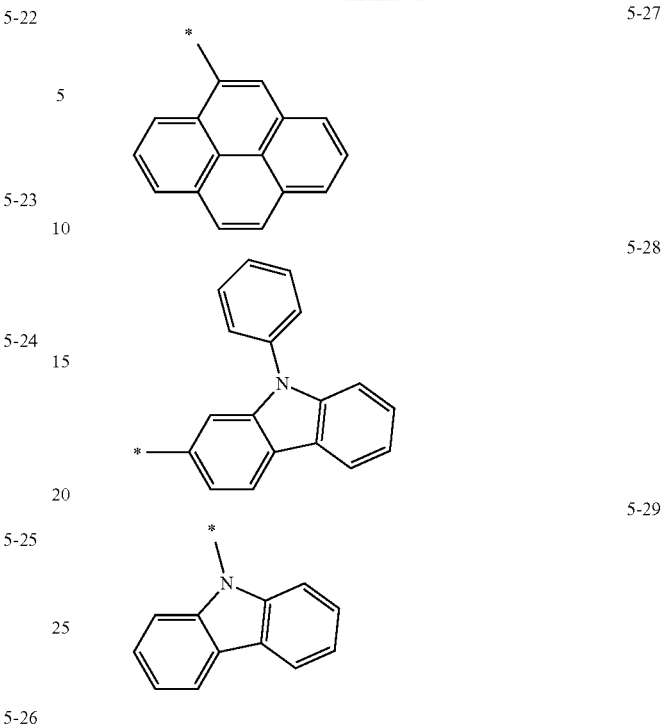
wherein * and *' in Formulae 4-21 to 4-28 may each independently indicate a binding site to a neighboring atom, and * in Formula 5-1 to 5-29 may indicate a binding site to a different atom.
In another example embodiment, the antiaromatic compound of Formula 1 may be selected from Compounds 1 to 43, but it is not limited thereto:
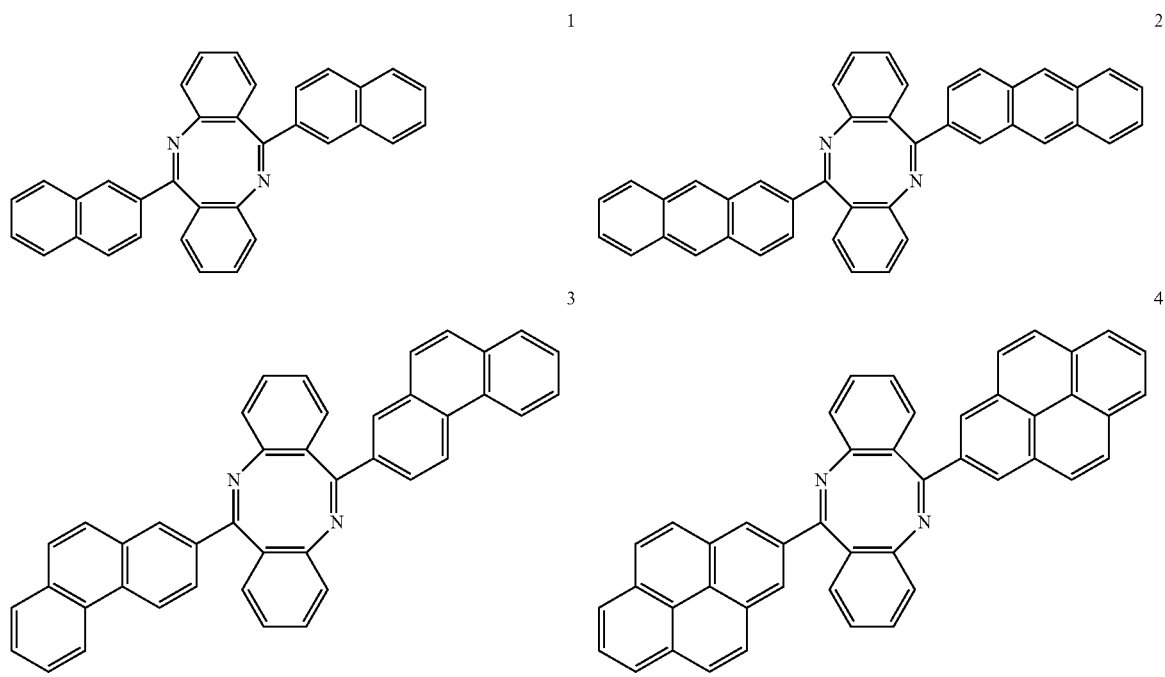

-continued
5
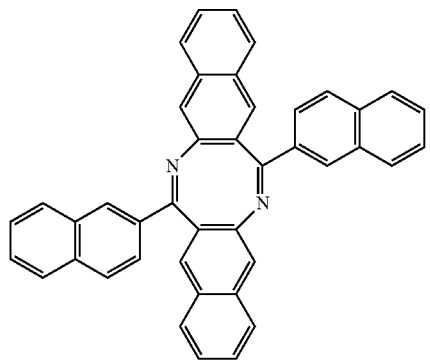
6
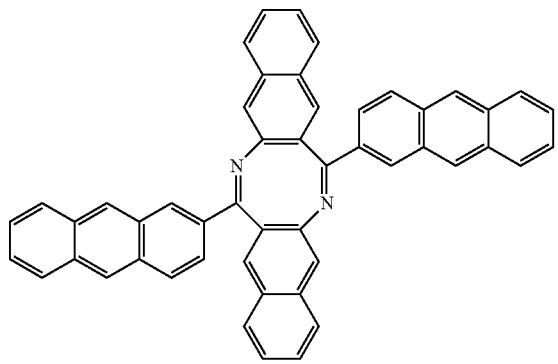
7
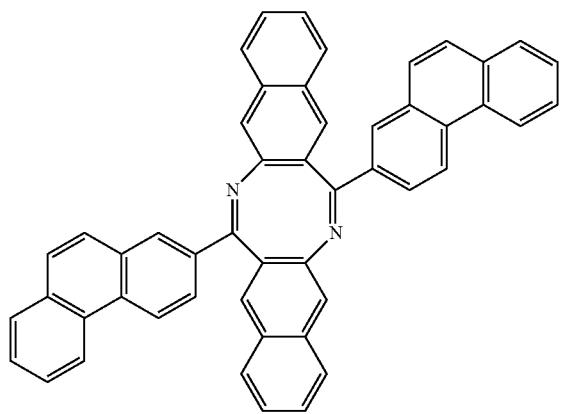
8
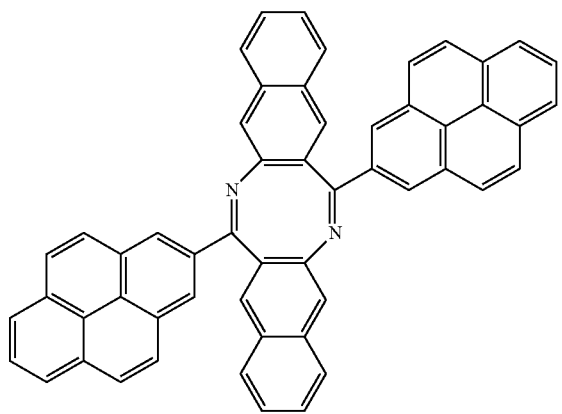
9
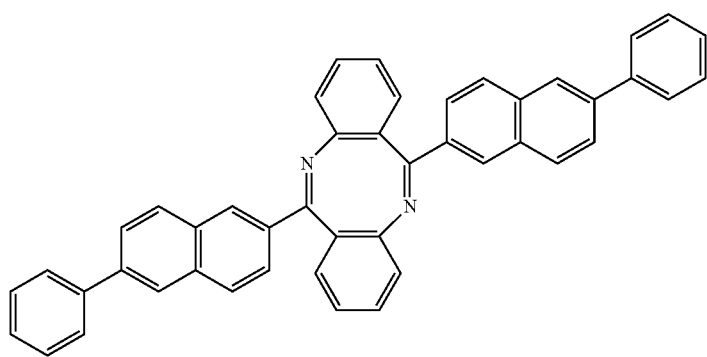
10
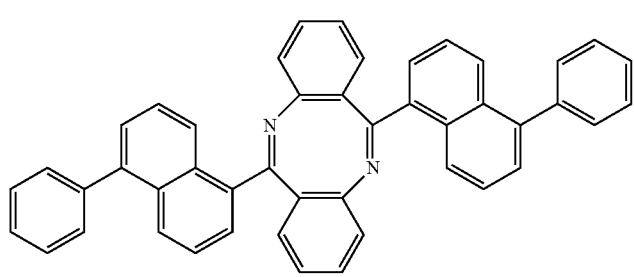

-continued
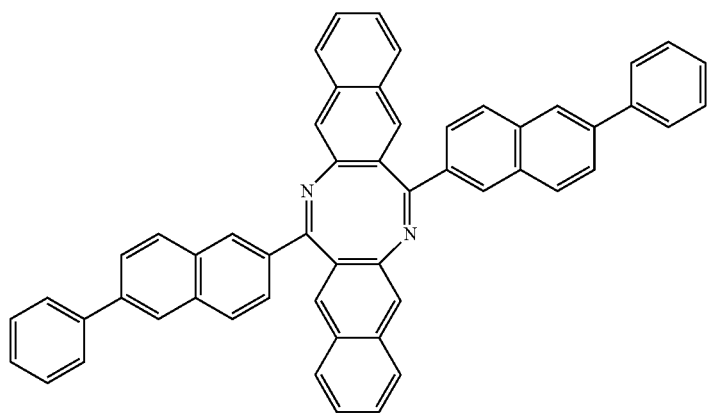
11
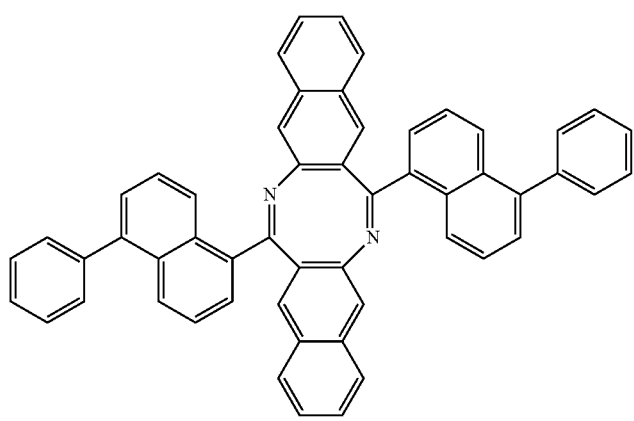
12
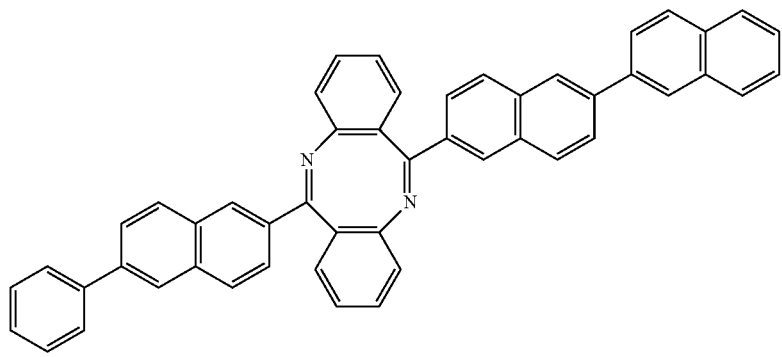
13
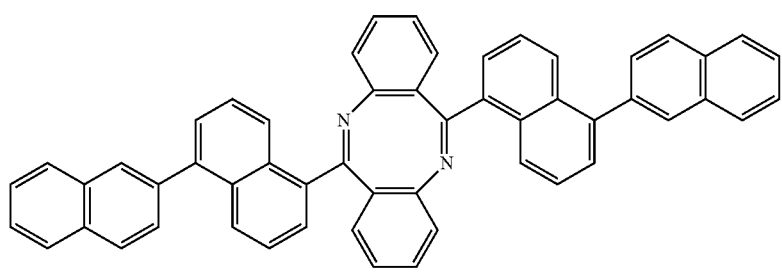
14

15
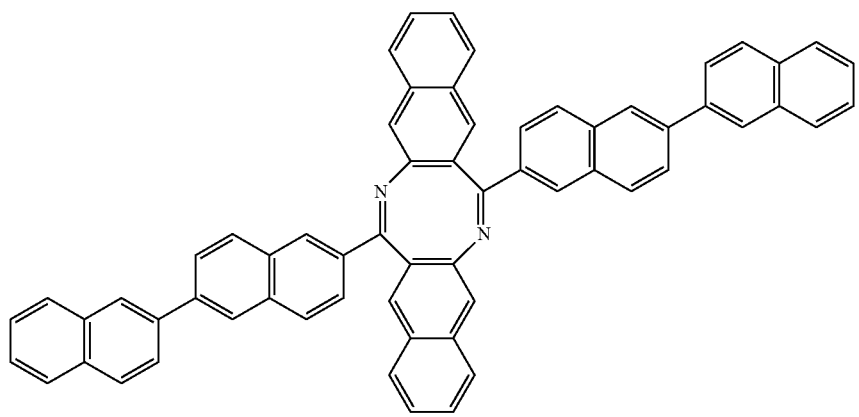
16
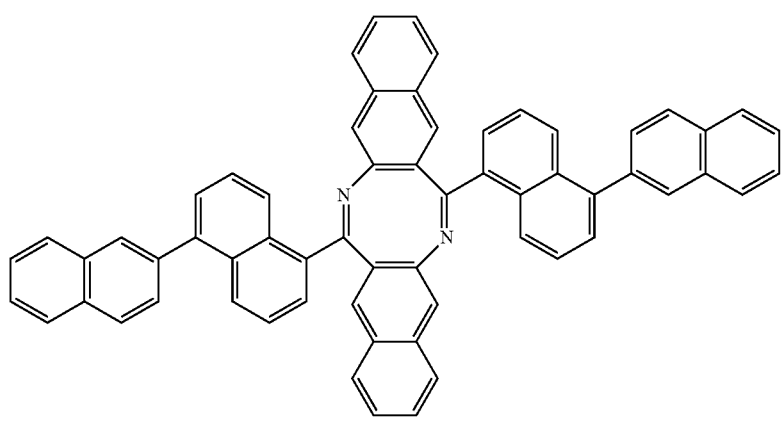
17
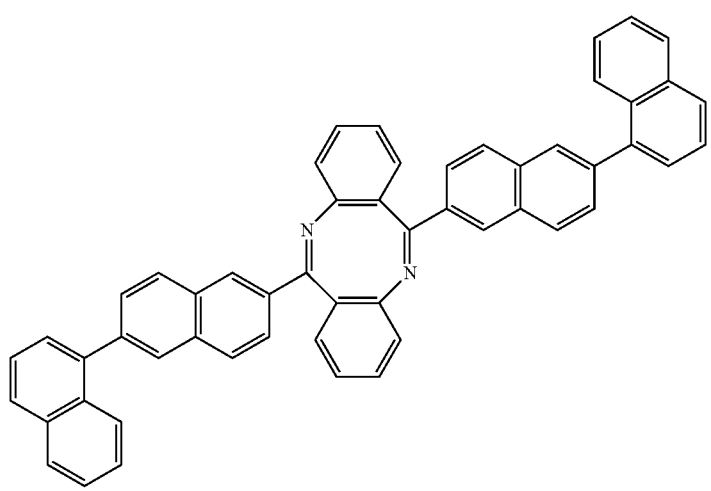
18
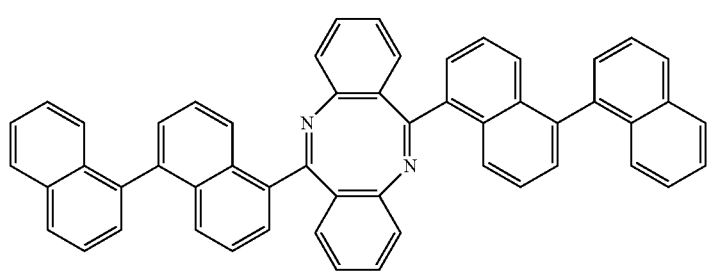

19
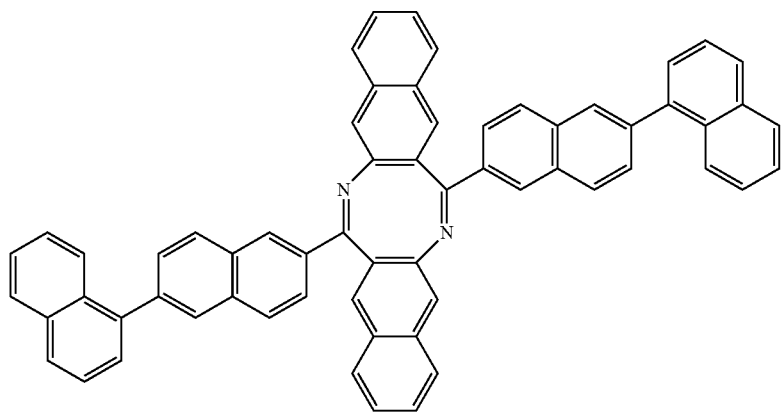
20
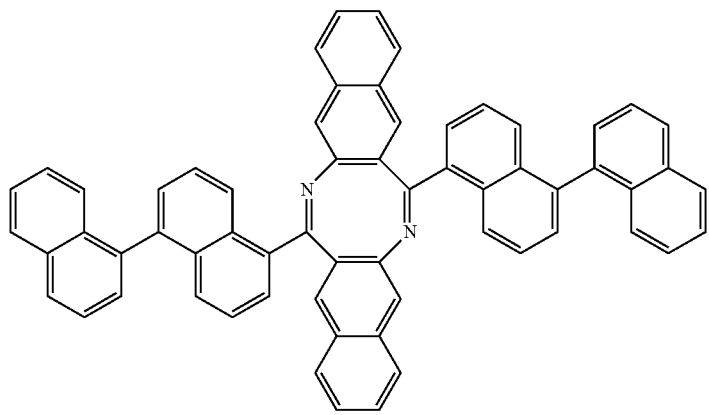
21
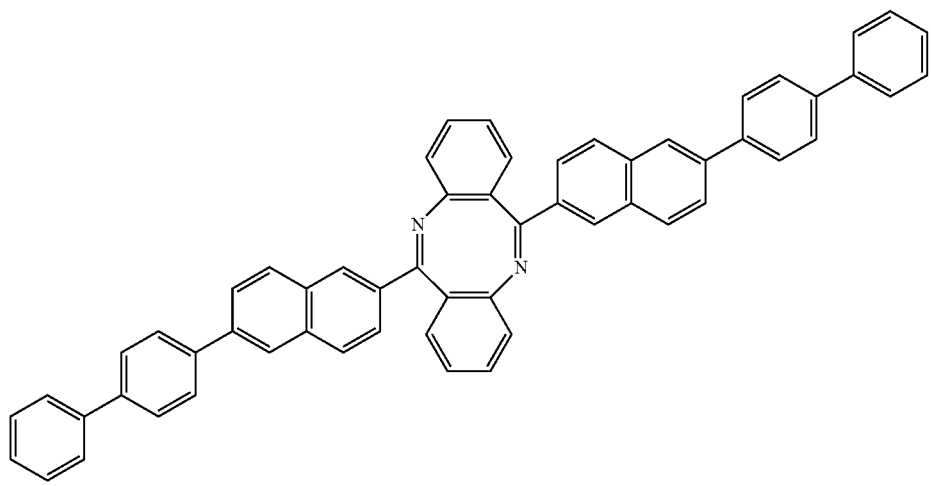
22
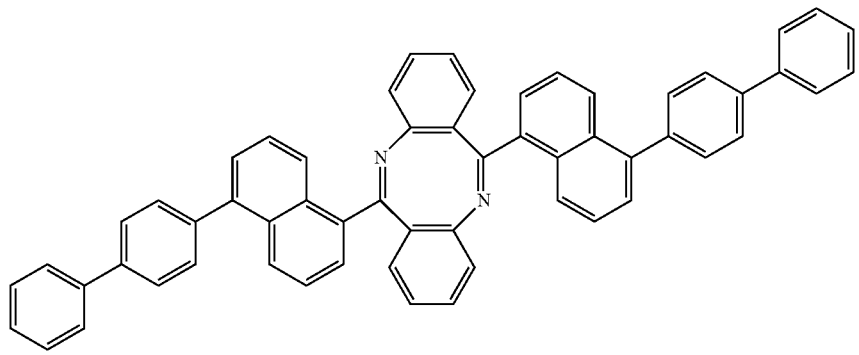

-continued
23
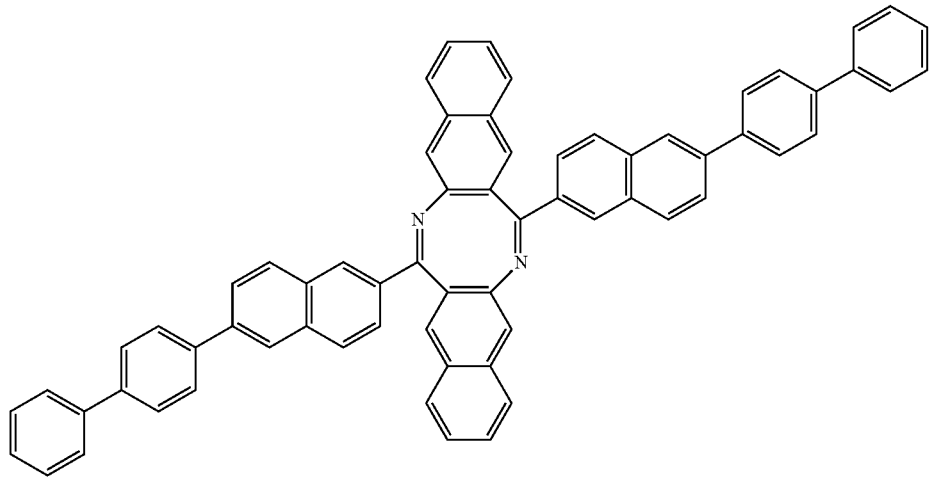
24
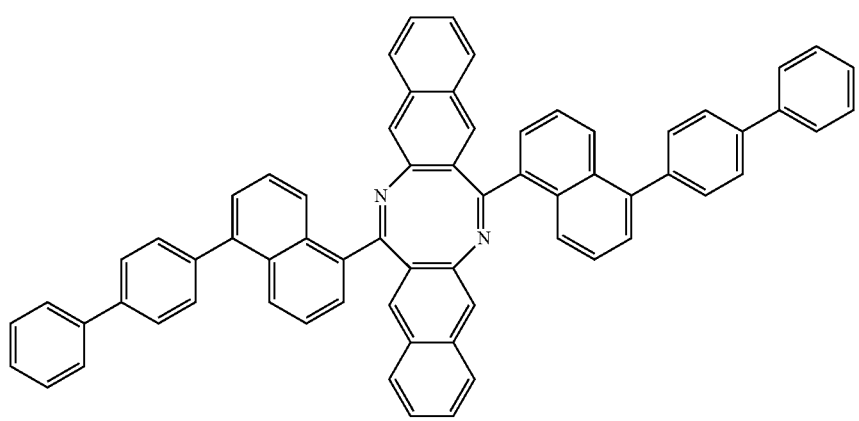
25
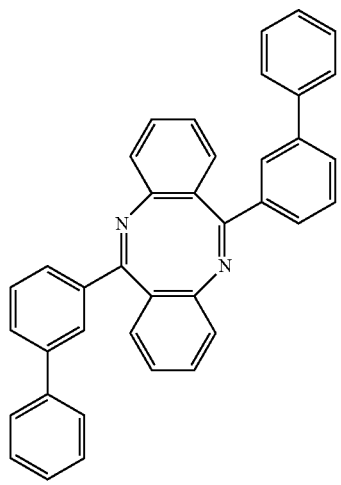
26
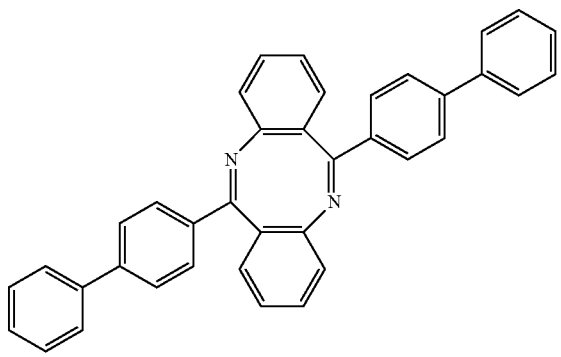

-continued
27
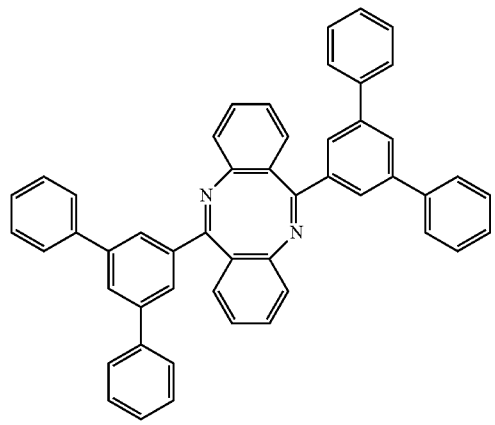
28
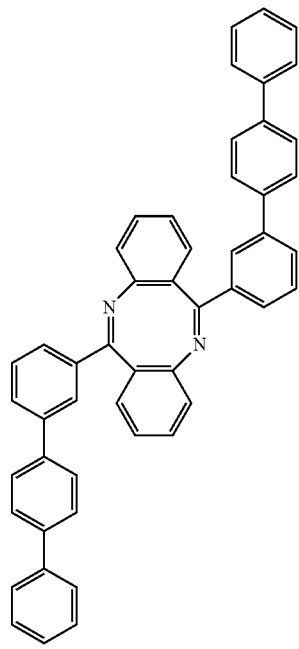
29
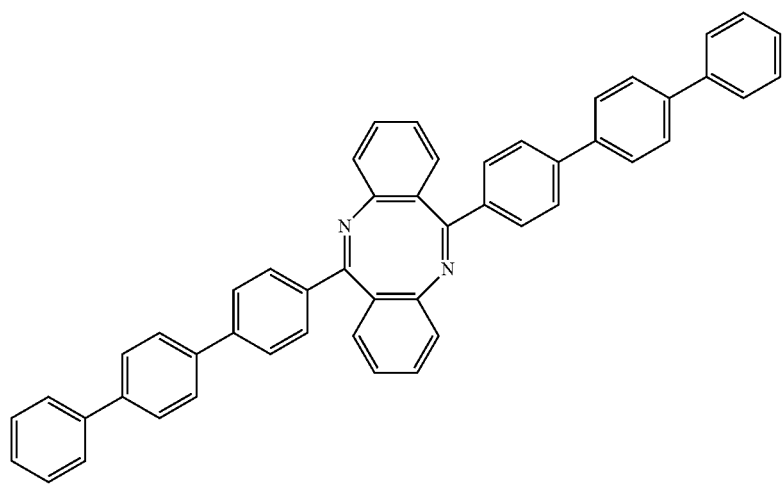

30
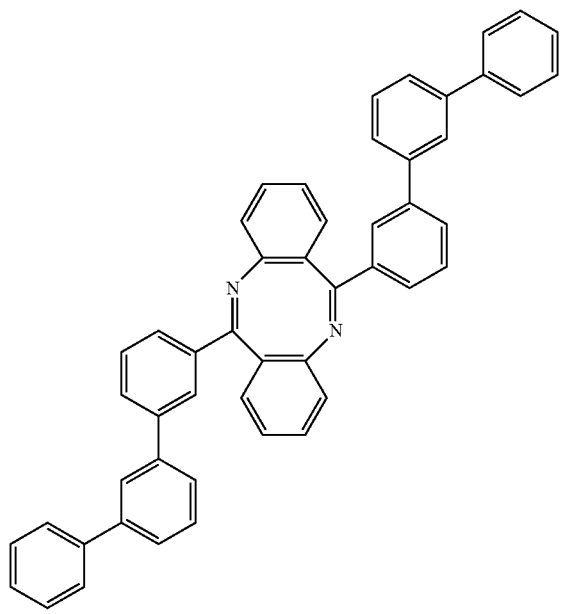
31
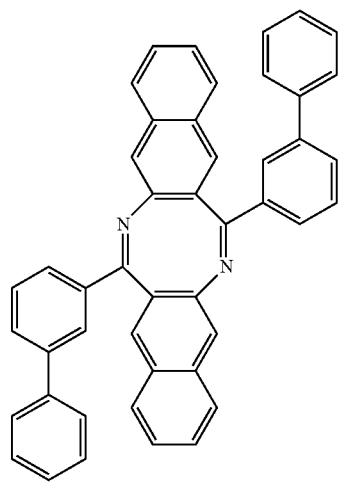
32
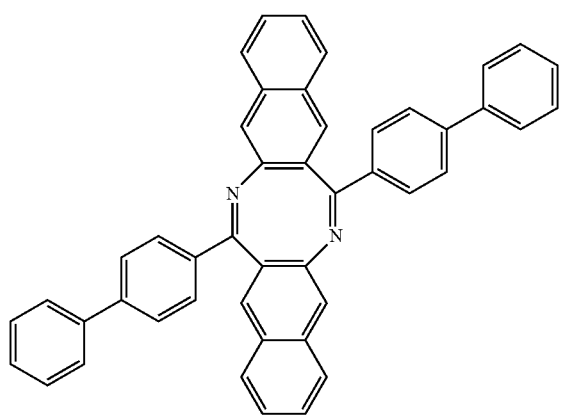
33
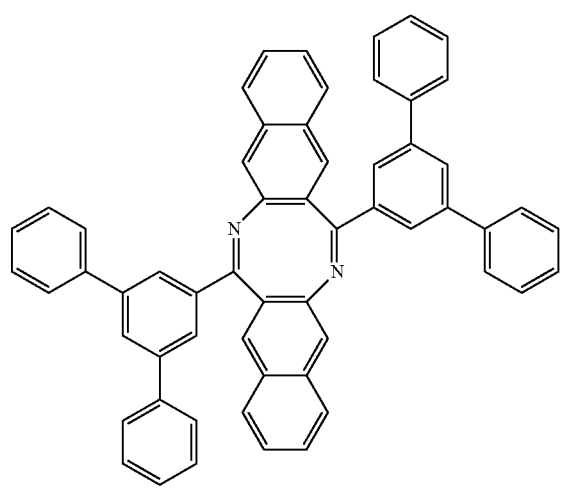

-continued
34
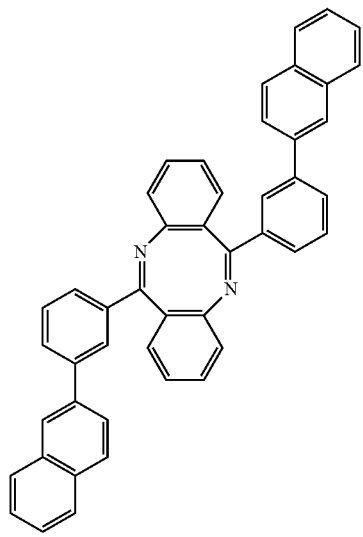
35
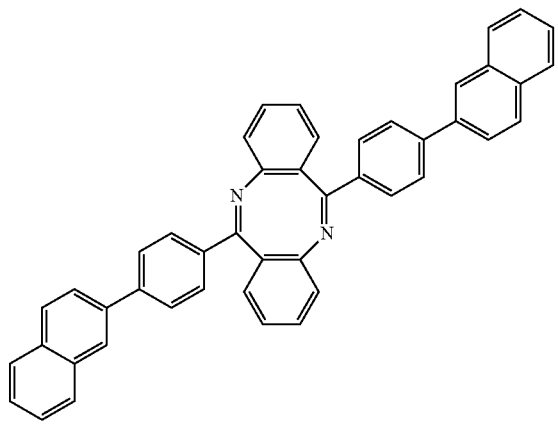
36
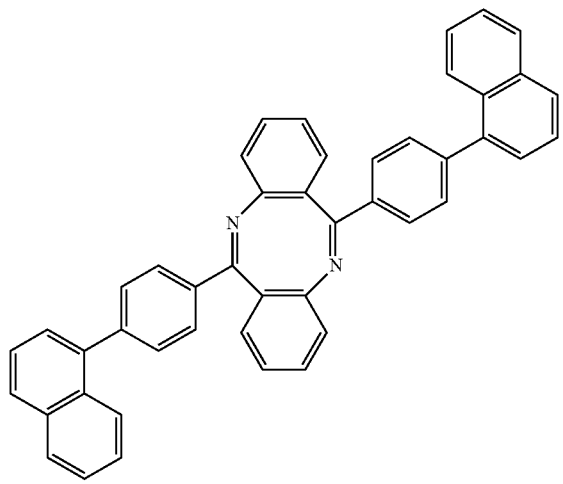
37
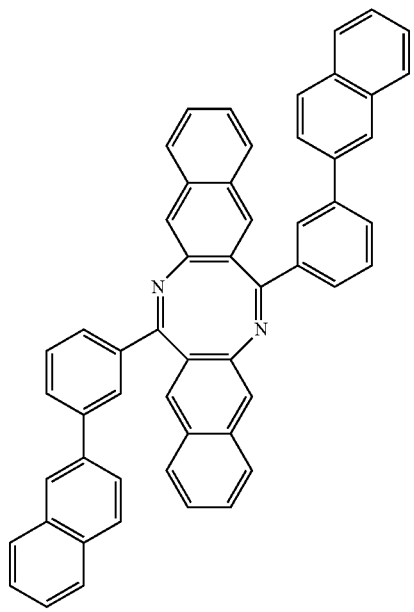
38
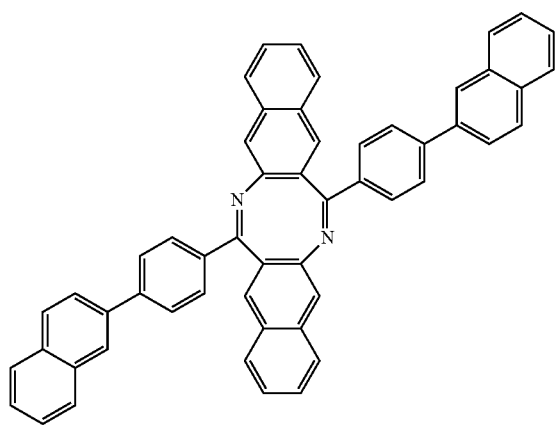
39
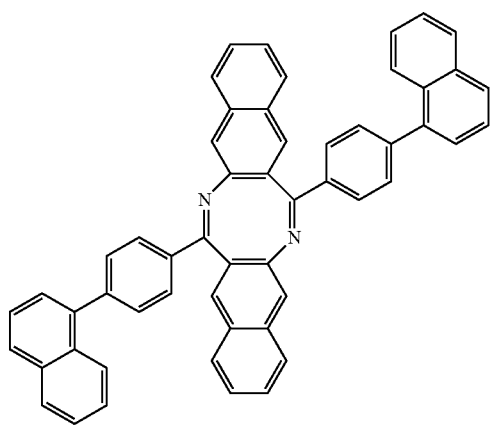

40
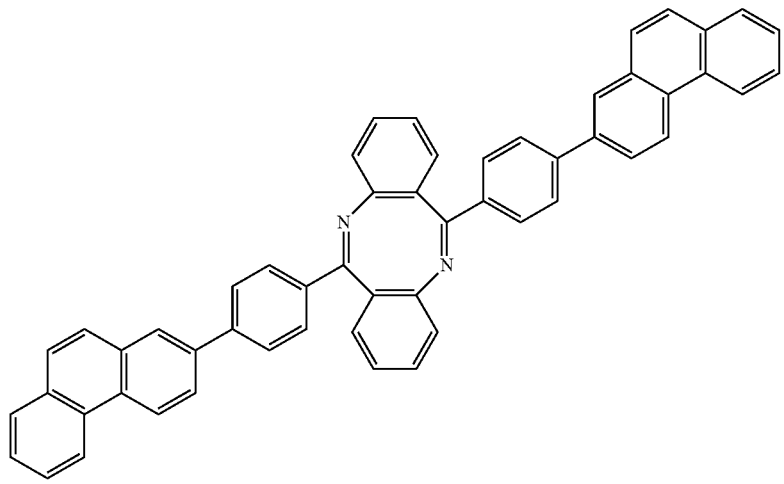
41
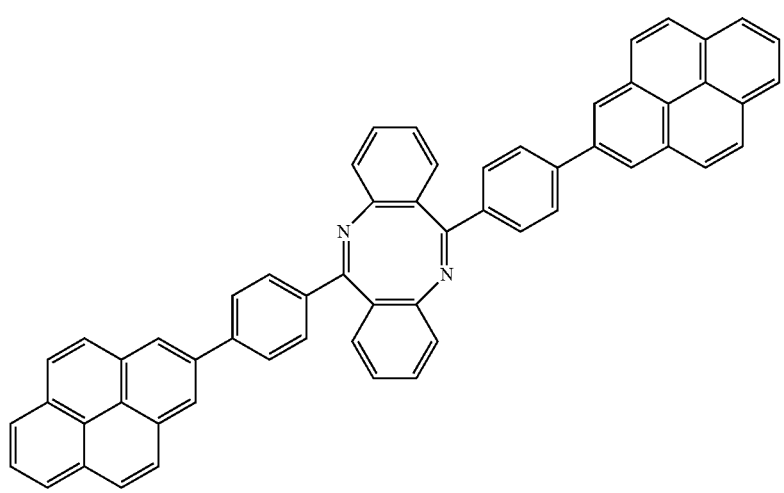
42
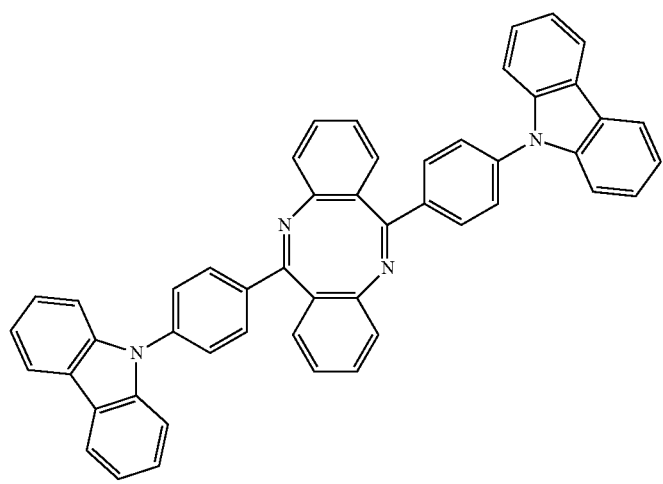

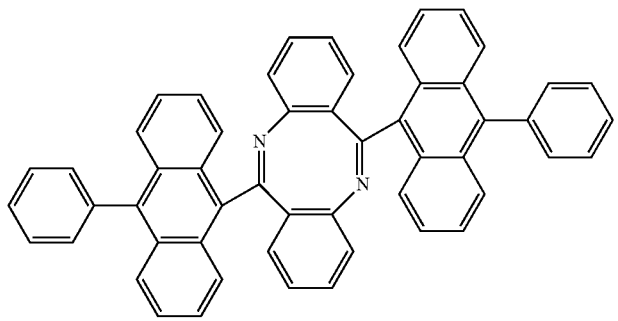

Hereinafter, a structure of an organic light-emitting device according to an example embodiment and a method of manufacturing an organic light-emitting device according to an example embodiment will be described in connection with FIG. 1.

An organic light-emitting device 10 of FIG. 1 may further include a substrate that is disposed under a first electrode 110 or above a second electrode 190. The substrate may be a glass substrate or a transparent plastic substrate, each having excellent mechanical strength, thermal stability, transparency, surface smoothness, ease of handling, and water-resistance.

The first electrode 110 may be formed by, e.g., depositing or sputtering a material for forming the first electrode 110 on the substrate. When the first electrode 110 is an anode, the material for forming the first electrode 110 may be selected from materials having a high work function to facilitate hole injection. The first electrode 110 may be a reflective electrode, a semi-refractive electrode, or a transparent electrode. The material for forming the first electrode 110 may be a transparent and highly conductive material, and examples of such a material include indium tin oxide (ITO), indium zinc oxide (IZO), tin oxide ($SnO_2$), and zinc oxide (ZnO). When the first electrode 110 is a semi-transparent electrode or a reflective electrode, at least one of magnesium (Mg), aluminum (Al), aluminum-lithium (Al—Li), calcium (Ca), magnesium-indium (Mg—In), and magnesium-silver (Mg—Ag) may be utilized as a material for forming the first electrode 110.

The first electrode 110 may have a single-layered structure or a multi-layered structure including a plurality of layers. For example, the first electrode (110) may have a three-layered structured of ITO/Ag/ITO, but the structure of the first electrode 110 is not limited thereto.

An organic layer 150 is disposed on the first electrode 110, and may include an emission layer.

The organic layer 150 may further include a hole transport region disposed between the first electrode 110 and the emission layer, an electron transport region disposed between the emission layer and the second electrode 190, and a mixed layer disposed between the emission layer and the electron transport region.

The hole transport region may include at least one selected from a hole injection layer (HIL), a hole transport layer (HTL), a buffer layer, and an electron blocking layer (EBL); and the electron transport region may include at least one selected from a hole blocking layer (HBL), an electron transport layer (ETL), and an electron injection layer (EIL), but the hole transport region and the electron transport region are not limited thereto.

The hole transport region may have a single-layered structure formed of a single material, a single-layered structure formed of a plurality of different materials, or a multi-layered structure having a plurality of layers formed of a plurality of different materials.

For example, the hole transport region have a single-layered structure formed of a plurality of different materials, or a multi-layered structure such as a structure of HIL/HTL, a structure of HIL/HTL/buffer layer, a structure of HIL/buffer layer, a structure of HTL/buffer layer, or a structure of HIL/HTL/EBL. Layers of each structure are sequentially stacked from the first electrode 110 in this stated order, but the hole transport region is not limited thereto.

When the hole transport region includes an HIL, the HIL may be formed on the first electrode 110 by utilizing various suitable methods, such as vacuum deposition, spin coating, casting, a Langmuir-Blodgett (LB) method, ink-jet printing, laser-printing, or a laser-induced thermal imaging (LITI) method.

When an HIL is formed by vacuum deposition, the vacuum deposition may be performed, e.g., at a deposition temperature of about 100° C. to about 500° C., at a vacuum degree of about $10^{-8}$ torr to about $10^{-3}$ torr, and a deposition rate of about 0.01 Å/sec to about 100 Å/sec, depending upon a composition of a compound for forming the HIL to be deposited and a structure of the HIL to be formed.

When an HIL is formed by spin coating, the coating may be performed, e.g., at a coating speed of about 2,000 rpm to about 5,000 rpm and at a temperature of about 80° C. to about 200° C., depending upon a composition of a compound for forming the HIL to be deposited and a structure of the HIL to be formed.

When the hole transport region includes an HTL, the HTL may be formed on the first electrode 110 or the HIL by utilizing various suitable methods, such as vacuum deposition, spin coating, casting, an LB method, an ink-jet printing, a laser-printing, or an LITI method. When the HTL is formed by vacuum deposition and/or spin coating, the deposition and coating conditions for the HTL may be determined by referring to the deposition and coating conditions for the HIL.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrene-sulfonate) (PEDOT/PSS), polyaniline/camphor sulfonic acid (Pani/CSA), polyaniline/poly(4-styrenesulfonate) (PANI/PSS), a quinone derivative such as tetracyanoquinonedimethane (TCNQ) and 2,3,5,6-tetrafluoro-tetracyano-1,4-benzoquinonedimethane (F4-TCNQ), Compound HT-D1, a compound represented by Formula 201, and a compound represented by Formula 202:
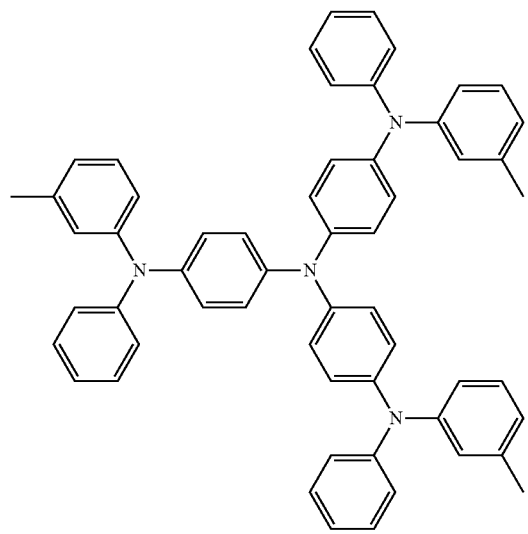
m-MTDATA
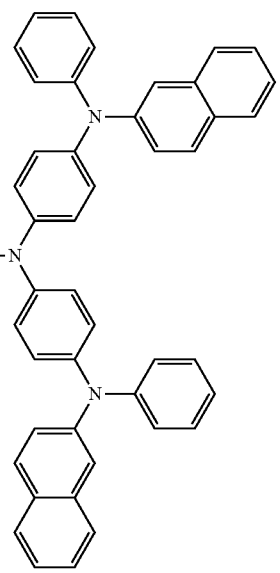
2-TNATA
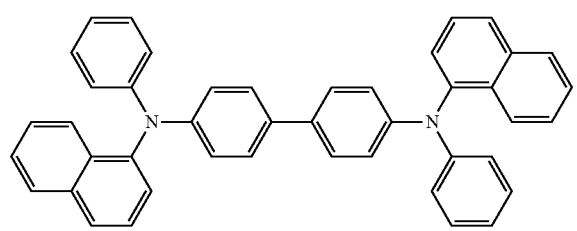
NPB
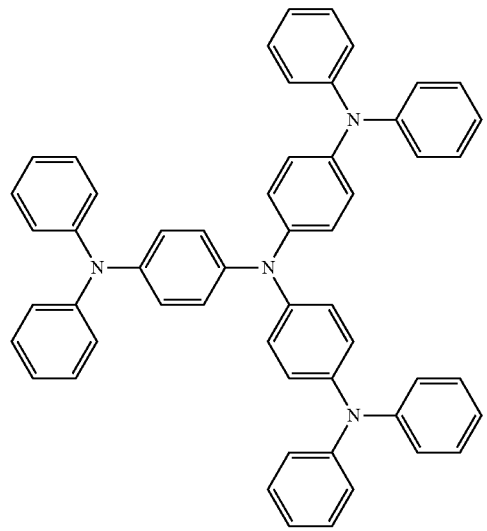
TDATA
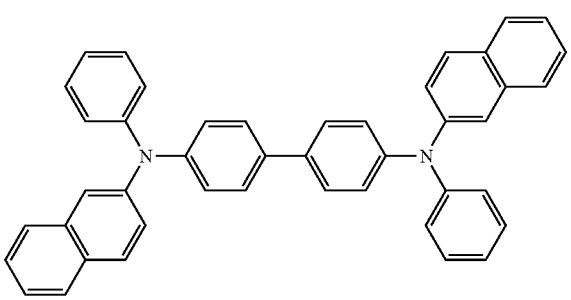
β-NPB
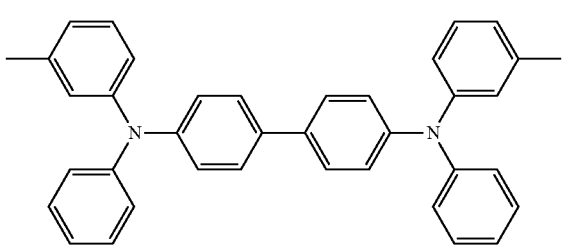
TPD -continued

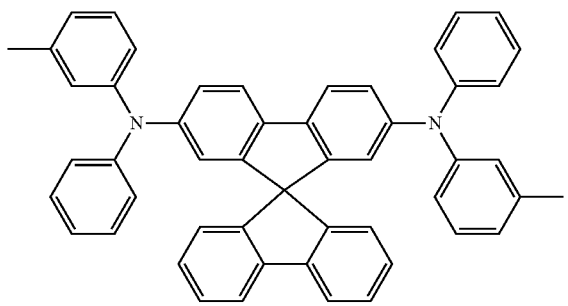
Spiro-TPD

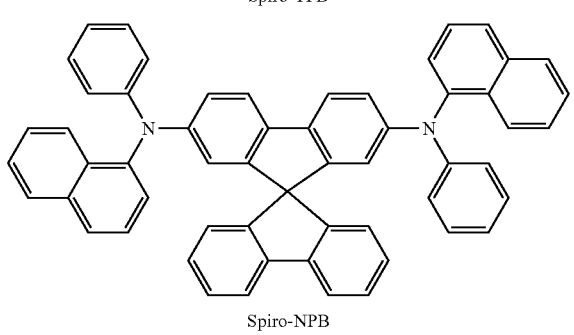
Spiro-NPB

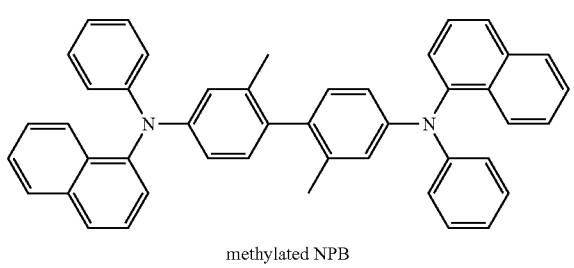
methylated NPB

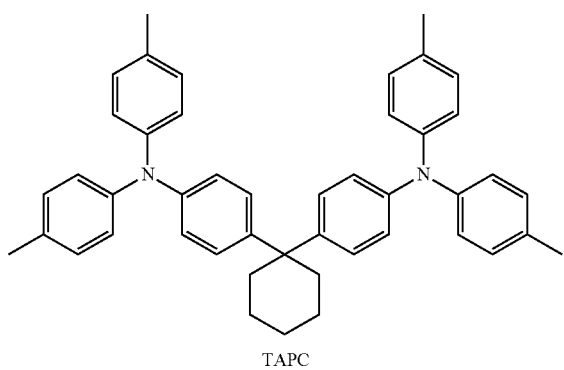
TAPC

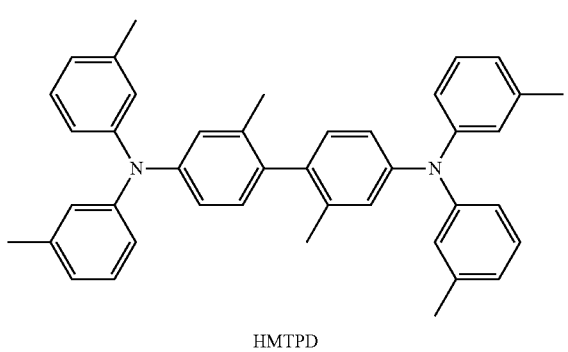
HMTPD

-continued

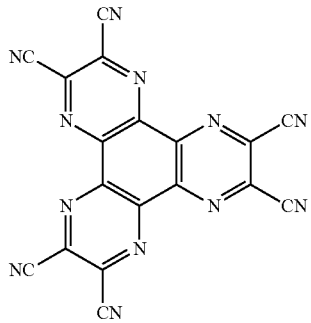
Compound HT-D1

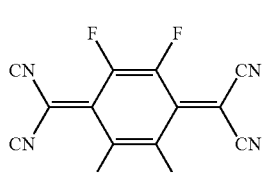
F4-TCNQ

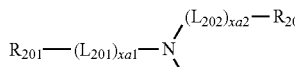
Formula 201

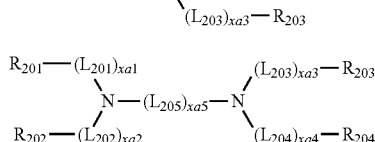
Formula 202

In Formulae 201 and 202, descriptions of $L_{201}$ to $L_{205}$ may be each independently as referred to in the description provided in connection with $L_{11}$ (e.g., $L_{201}$ to $L_{205}$ may each independently be substantially the same as described with respect to $L_{11}$);

xa1 to xa4 may be each independently selected from 0, 1, 2, and 3;

xa5 may be selected from 1, 2, 3, 4, and 5; and $R_{201}$ to $R_{204}$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed antiaromatic compound, and a monovalent non-aromatic condensed heteropolycyclic group.

For example, in Formula 201 and 202, $L_{201}$ to $L_{205}$ may be each independently selected from:

a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently 0, 1, or 2;

xa5 may be 1, 2, or 3; and $R_{201}$ to $R_{204}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but $R_{201}$ to $R_{204}$ are not limited thereto.

The compound represented by Formula 201 may be represented by Formula 201A:

Formula 201A

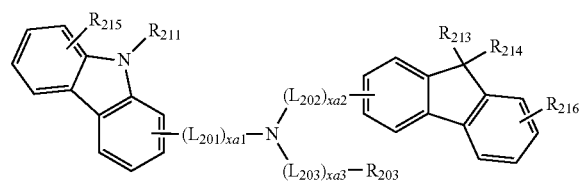

For example, the compound represented by Formula 201 may be represented by Formula 201A-1, but the compound represented by Formula 201 is not limited thereto:

Formula 201A-1

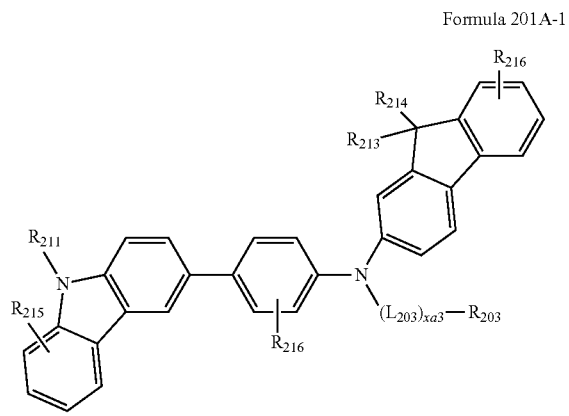

The compound represented by Formula 202 may be represented by Formula 202A, but the compound represented by Formula 202 is not limited thereto:

Formula 202A

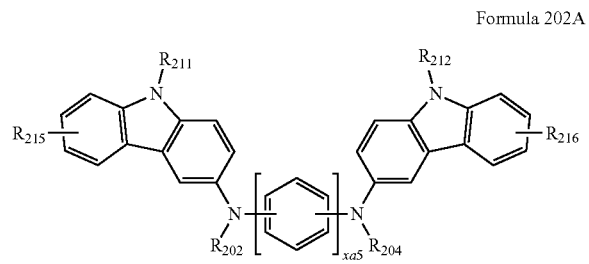

In Formulae 201A, 201A-1, and 202A, descriptions of $L_{201}$ to $L_{203}$, xa1 to xa3, xa5, and $R_{202}$ to $R_{204}$ may be each independently as referred to in the descriptions provided above, a description of $R_{211}$ and $R_{212}$ may be each independently as referred to in the description provided in connection with $R_{203}$ (e.g., $R_{211}$ and $R_{212}$ may each independently be substantially the same as described with respect to $R_{203}$), and $R_{213}$ to $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

For example, in Formulae 201A, 201A-1, and 202A, $L_{201}$ to $L_{203}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may be each independently 0 or 1;

$R_{203}$, $R_{211}$, and $R_{212}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, carboxylic acid a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may be each independently selected from:
a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ may be each independently selected from:
a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 may be 1 or 2.

In Formulae 201A and 201A-1, $R_{213}$ and $R_{214}$ may bind to each other to form a saturated or unsaturated ring.

The compound represented by Formula 201 and the compound represented by Formula 202 may each include at least one selected from Compounds HT1 to HT20 below, but the compound represented by Formula 201 and the compound represented by Formula 202 are not limited thereto.

HT1

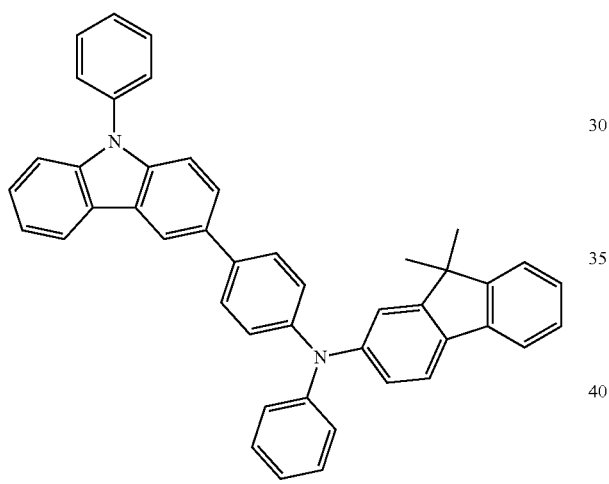

HT2

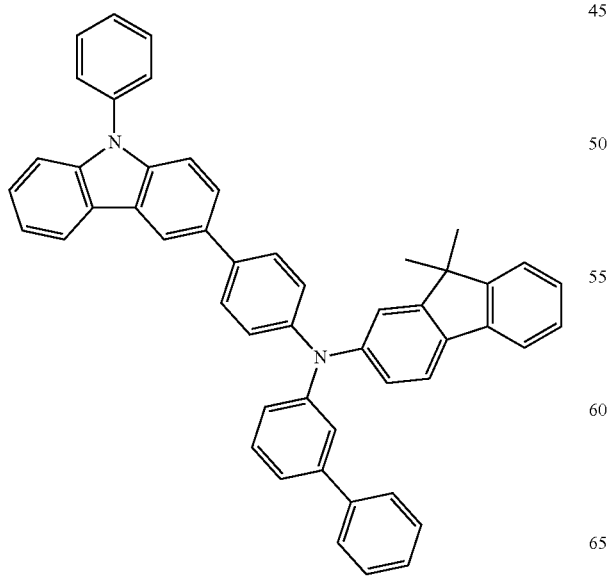

HT3

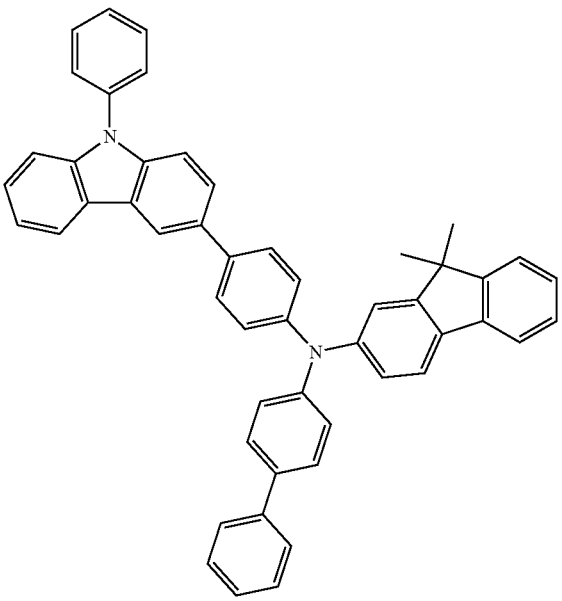

HT4

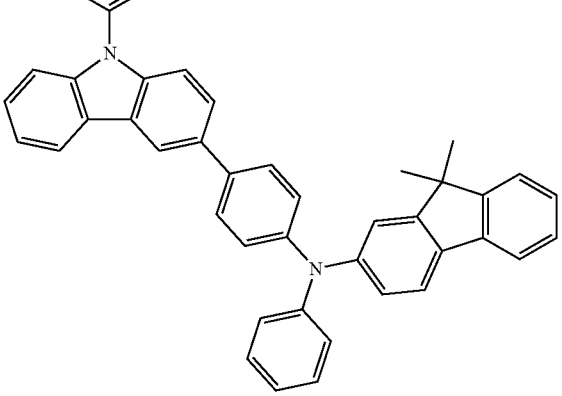

HT5
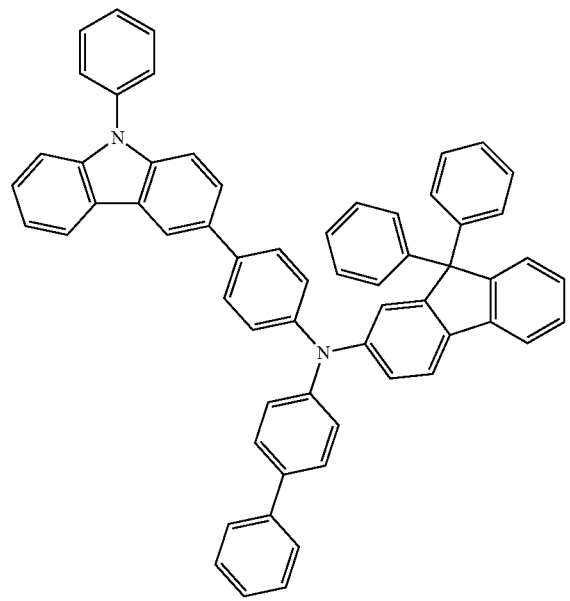
HT6
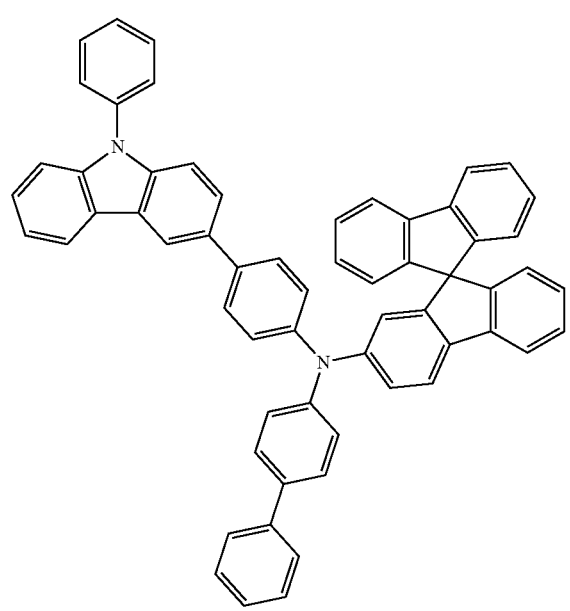
HT7
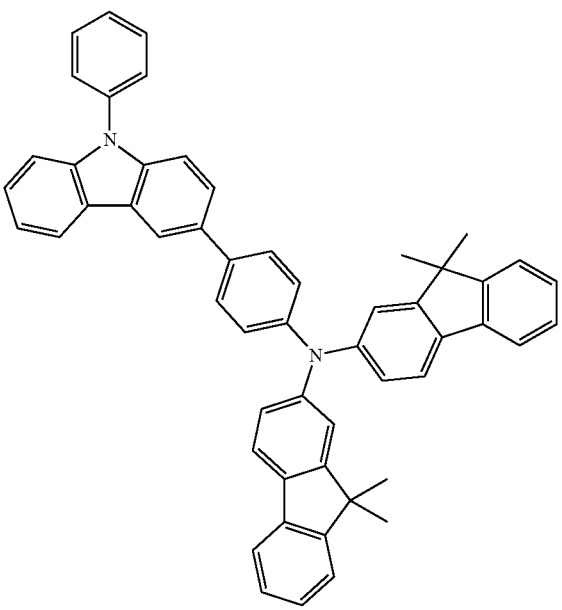
HT8
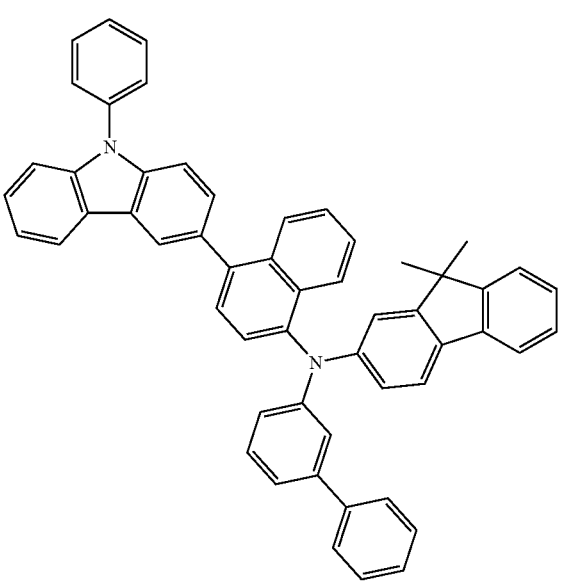

-continued
HT9
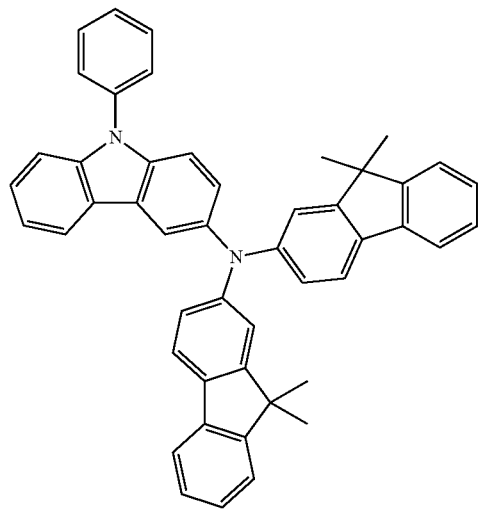
HT11
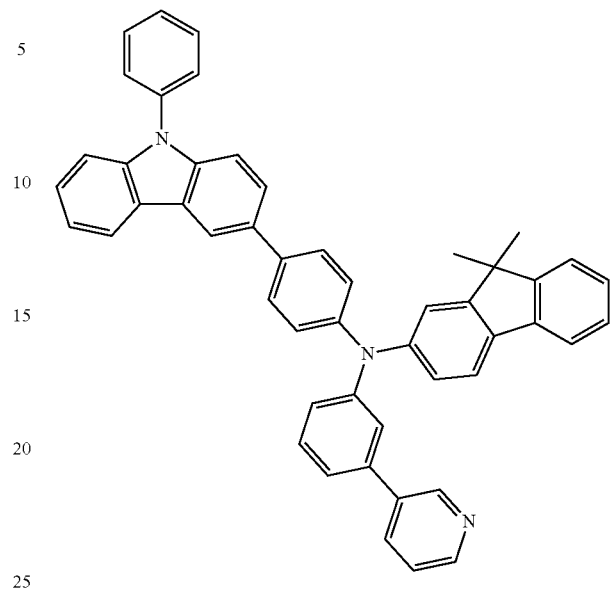
HT12
HT10
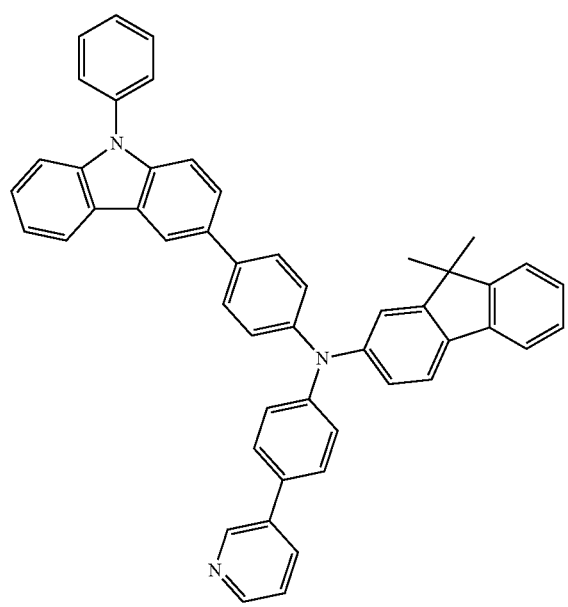
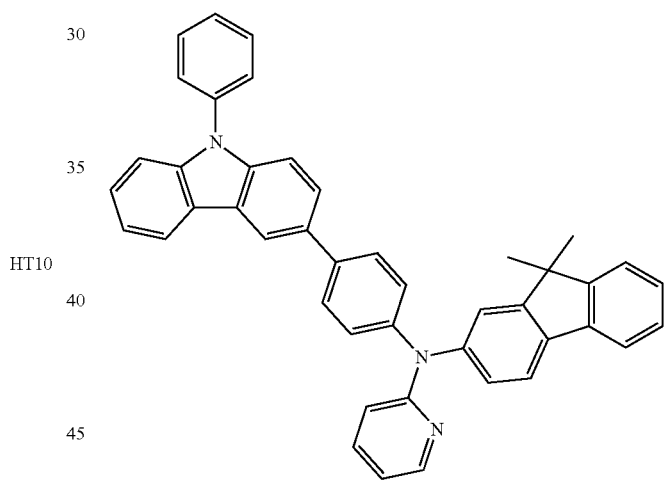
HT13
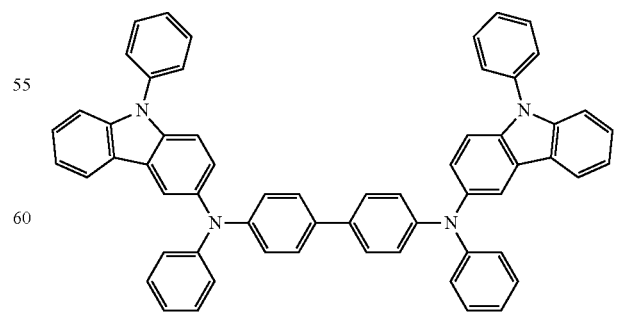

HT14
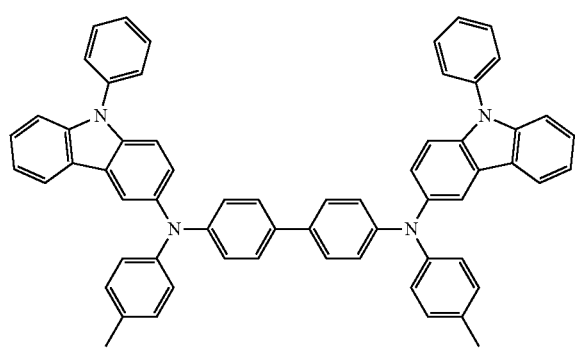

HT15
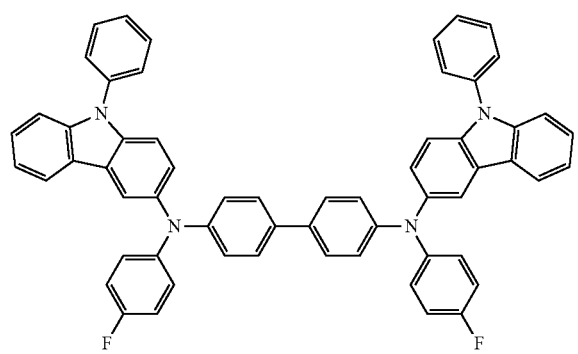

HT16
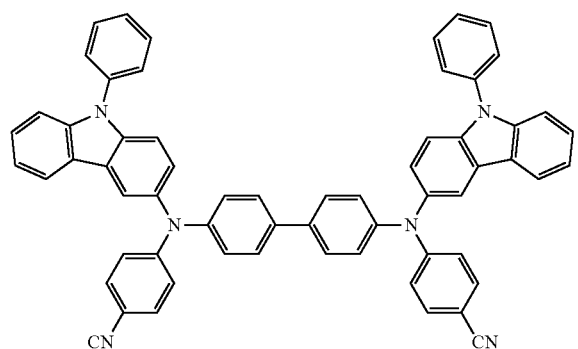

HT17
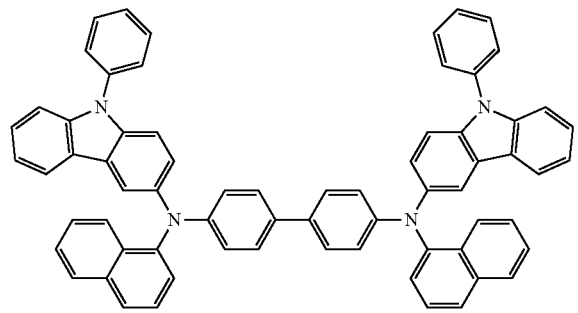

HT18
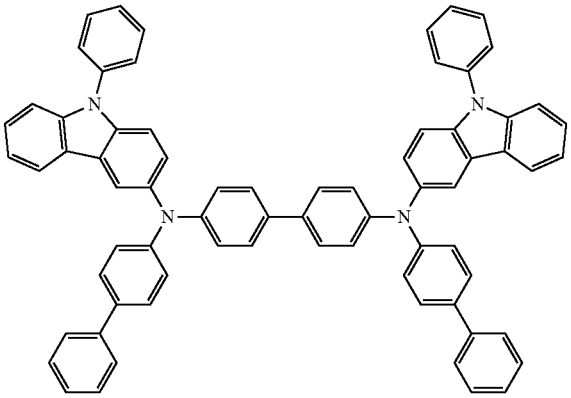

HT19
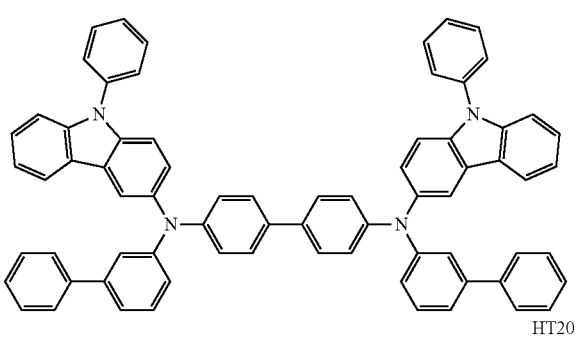

HT20
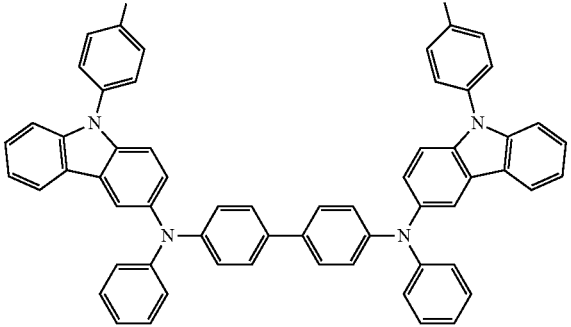

A thickness of the hole transport region may be in a range of about 100 Å to about 10,000 Å, for example, about 100 Å to about 1,000 Å. When the hole transport region includes both an HIL and an HTL, a thickness of the HIL may be in a range of about 100 Å to about 10,000 Å, for example, about 100 Å to about 1,000 Å; and a thickness of the HTL may be in a range of about 50 Å to about 2,000 Å, for example about 100 Å to about 1,500 Å. In one example embodiment, when the thickness of the hole transport region, the HIL, and the HTL are within these ranges, satisfactory or suitable hole transporting characteristics are obtained without a substantial increase in driving voltage.

The hole transport region may further include, in addition to these materials, a charge-generation material for the improvement of conductive properties. The charge-generation material may be homogeneously or inhomogeneously dispersed in the hole transport region.

The charge-generation material may be, for example, a p-dopant. The p-dopant may be one selected from a quinone derivative, a metal oxide, and a cyano group-containing compound, but the p-dopant is not limited thereto. For example, non-limiting examples of the p-dopant are a quinone derivative such as TCNQ and F4-TCNQ); a metal oxide such as a tungsten oxide and a molybdenum oxide; and Compound HT-D1 above, but the p-dopant is not limited thereto.

The hole transport region may further include, in addition to the HIL and the HTL, at least one of a buffer layer and an EBL. Since the buffer layer may compensate for an optical resonance distance according to a wavelength of light emitted from the emission layer, light-emission efficiency of a formed organic light-emitting device may be improved. For usage as a material included in the buffer layer, materials that are included in the hole transport region may be utilized. The EBL may reduce or prevent injection of electrons from the electron transport region.

The hole transport layer may include a first HTL and a second HTL, and each of the first HTL and the second HTL may concurrently (or simultaneously) include the same or substantially the same material, or the first HTL and the second HTL may be formed of different materials from each other.

The emission layer may be formed on the first electrode 110 or on the hole transport region by utilizing various suitable methods, such as vacuum deposition, spin coating, casting, an LB method, an ink-jet printing, a laser-printing, or an LITI method. When the emission layer is formed by vacuum deposition and/or spin coating, the deposition and coating conditions for the HTL may be determined by referring to the deposition and coating conditions for the HIL.

When the organic light-emitting device 10 is a full color organic light-emitting device, the emission layer may be patterned into a red emission layer, a green emission layer, or a blue emission layer, according to individual sub pixels, respectively. The emission layer may have various modifications in the structure, and for example, may have a structure of a red emission layer, a green emission layer, and a blue emission layer, each of which layers are sequentially stacked in the stated order, or a structure in which a red light-emitting material, a green light-emitting material, and a blue light-emitting material are mixed without distinction between layers, and accordingly the emission layer may emit white light.

The emission layer may include a host and a dopant.

The host may include the antiaromatic compound represented by Formula 1 above.

The dopant may include at least one selected from a fluorescent dopant and a phosphorescent dopant.

The phosphorescent dopant may include an organic metal complex represented by Formula 401.

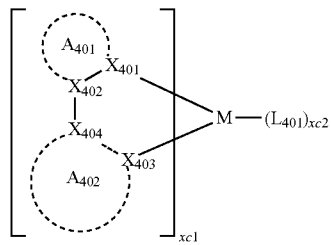

Formula 401

In Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may be each independently nitrogen or carbon;

rings $A_{401}$ and $A_{402}$ may be each independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene;

at least one substituent of the substituted benzene, the substituted naphthalene, the substituted fluorene, the substituted spiro-fluorene, the substituted indene, the substituted pyrrole, the substituted thiophene, the substituted furan, the substituted imidazole, the substituted pyrazole, the substituted thiazole, the substituted isothiazole, the substituted oxazole, the substituted isoxazole, the substituted pyridine, the substituted pyrazine, the substituted pyrimidine, the substituted pyridazine, the substituted quinoline, the substituted isoquinoline, the substituted benzoquinoline, the substituted quinoxaline, the substituted quinazoline, the substituted carbazole, the substituted benzoimidazole, the substituted benzofuran, the substituted benzothiophene, the substituted isobenzothiophene, the substituted benzoxazole, the substituted isobenzoxazole, the substituted triazole, the substituted oxadiazole, the substituted triazine, the substituted dibenzofuran, and the substituted dibenzothiophene may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, $C_1$-$C_{60}$ heteroaryl group, a monovalent non-aromatic condensed polycyclic group(non-aromatic condensed polycyclic group), a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$aryloxy group, a $C_6$-$C_{60}$arylthio group, a $C_1$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$);

$L_{401}$ may be an organic ligand;

xc1 may be 1, 2, or 3;

xc2 may be 0, 1, 2, or 3; and $Q_{401}$ to $Q_{407}$, $Q_{411}$ to $Q_{417}$, and $Q_{421}$ to $Q_{427}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group.

$L_{401}$ in Formula 401 may be a monovalent, divalent, or trivalent organic ligand. For example, $L_{401}$ in Formula 401 may be selected from a halogen ligand (e.g., Cl or F), a diketone ligand (e.g., acetylacetonate, 1,3-diphenyl-1,3-propan dionate, 2,2,6,6-tetramethyl-3,5-heptanedionate, or hexafluoroacetonate), a carboxylic acid ligand (e.g., picolinate, dimethyl-3-pyrazolecarboxylate, or benzoate), a carbon monoxide ligand, an isonitrile ligand, a cyano ligand, and a phosphorus ligand (e.g., phosphine or phosphite), but $L_{401}$ in Formula 401 is not limited thereto.

When $A_{401}$ in Formula 401 has two or more substituents, the two or more substituents of $A_{401}$ may be linked to each other to form a saturated or unsaturated ring.

When $A_{402}$ in Formula 401 has two or more substituents, the two or more substituents of $A_{402}$ may be linked to each other to form a saturated or unsaturated ring.

When xc1 in Formula 401 is 2 or greater, a plurality of ligands

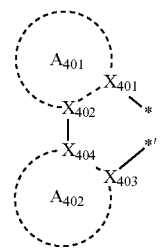

in Formula 401 may be identical to or different from each other. When xc1 in Formula 401 is 2 or greater, $A_{401}$ and $A_{402}$ may be respectively and directly linked to $A_{401}$ and $A_{402}$ of a different neighboring ligand, or may link to $A_{401}$ and $A_{402}$ of a different neighboring ligand via a linking group (e.g., a $C_1$-$C_5$ alkylene group, —N(R')-(where R' is a $C_1$-$C_{10}$ alkyl group or a $C_6$-$C_{20}$ aryl group), or —C(=O)—) therebetween.

The phosphorescent dopant may include at least one of Compounds PD1 to PD74 below, where the symbol "bu'" represents a t-butyl group, but the phosphorescent dopant is not limited thereto.

PD1

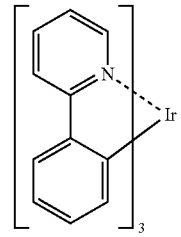

PD2

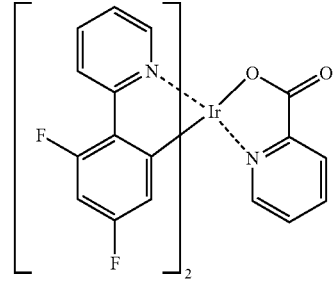

PD3

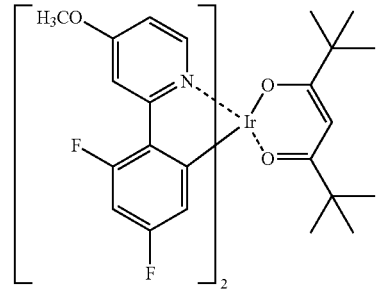

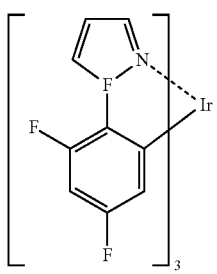
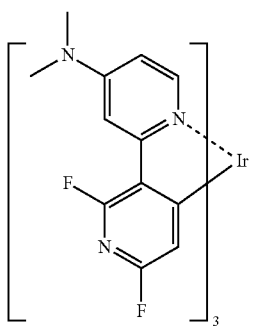
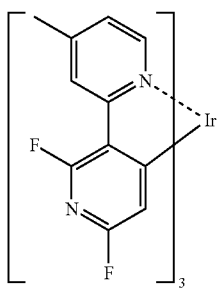
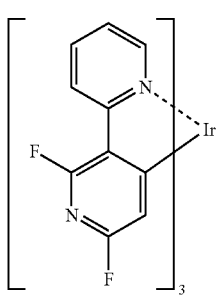
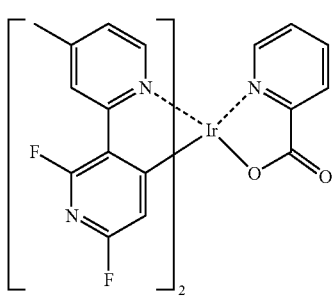
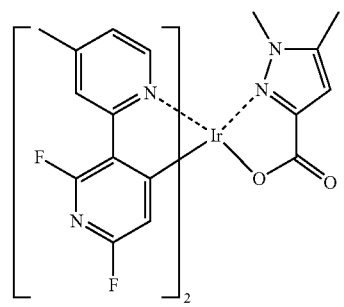
PD4
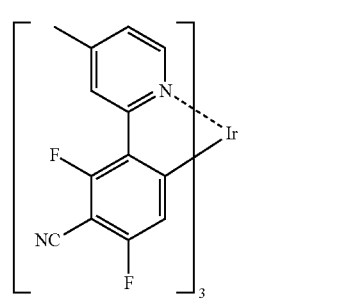
PD5
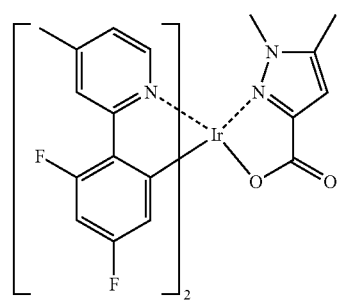
PD6
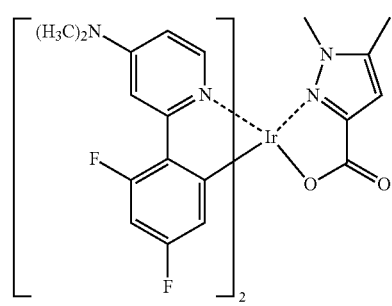
PD7
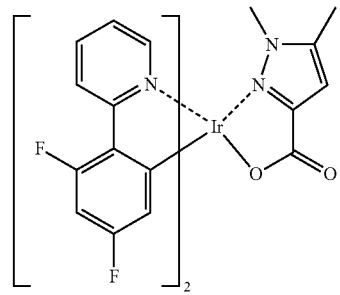
PD8
PD9
PD10
PD11
PD12
PD13

-continued
PD14
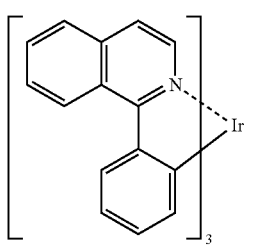
PD15
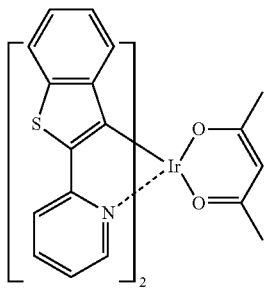
PD16
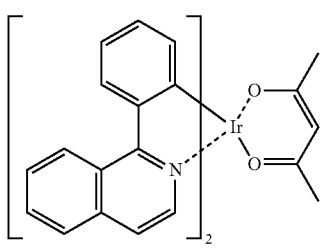
PD17
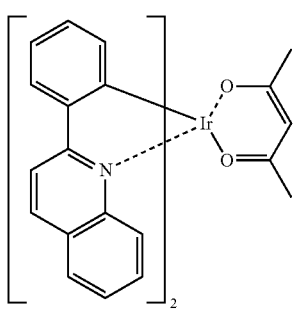
PD18
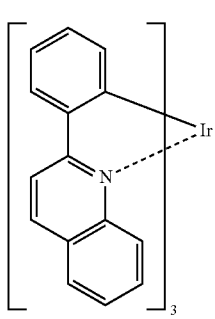
-continued
Pd19
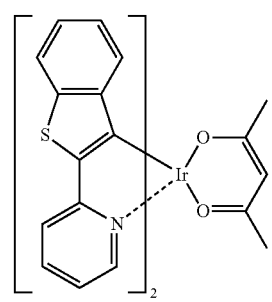
PD20
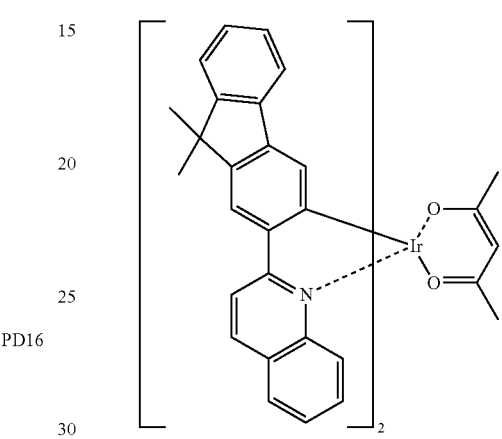
PD21
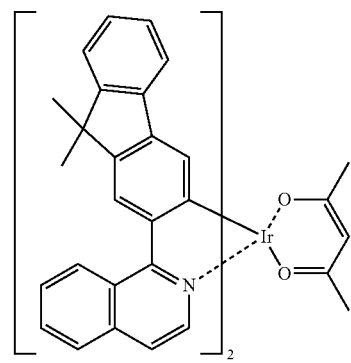
PD22
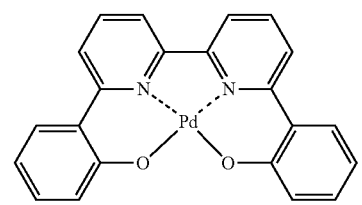
PD23
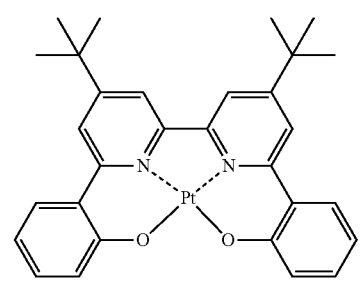

PD24 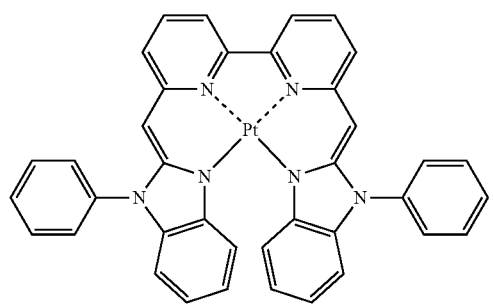
PD25 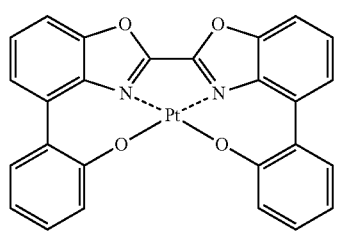
PD26 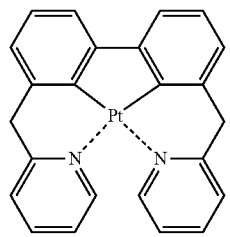
PD27 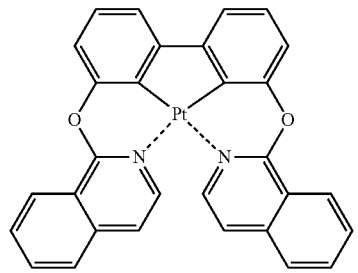
PD28 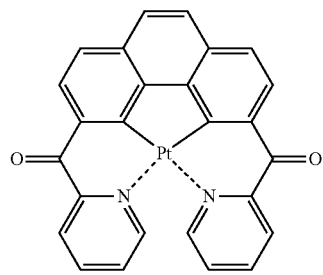
PD29 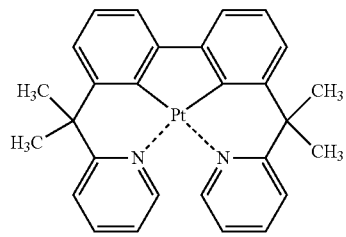
PD30 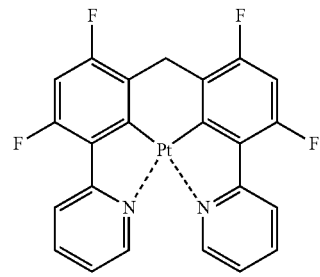
PD31 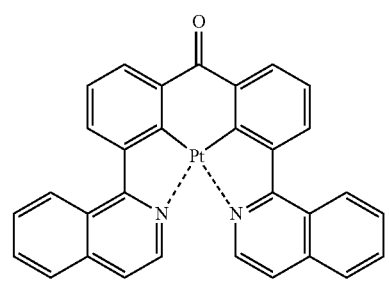
PD32 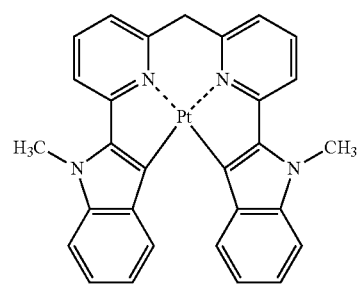
PD33 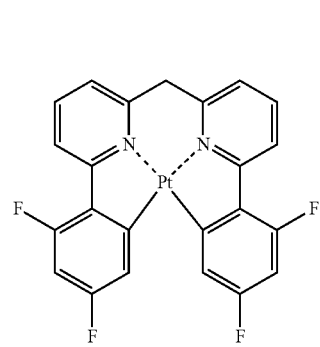
PD34 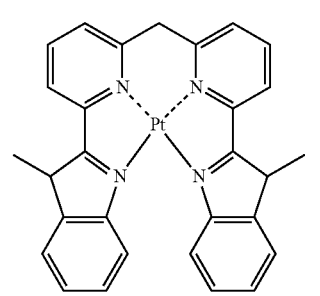

-continued
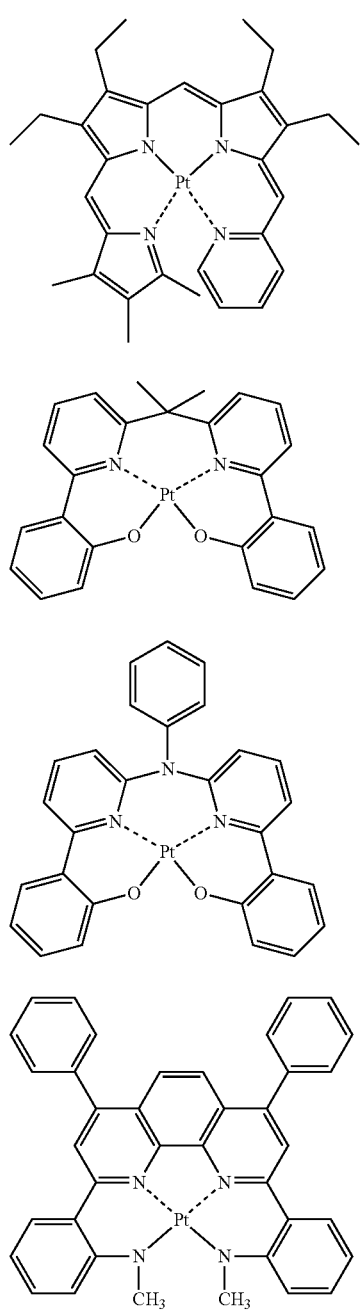
PD35
PD36
PD37
PD38
PD39
-continued
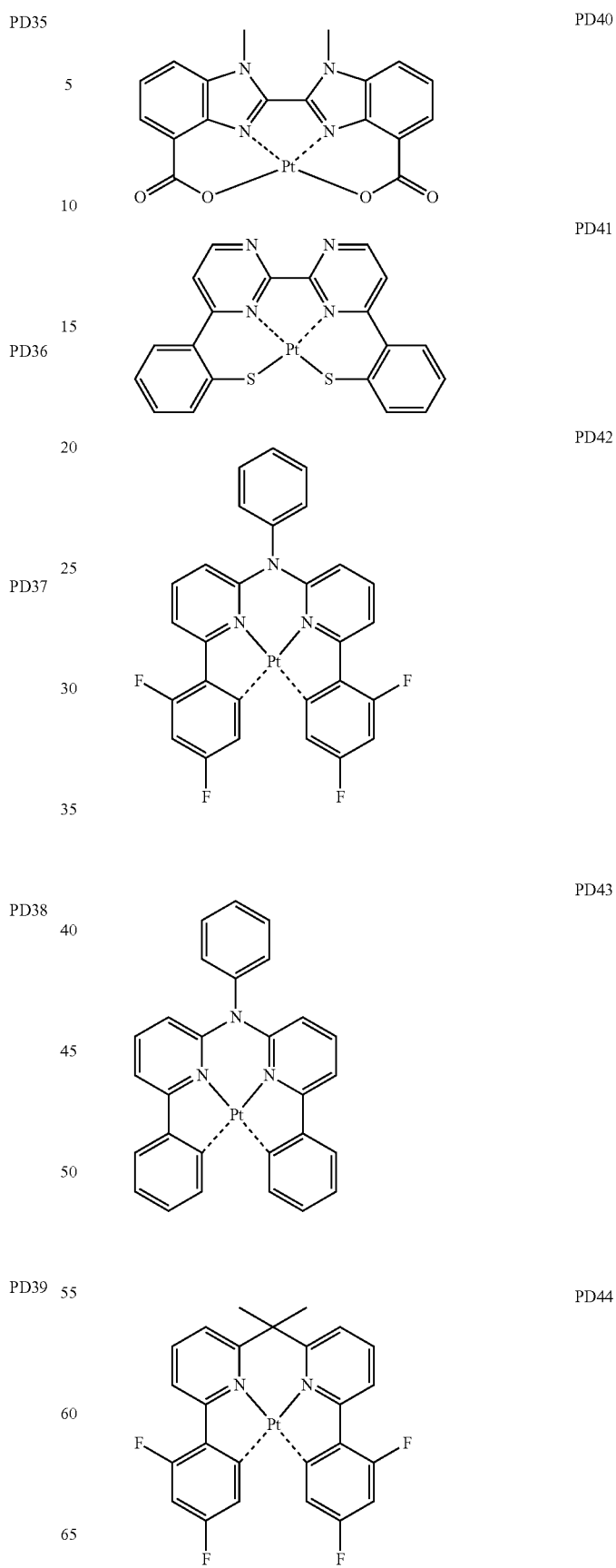
PD40
PD41
PD42
PD43
PD44

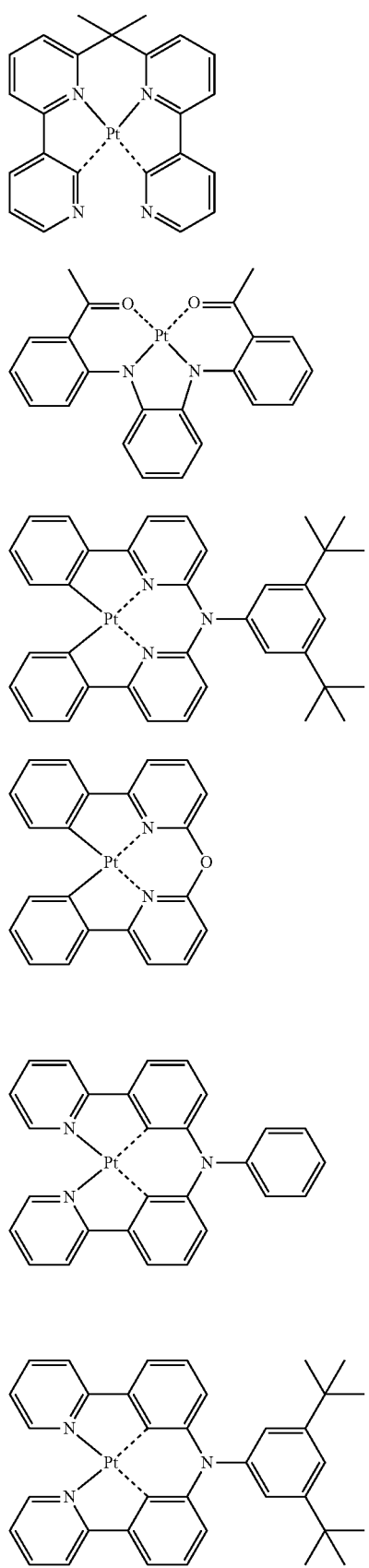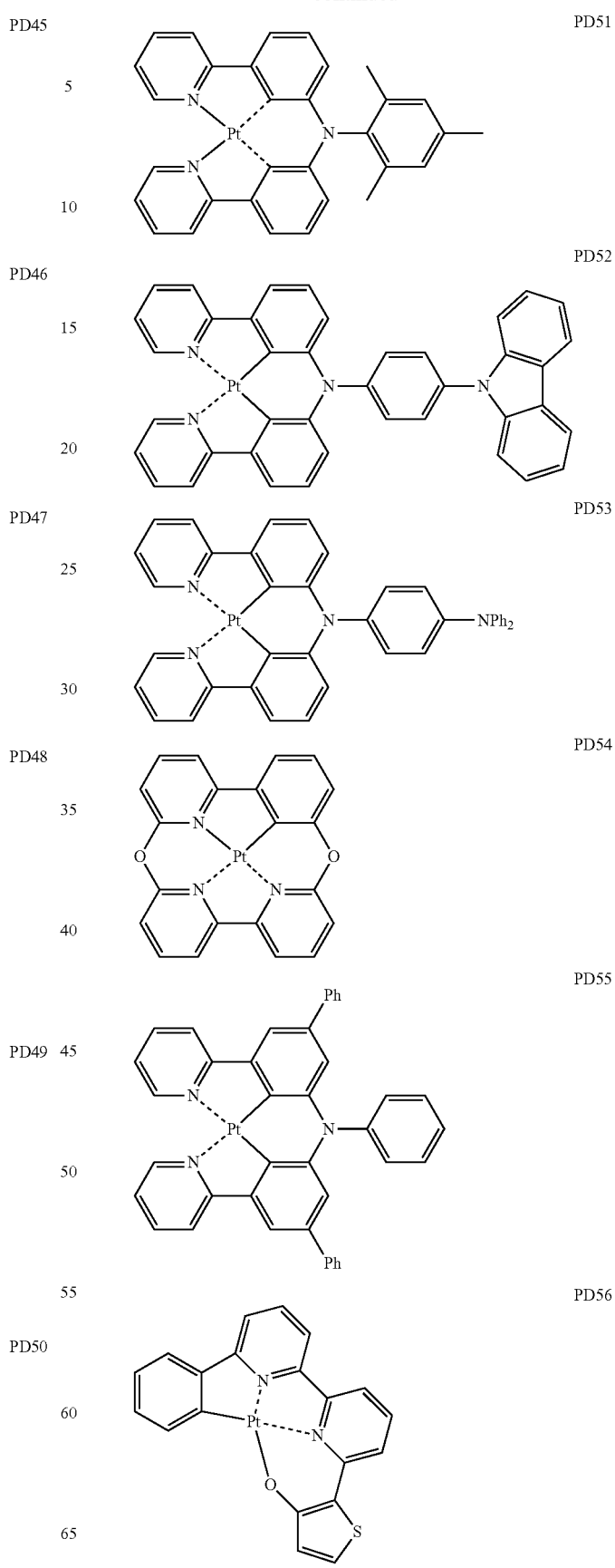

-continued
PD57
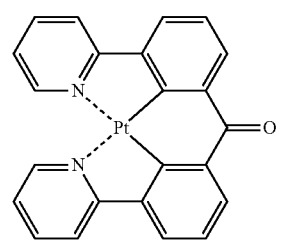
PD58
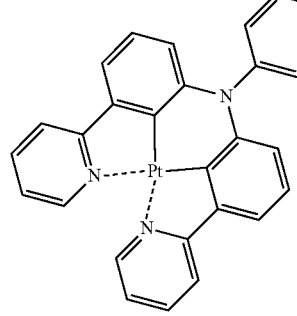
PD59
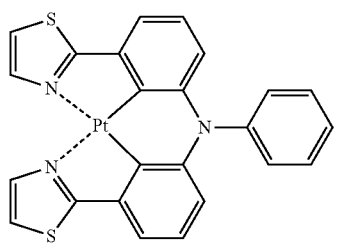
PD60
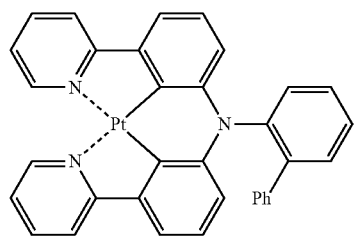
PD61
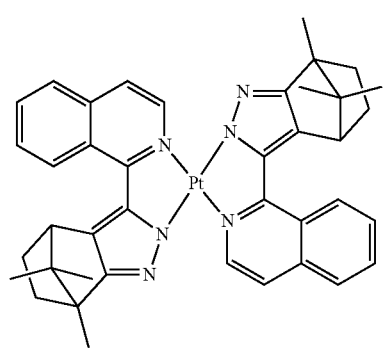
-continued
PD62
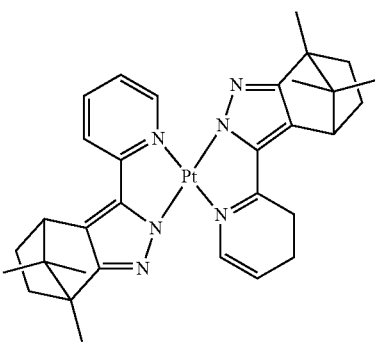
PD63
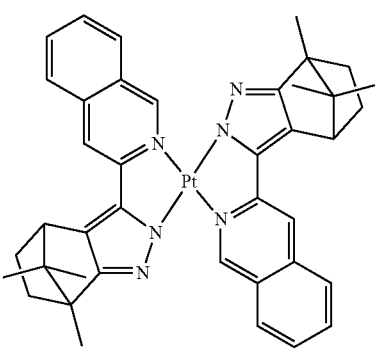
PD64
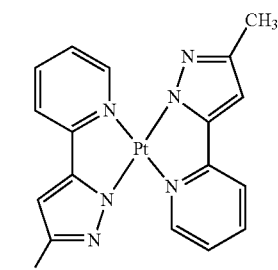
PD65
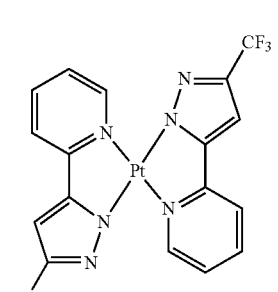
PD66
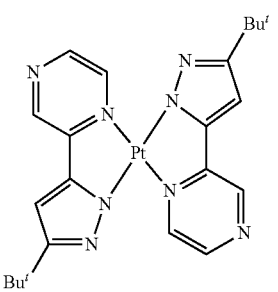

PD67 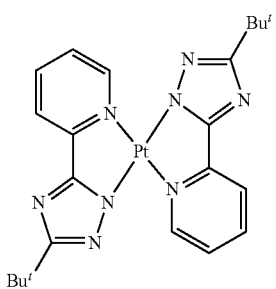
PD68 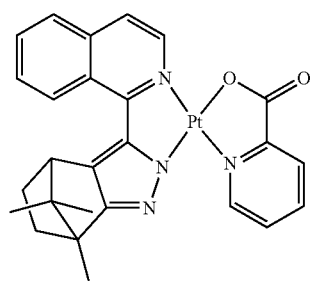
PD69 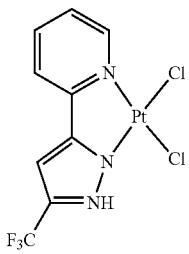
PD70 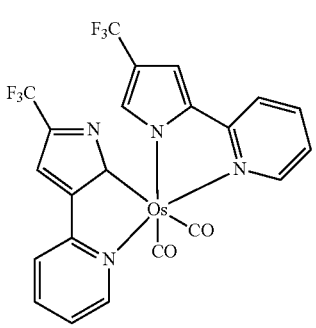
PD71 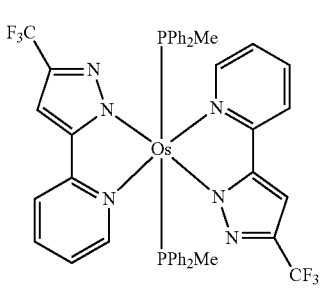
PD72 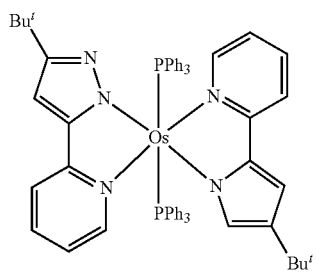
PD73 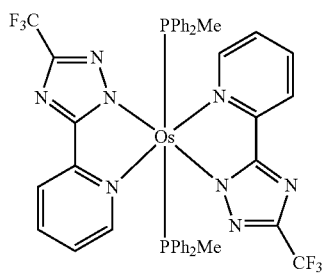
PD74 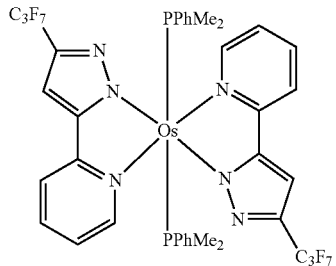
Alternatively, the phosphorescent dopant may include PtOEP below.
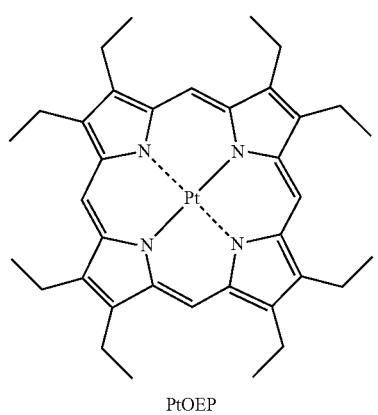
PtOEP
The fluorescent dopant may include at least one selected from DPAVBi, BDAVBi, TBPe, DCM, DCJTB, Coumarin 6, and C545T below.

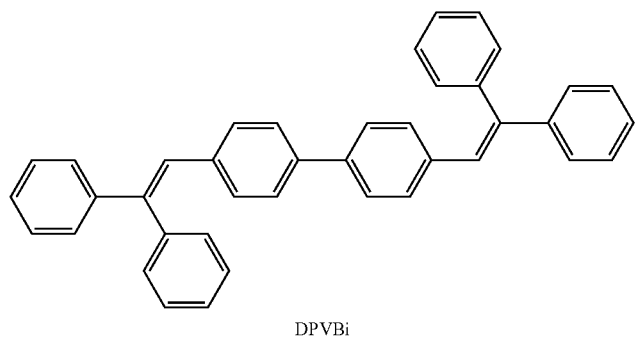
DPVBi
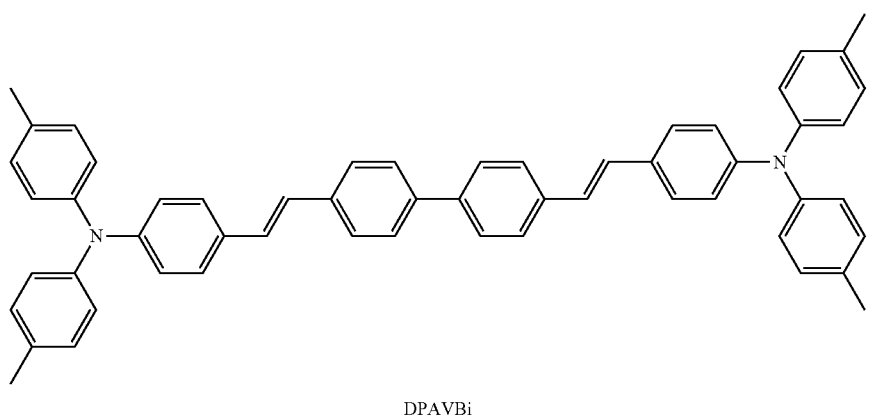
DPAVBi
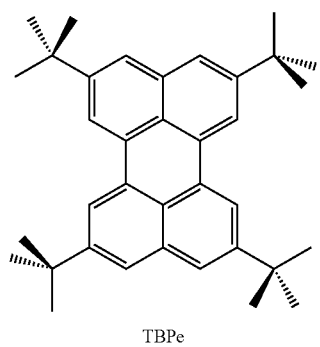
TBPe
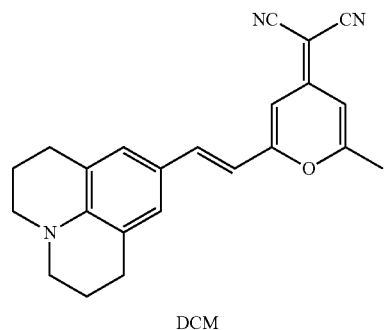
DCM
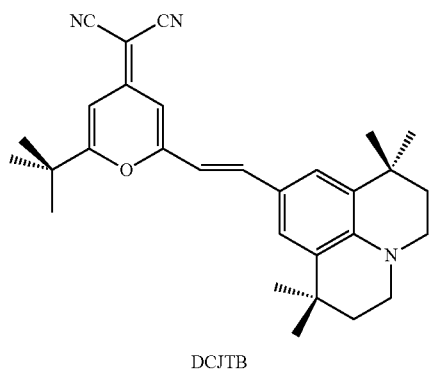
DCJTB
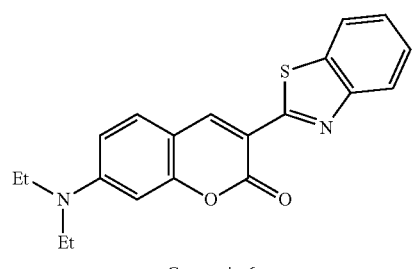
Coumarin 6

-continued

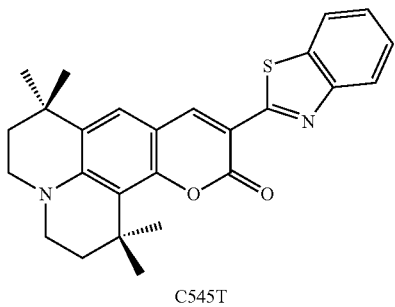

C545T

The fluorescent dopant may include a compound represented by Formula 501:

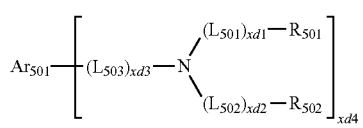

Formula 501

In Formula 501, $Ar_{501}$ may be selected from a naphthalene, a heptalene, a fluorenene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) ($Q_{501}$ to $Q_{503}$ are each independently selected from a hydrogen, $C_1$-$C_{60}$ alkyl group, a $C_2$-$C_{60}$ alkenyl group, a $C_6$-$C_{60}$ aryl group, and a $C_1$-$C_{60}$ heteroaryl group);

descriptions of $L_{501}$ to $L_{503}$ may be each independently as referred to in the description provided in connection with $L_{201}$ above (e.g., $L_{501}$ to $L_{503}$ may each independently be substantially the same as described with respect to $L_{201}$);

$R_{501}$ and $R_{502}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group and a dibenzofuranyl group, and a dibenzothiophenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

xd1 to xd3 may be each independently selected from 0, 1, 2, and 3; and xd4 may be selected from 1, 2, 3, and 4.

The fluorescent dopant may include at least one selected from Compounds FD1 to FD9 below.

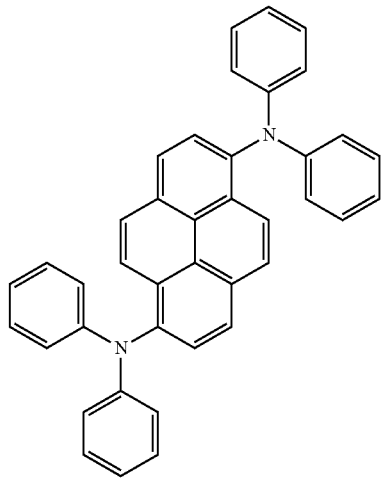

FD1

83
-continued
FD2
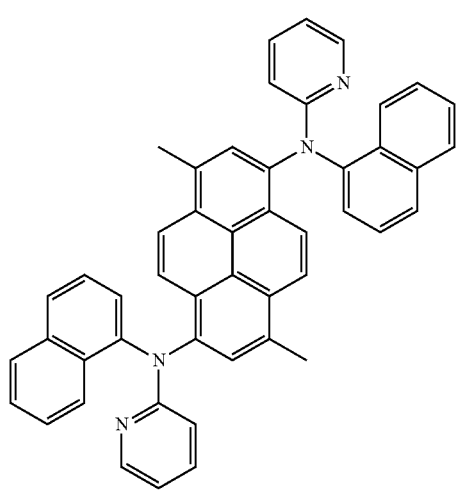
FD3
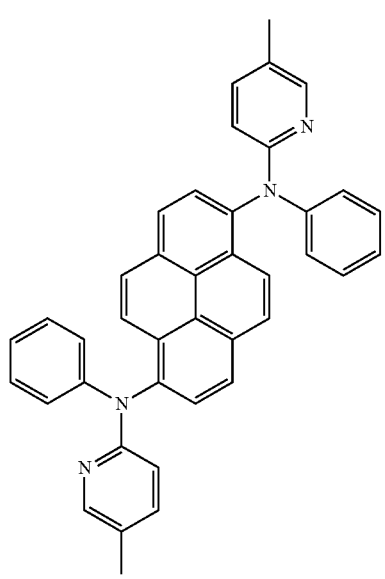
84
-continued
FD4
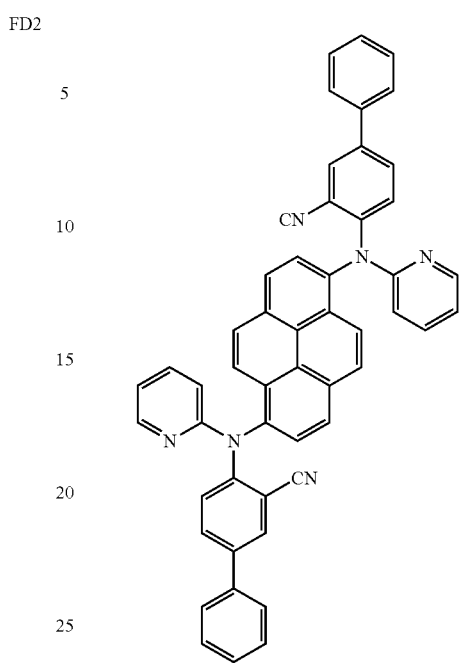
FD5
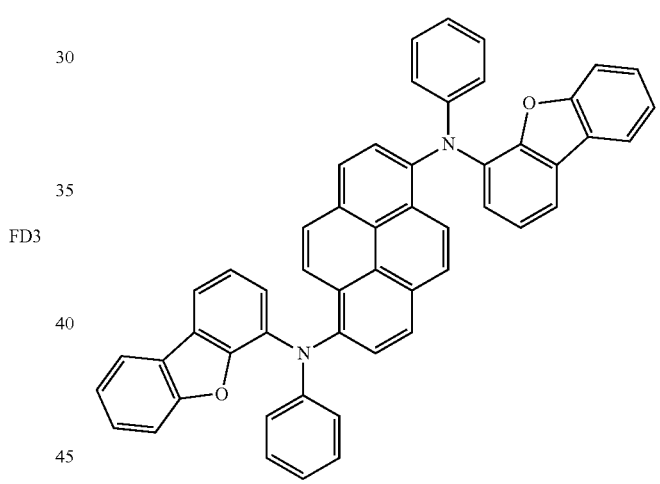
FD6
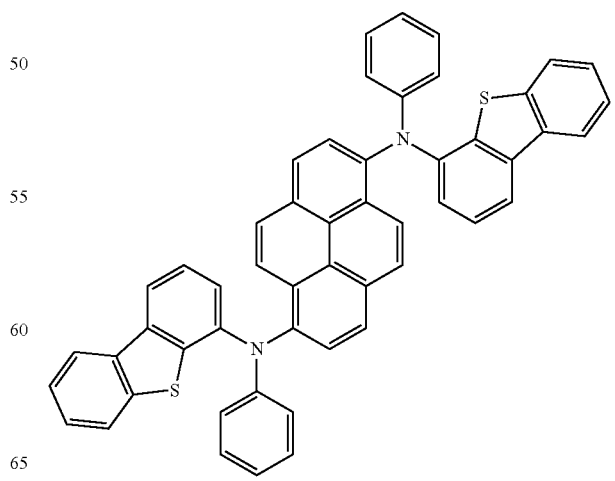

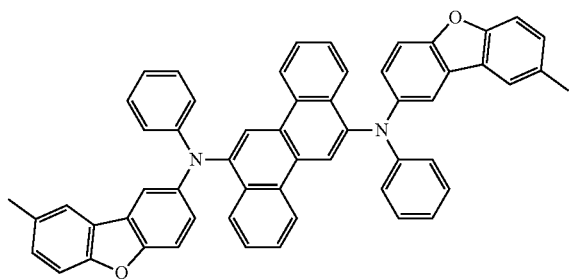

FD7

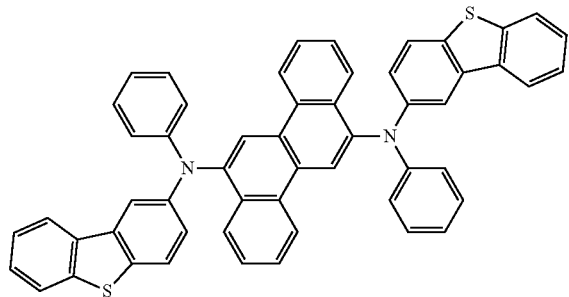

FD8

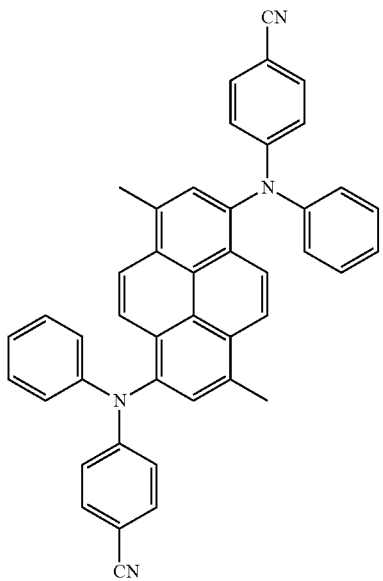

FD9 ers of each structure are sequentially stacked from the first electrode 110 in this stated order, but the electron transport region is not limited thereto.

In an example embodiment, the organic layer 150 of the organic light-emitting device 10 may include the electron transport region disposed between the emission layer and the second electrode 190. The electron transport region may include at least one selected from the ETL and the EIL.

The ETL may include at least one selected from $Alq_3$, Balq, TAZ, and NTAZ below, in addition to BCP and Bphen above.

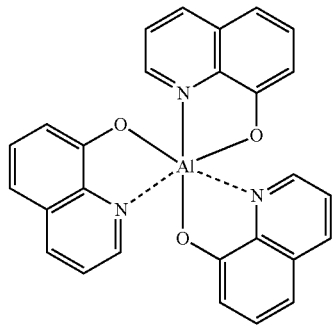

$Alq_3$

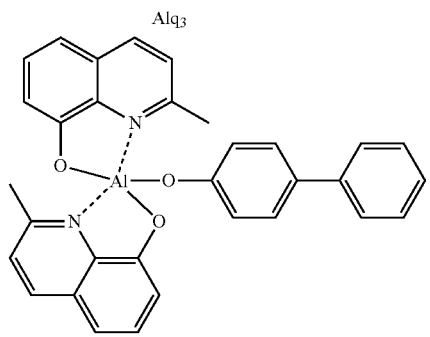

BAlq

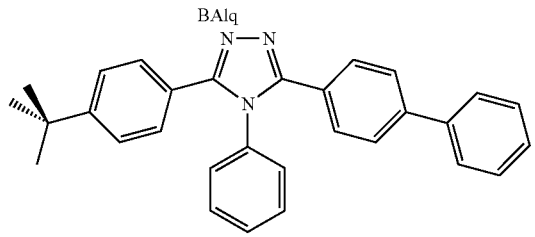

TAZ

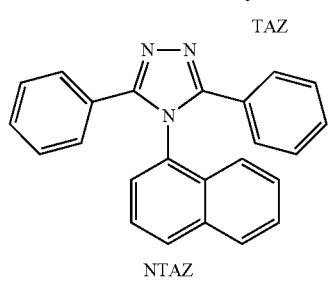

NTAZ

An amount of the dopant included in the emission layer may be, in general, in a range of about 0.01 to about 15 parts by weight based on 100 parts by weight of the host, but it is not limited thereto.

A thickness of the emission layer may be in a range of about 100 Å to about 1,000 Å, for example, about 200 Å to about 600 Å. In one example embodiment, when the thickness of the emission layer is within the ranges described above, excellent light-emission characteristics are obtained without a substantial increase in driving voltage.

Next, the electron transport region may be disposed on the emission layer.

The electron transport region may include at least one selected from an HBL, an ETL, and an EIL, but the electron transport region is not limited thereto.

For example, the electron transport region may have a structure of ETL/EIL or a structure of HBL/ETL/EIL. Layers Alternatively, the ETL may include at least one compound selected from a compound represented by Formula 601 below and a compound represented by Formula 602 below:

$$Ar_{601}\text{-}[(L_{601})_{xe1}\text{-}E_{601}]_{xe2} \quad \text{Formula 601}$$

In Formula 601, $Ar_{601}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) ($Q_{301}$ to $Q_{303}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

a description of $L_{601}$ may be as referred to in the description provided in connection with $L_{201}$ above (e.g., $L_{601}$ may be substantially the same as described with respect to $L_{201}$);

$E_{601}$ may be selected from a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

xe1 may be selected from 0, 1, 2, and 3; and xe2 may be selected from 1, 2, 3, and 4, and

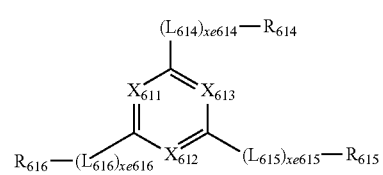

Formula 602 in Formula 602, $X_{611}$ may be N or C-($L_{611}$)$_{xe611}$-$R_{611}$, $X_{612}$ may be N or C-($L_{612}$)$_{xe612}$-$R_{612}$; and $X_{613}$ may be N or C-($L_{613}$)$_{xe613}$-$R_{613}$, wherein at least one of $X_{611}$ to $X_{613}$ is nitrogen;

descriptions of $L_{611}$ to $L_{616}$ may be each independently as referred to in the description provided in connection with $L_{201}$ above (e.g., $L_{611}$ to $L_{616}$ may each independently be substantially the same as described with respect to $L_{201}$);

$R_{611}$ to $R_{616}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 may be each independently selected from 0, 1, 2, and 3.

The compound represented by Formula 601 and the compound represented by Formula 602 may each independently include at least one selected from Compounds ET1 to ET15 below.

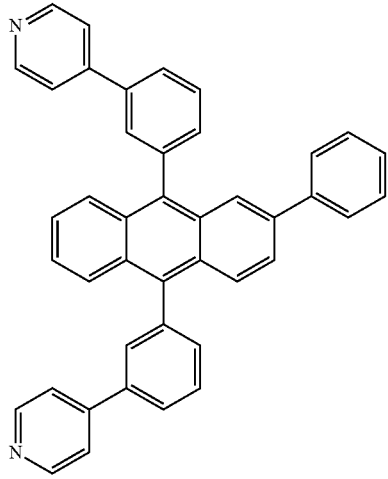

ET3

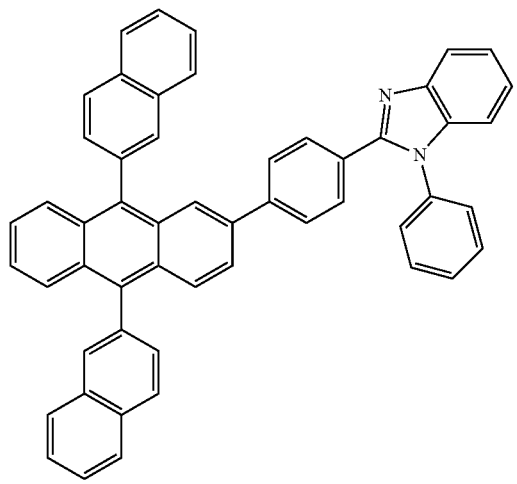

ET1

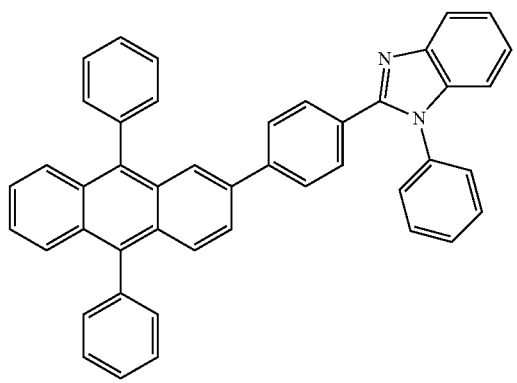

ET4

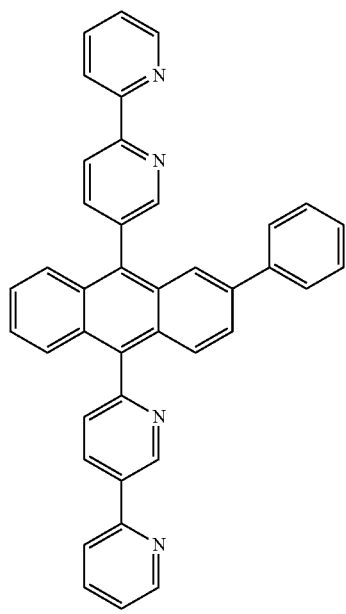

ET2

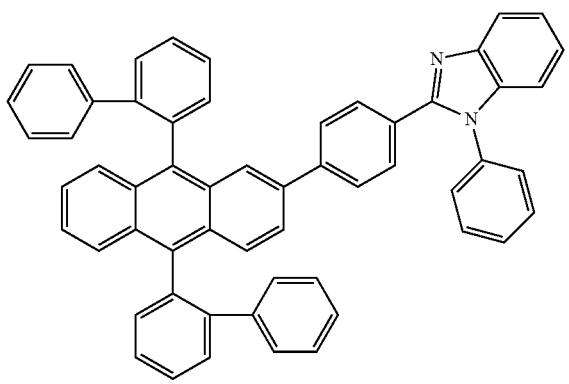

ET5

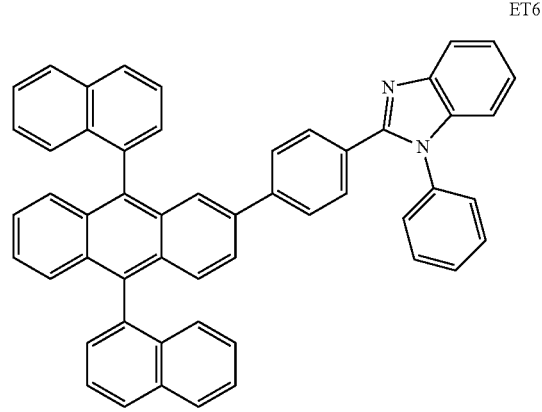

ET11

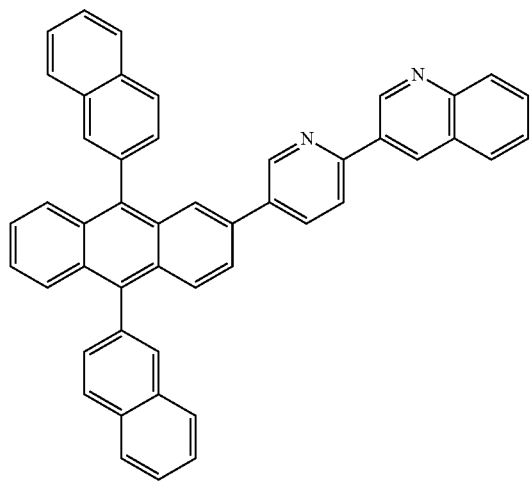

ET12

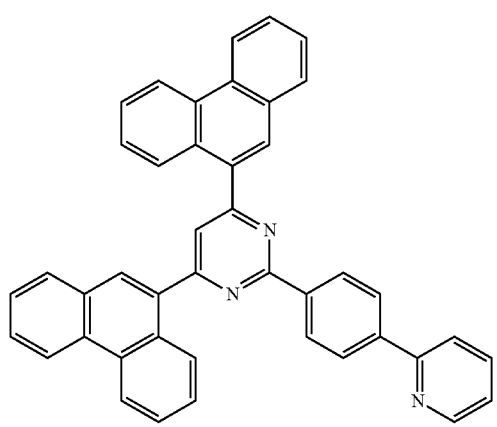

ET13

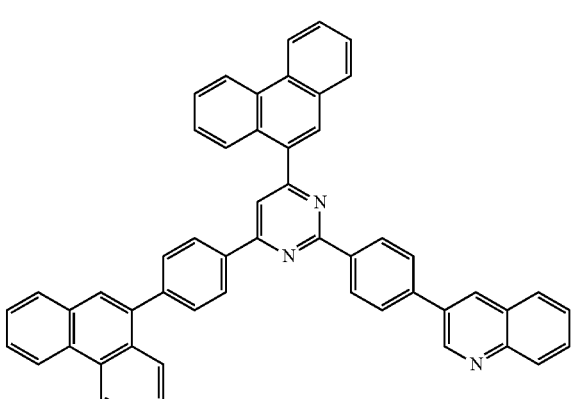

ET14

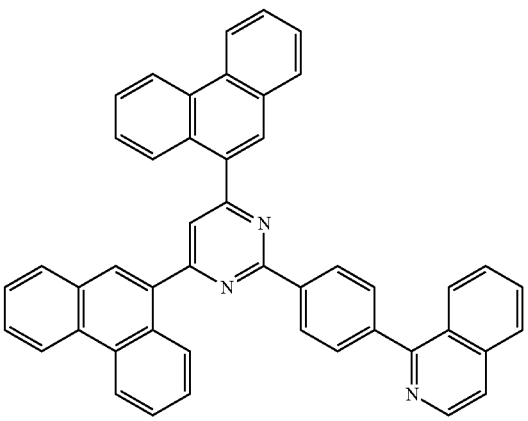

ET15

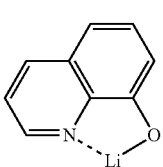

A thickness of the ETL may be in a range of about 100 Å to about 1,000 Å, for example, about 150 Å to about 500 Å. In one example embodiment, when the thickness of the ETL is within the ranges described above, the ETL has satisfactory or suitable electron transport characteristics without a substantial increase in driving voltage.

The ETL may further include, in addition to the materials described above, a metal-containing material.

The metal-containing material may include a Li complex. The Li complex may include, for example, Compound ET-D1 (lithium Quinolate, LiQ) or ET-D2 below.

ET-D1

ET-D2

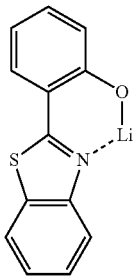

The electron transport region may include an HBL. When the emission layer includes a phosphorescent dopant, the HBL may reduce or prevent diffusion of triplet excitons or holes into the ETL from the emission layer.

When the electron transport region includes an HBL, the HBL may be formed on the emission layer by utilizing various suitable methods, such as vacuum deposition, spin coating, casting, an LB method, an ink-jet printing, a laser-printing, or an LITI method. When the HBL is formed by vacuum deposition and/or spin coating, the deposition and coating conditions for the HBL may be determined by referring to the deposition and coating conditions for the HIL.

The HBL may include, for example, at least one selected from BCP and Bphen, but it is not limited thereto.

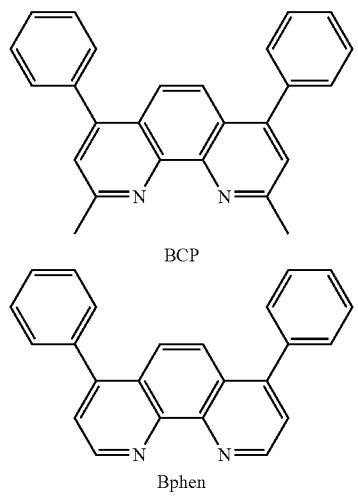

BCP

Bphen

A thickness of the HBL may be in a range of about 20 Å to about 1,000 Å, for example, about 30 Å to about 300 Å. In one example embodiment, when the thickness of the HBL is within the ranges described above, excellent hole blocking characteristics are obtained without a substantial increase in driving voltage.

The ETL may be formed on the emission layer or on the HBL by utilizing various suitable methods, such as vacuum deposition, spin coating, casting, an LB method, an ink-jet printing, a laser-printing, or an LITI method. When the ETL formed by vacuum deposition and/or spin coating, the deposition and coating conditions for the ETL may be determined by referring to the deposition and coating conditions for the HIL.

The electron transport region may include an EIL that facilitates electron injection from the second electrode 190.

The EIL may be formed on the ETL by utilizing various suitable methods, such as vacuum deposition, spin coating, casting, an LB method, an ink-jet printing, a laser-printing, or an LITI method. When the EIL is formed by vacuum deposition and/or spin coating, the deposition and coating conditions for the EIL may be determined by referring to the deposition and coating conditions for the HIL.

The EIL may include at least one selected from LiF, NaCl, CsF, $Li_2O$, BaO, and LiQ.

A thickness of the EIL may be in a range of about 1 Å to about 100 Å, for example, about 3 Å to about 90 Å. In one example embodiment, when the thickness of the EIL is within the ranges described above, the EIL has satisfactory or suitable electron injection characteristics without a substantial increase in driving voltage.

The second electrode 190 is disposed on the organic layer 150. The second electrode 190 may be a cathode that is an electron injection electrode. Here, a material for forming the second electrode 190 may be selected from a metal, an alloy, an electrically conductive compound, and a mixture thereof, which has a relatively low work function. Non-limiting examples of the material for forming the second electrode 190 are lithium (Li), magnesium (Mg), aluminum (Al), aluminum-lithium (Al—Li), calcium (Ca), magnesium-indium (Mg—In), magnesium-silver (Mg—Ag). Alternatively, the material for forming the second electrode 190 may be ITO or IZO. The second electrode 190 may be a reflective electrode, a semi-reflective electrode, or a transparent electrode.

In addition, the organic layer 150 of the organic light-emitting device 10 may be formed by a deposition method using compounds according to an example embodiment, or by a wet coating method using compounds that are prepared in solutions according to an example embodiment.

The organic light-emitting device 10 according to an example embodiment may be included in various suitable types or kinds of flat panel display apparatus, such as a passive matrix OLED display apparatus and an active matrix OLED display apparatus.

For example, when the organic light-emitting device 10 is equipped with the active matrix OLED display apparatus, the first electrode 110 may be disposed on a side of the substrate, and as a pixel electrode, the first electrode 110 may be electrically coupled to source and drain electrodes of a thin film transistor. In addition, the organic light-emitting device 10 may be equipped with a flat panel display apparatus that can display screens at both sides.

Hereinbefore, the organic light-emitting device 10 has been described with reference to FIG. 1, but it is not limited thereto.

The term "a $C_1$-$C_{60}$ alkyl group" used herein refers to a linear or branched aliphatic hydrocarbon monovalent group having 1 to 60 carbon atoms, and non-limiting examples thereof include a methyl group, an ethyl group, a propyl group, an isobutyl group, a sec-butyl group, a ter-butyl group, a pentyl group, an iso-amyl group, and a hexyl group. The term "a $C_1$-$C_{60}$ alkylene group" used herein refers to a divalent group having substantially the same structure as that of the $C_1$-$C_{60}$ alkyl group.

The term "a $C_1$-$C_{60}$ alkoxy group" used herein refers to a monovalent group represented by —$OA_{101}$ ($A_{101}$ is the $C_1$-$C_{60}$ alkyl group), and non-limiting examples thereof include a methoxy group, an ethoxy group, and an isopropyloxy group.

The term "a $C_2$-$C_{60}$ alkenyl group" used herein refers to a hydrocarbon group having at least one carbon double bond in the main chain (e.g., the middle) or at the terminal position of the $C_2$-$C_{60}$ alkyl group, and non-limiting examples thereof include an ethenyl group, a prophenyl group, and a butenyl group. The term "a $C_2$-$C_{60}$ alkenylene group" used herein refers to a divalent group having substantially the same structure as that of the $C_2$-$C_{60}$ alkenyl group.

The term "a $C_2$-$C_{60}$ alkynyl group" used herein refers to a hydrocarbon group having at least one carbon triple bond in the main chain (e.g., the middle) or at the terminal position of the $C_2$-$C_{60}$ alkyl group, and non-limiting examples thereof include an ethynyl group and a propynyl group. The term "a $C_2$-$C_{60}$ alkynylene group" used herein refers to a divalent group having substantially the same structure as that of the $C_2$-$C_{60}$ alkynyl group.

The term "a $C_3$-$C_{10}$ cycloalkyl group" used herein refers to a saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "a $C_3$-$C_{10}$ cycloalkylene group" used herein refers to a divalent group having substantially the same structure as that of the $C_3$-$C_{10}$ cycloalkyl group.

The term "a $C_1$-$C_{10}$ heterocycloalkyl group" used herein refers to a monovalent monocyclic group having at least one heteroatom selected from N, O, P, and S as a ring-forming atom and 1 to 10 carbon atoms, and non-limiting examples thereof include a tetrahydrofuranyl group and a tetrahydrothiophenyl group. The term "a $C_1$-$C_{10}$ heterocycloalkylene group" used herein refers to a divalent group having substantially the same structure as that of the $C_1$-$C_{10}$ heterocycloalkyl group.

The term "a $C_3$-$C_{10}$ cycloalkenyl group" used herein refers to a monovalent monocyclic group that has 3 to 10 carbon atoms and at least one double bond in the ring thereof and does not have aromaticity (e.g., is not aromatic), and non-limiting examples thereof include a cyclopentenyl group, a cyclohexenyl group, and a cycloheptenyl group. The term "a $C_3$-$C_{10}$ cycloalkenylene group" used herein refers to a divalent group having substantially the same structure as that of the $C_3$-$C_{10}$ cycloalkenyl group.

The term "a $C_1$-$C_{10}$ heterocycloalkenyl group" used herein refers to a monovalent monocyclic group that has at least one hetero atom selected from N, O, P, and S as a ring-forming atom, 1 to 10 carbon atoms, and at least one double bond in the ring thereof. Non-limiting examples of the $C_1$-$C_{10}$ heterocycloalkenyl group include a $C_2$-$C_{10}$ heterocycloalkenyl group a 2,3-hydrofuranyl group and a 2,3-hydrothiophenyl group. The term "a $C_1$-$C_{10}$ heterocycloalkenylene group" used herein refers to a divalent group having substantially the same structure as that of the $C_1$-$C_{10}$ heterocycloalkenyl group.

The term "a $C_6$-$C_{60}$ aryl group" used herein refers to a monovalent group having a carbocyclic aromatic system having 6 to 60 carbon atoms, and the term "a $C_6$-$C_{60}$ arylene group" used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include 2 or more rings, the rings may be fused to each other.

The term "a $C_1$-$C_{60}$ heteroaryl group" used herein refers to a monovalent group having a carbocyclic aromatic system that has at least one hetero atom selected from N, O, P, and S as a ring-forming atom, and 1 to 60 carbon atoms. The term "a $C_1$-$C_{60}$ heteroarylene group" used herein refers to a divalent group having a carbocyclic aromatic system that has at least one hetero atom selected from N, O, P, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include 2 or more rings, the rings may be fused to each other.

The term "a $C_6$-$C_{60}$ aryloxy group" used herein refers to a group represented by —$OA_{102}$ ($A_{102}$ is the $C_6$-$C_{60}$ aryl group), and the term "a $C_6$-$C_{60}$ arylthio group" used herein refers to a group represented by —$SA_{103}$ ($A_{103}$ is the $C_6$-$C_{60}$ aryl group).

The term "a monovalent non-aromatic condensed polycyclic group" used herein refers to a monovalent group (having 8 to 60 carbon atoms) that has 2 or more rings condensed to each other, carbon atoms as the only ring forming atoms, and non-aromaticity in the entire molecular structure (e.g., the entire molecular structure is not aromatic). A non-limiting example of the monovalent non-aromatic condensed polycyclic group is a fluorenyl group. The term "a divalent non-aromatic condensed polycyclic group" used herein refers to a divalent group having substantially the same structure as that of the monovalent non-aromatic condensed polycyclic group.

The term "a monovalent non-aromatic condensed heteropolycyclic group" used herein refers to a monovalent group (having 2 to 60 carbon atoms) that has 2 or more rings condensed to each other, has a heteroatom other than carbon atom selected from N, O, P, and S as a ring forming atom, and has non-aromaticity in the entire molecular structure (e.g., the entire molecular structure is not aromatic). A non-limiting example of the monovalent non-aromatic condensed heteropolycyclic group is a carbazolyl group. The term "a divalent non-aromatic condensed heteropolycyclic group" used herein refers to a divalent group having substantially the same structure as that of the monovalent non-aromatic condensed heteropolycyclic group.

The term "a $C_6$-$C_{60}$ arene" used herein refers to an aromatic ring having 6 to 60 carbon atoms, and non-limiting examples thereof are a benzene, a naphthalene, an anthracene, a phenanthrene, a pyrene, and a chrysene. When the $C_6$-$C_{60}$ arene includes 2 or more rings, the rings may be fused to each other. Further, as disclosed herein the $C_6$-$C_{60}$ arene may be fused with the 1,5-diazocine core (e.g., the central 8-membered ring) of Formula 1, and the $C_6$-$C_{60}$ arene may be bonded to $R_{13}$ or $R_{14}$. For example, two carbon atoms may be shared between the $C_6$-$C_{60}$ arene and the 1,5-diazocine core of Formula 1.

Hereinafter, an organic light-emitting device according to an embodiment will be described in detail with reference to Synthesis Examples and Examples.

EXAMPLE

Synthesis Example 1

Synthesis of Compound 1

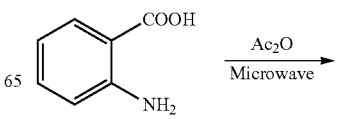

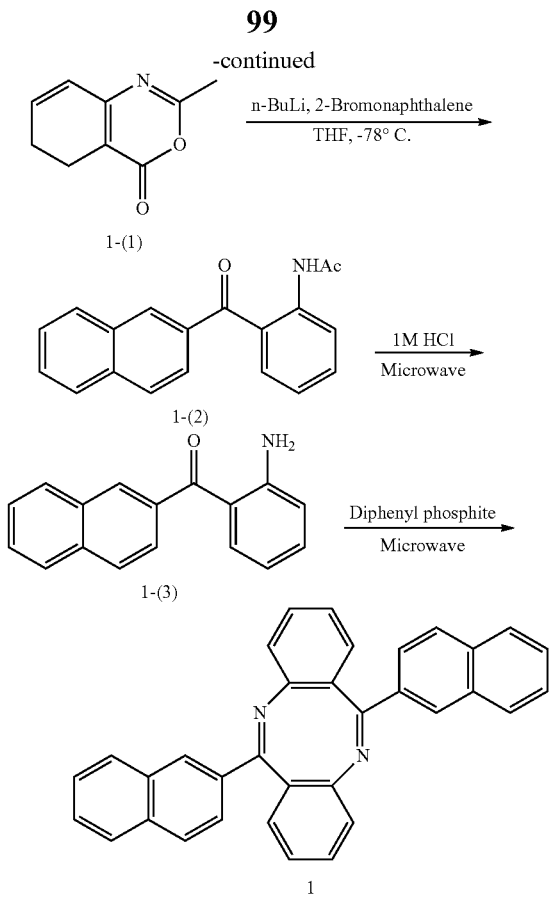

(1) Synthesis of Intermediate 1-(1)

1 g (7.5 mmol, 1 eq) of 2-aminobenzoic acid and 1.53 g (15.02 mmol, 2 eq) of $Ac_2O$ (acetic anhydride) were put in a 10 mL container, and then, irradiated with microwaves (power: 300 W, temperature: 60° C., run time: 5 min, hold time: 20 min). Solids obtained by cooling the reaction mixture were washed with n-hexane, and then, filtered under a reduced pressure. The resulting solids were dried by a vacuum pump, thereby obtaining 5.12 g (yield: 72%) of brown solids, i.e., Intermediate 1-(1).

mp 70-72° C.

$^1$H NMR (300 MHz, DMSO-d6) δ=2.41 (s, 3H), 7.53-7.61 (m, 2H), 7.87-7.93 (m, 1H), 8.05-8.08 (m, 1H).

$^{13}$C NMR (75 MHz, DMSO-d6) δ=20.83, 116.2, 126.0, 127.6, 128.1, 136.6, 145.9, 159.1, 160.0.

(2) Synthesis of Intermediate 1-(2)

1 g (4.82 mmol, 1 eq) of 2-bromonaphthalene and 30 mL of purified THF were put in a 100 mL 1-necked flask, and then, stirred in an argon atmosphere to prepare reaction mixture I. The flask containing the reaction mixture I was placed in a cooling bath (ethyl acetate/liquid nitrogen) to cool to a temperature of −78° C. Then, 2.32 mL (5.76 mmol, 2.5 M in hexane, 1.2 eq) of n-BuLi was added to the flask to prepare a mixed solution. The mixed solution was stirred at a temperature of −78° C. for 30 minutes in an argon atmosphere. Meanwhile, 0.93 g (5.79 mmol, 1.2 eq) of Intermediate 1-(1) and 20 mL of THF were added to a separate 100 mL 1-necked flask, and then, stirred in an argon atmosphere to prepare reaction mixture II. The flask containing the reaction mixture II was placed in a cooling bath (ethyl acetate/liquid nitrogen) to cool to a temperature of −78° C. Then, the mixed solution was slowly added to the flask, and then, stirred for 30 minutes. Here, 30 mL of water was added to the flask, thereby completing the reaction therein. After 20 mL of ethyl acetate was added to the flask, the resultant solution was put in a separatory funnel and washed twice with 50 mL of water each time. An organic layer obtained therefrom was dried with amorphous $MgSO_4$, and then, evaporated under a reduced pressure, so as to remove a solvent. The residuals were subjected to chromatography, thereby obtaining 0.92 (yield: 66%) of white solids, i.e., Intermediate 1-(2).

mp 110-113° C.

$^1$H NMR (300 MHz, $CDCl_3$) δ=2.24 (s, 3H), 7.08-7.13 (m, 1H), 7.57-7.66 (m, 4H), 7.81-7.84 (m, 1H), 7.93 (t, 3H, J1=9.5 Hz, J2=9.0 Hz), 8.17 (d, 1H, J=0.9 Hz), 8.64 (d, 1H, J=8.2 Hz), 10.7 (bs, 1H, D2O exchangeable).

$^{13}$C NMR (300 MHz, CDCl3) δ=25.30, 121.6, 122.1, 125.5, 127.0, 127.8, 128.4, 128.5, 129.4, 131.8, 132.1, 133.5, 134.2, 135.2, 135.8, 140.4, 169.2, 199.6.

(3) Synthesis of Intermediate 1-(3)

0.7 g (2.42 mmol, 1 eq) of Intermediate 1-(2) was dissolved in 4 mL of MeOH in a 10 mL container. 4 mL of 1M HCl was added thereto to prepare a mixed solution, and then, the mixed solution was irradiated with microwaves (power: 300 W, temperature: 110° C., run time: 5 min, hold time: 15 min). After the mixed solution was cooled to room temperature, the resulting mixed solution was put in a separatory funnel and extracted 3 times, each time with 20 mL of dichloromethane. An organic layer obtained therefrom was dried with amorphous $MgSO_4$, and then, evaporated under a reduced pressure, so as to remove a solvent. The residuals were subjected to chromatography for separation (eluent: n-hexane/ethyl acetate=4:1(v/v)), thereby obtaining 0.56 g (yield: 93%) of yellow solids, i.e., Intermediate 1-(3).

mp 105-107° C.

$^1$H NMR (300 MHz, DMSO-d6) δ 6.52 (t, 1H, J1=7.8 Hz, J2=7.1 Hz), 6.89 (d, 2H, J=8.31), 7.12 (bs, 2H, D2O exchangeable), 7.28-7.36 (m, 2H), 7.57-7.70 (m, 3H), 8.00-8.12 (m, 4H).

$^{13}$C NMR (75 MHz, DMSO-d6) δ 114.2, 116.6, 116.8, 125.3, 126.7, 127.6, 127.7, 127.8, 129.0, 131.8, 133.8, 134.1, 137.2, 151.8, 197.7.

(4) Synthesis of Compound 1

0.3 g (1.21 mmol, 1 eq) of Intermediate 1-(3) was dissolved in 0.27 mL (1.21 mmol, 1 eq) of diphenyl phosphite in a 10 mL container, and then, irradiated with microwaves (power: 300 W, temperature: 110° C., run time: 5 min, hold time: 20 min). Solids obtained by cooling the reaction mixture to room temperature were dissolved in 5 mL of $CH_2Cl_2$. After an organic layer obtained therefrom was washed 3 times, each time with 100 mL of water, dried with amorphous $MgSO_4$, and then, evaporated under a reduce pressure, so as to remove a solvent. The residuals were subjected to chromatography for separation (eluent: $CH_2CH_2$), thereby obtaining 0.16 g (yield: 60%) of yellow solids, i.e., Compound 1.

mp 215-217° C.

$^1$H NMR (300 MHz, CDCl3) δ 7.02-7.04 (m, 4H), 7.12 (d, 2H, J=7.9 Hz), 7.29-7.46 (m, 6H), 7.69-7.79 (m, 6H), 7.97 (s, 2H), 8.15-8.18 (m, 2H).

$^{13}$C NMR (75 MHz, CDCl3) δ 120.9, 123.4, 125.0, 126.2, 126.8, 127.4, 127.5, 127.9, 129.0, 129.7, 131.2, 132.6, 134.6, 135.3, 152.0, 169.5.

HRMS (m/z): [M]+ calculated for C32H22N2 458.1783. Found: 458.1783.

Synthesis Example 2

Synthesis of Compound 5

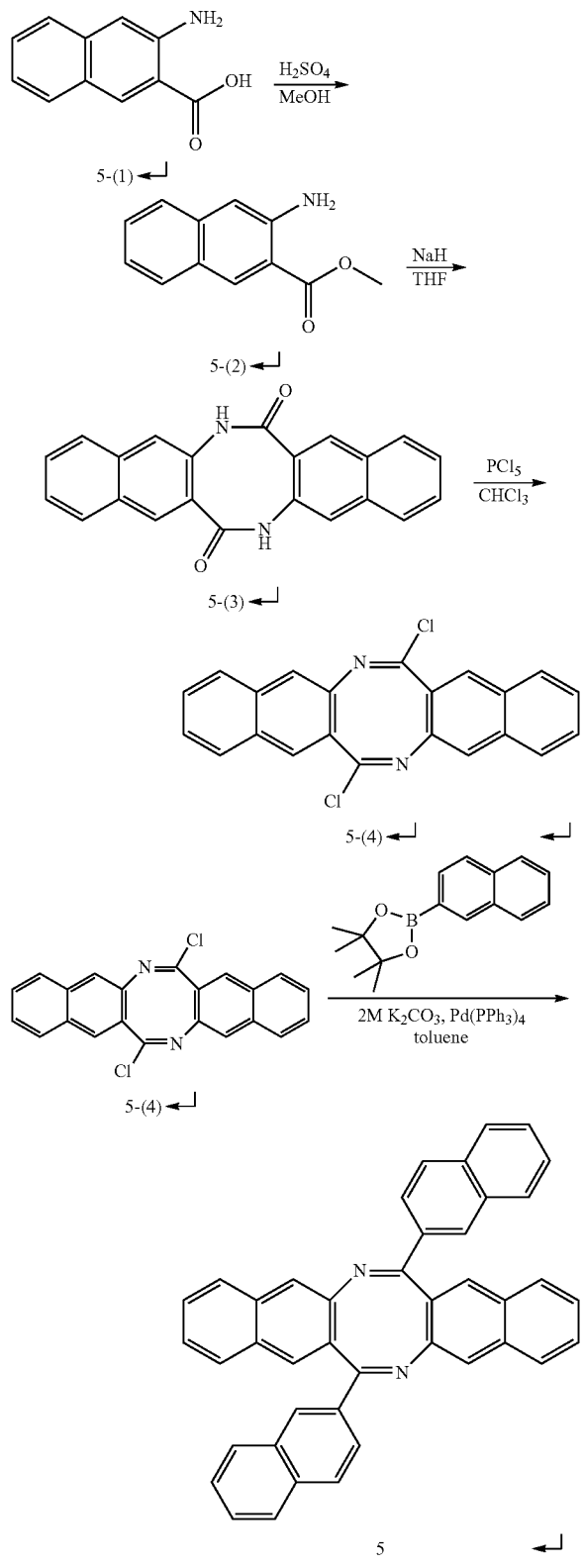

(1) Synthesis of Intermediate 5-(2)

53.2 mL of MeOH was mixed with 5 g (26.7 mmol) of Compound 5-(1), and then, slowly stirred for 1 hour. After the reaction temperature was lowered to a temperature of 0° C., concentrated $H_2SO_4$ was slowly added to the mixed solution, and then, stirred for 30 minutes at the same reaction temperature. The resulting mixed solution was refluxed at a temperature of 80° C. for 7 hours, and then, cooled to room temperature. Afterwards, under a condition where the temperature of a reaction is 0° C., $Na_2CO_3$ was slowly added thereto, so as to adjust the pH of the solution to about 7 to 8. Solid compounds obtained therefrom were filtered through a glass filter, and then dried. The resulting dried solid products were dissolved with ethyl acetate, washed with 190 mL of distilled water, dried with $MgSO_4$, and then, evaporated under a reduced pressure, thereby obtaining 4.34 g (yield: 80%) of white solids, i.e., Compound 5-(2).

$^1$H NMR (300 MHz, CDCl3) 8.5 (s, 1H), 7.80, 7.77 (d, 1H), 7.55, 7.52 (d, 1H), 7.41, 7.39, 7.36 (t, 1H), 7.16, 7.13, 7.11 (t, 1H) 7.05 (s, 1H), 6.41 (s, 2H), 3.88 (s, 3H).

(2) Synthesis of Intermediate 5-(3)

400 mL of tetrahydrofuran was mixed with 10 g (49.7 mmol) of Compound 5-(2), and then, slowly stirred. 3.22 g (134.2 mmol, 60% dispersion in mineral oil) was added thereto, and then, the mixed solution was refluxed at a temperature of 100° C. for 78 hours. After the resulting mixed solution was cooled to room temperature, 250 mL of distilled water was added thereto, so as to complete the reaction. Here, 100 mL of 5N HCl was added thereto, and then, stirred for 30 minutes. Solid compounds obtained therefrom were filtered through a glass filter, and then, washed several times, each time with distilled water. The resulting solid products were vacuum-dried, thereby obtaining 12.59 g (yield: 75%) of Compound 5-(3).

$^1$H NMR (300 MHz, CDCl3) 10.51, 10.50 (d, 2H), 7.94-7.46 (m, 12H)

(3) Synthesis of Intermediate 5-(4)

100 mL of amorphous $HClO_3$ was mixed with 5 g (14.8 mmol) of Compound 5-(3), and then, stirred for 30 minutes in a nitrogen atmosphere. 6.95 g (33.4 mmol) of $PCl_5$ was added thereto, and then, the mixed solution was refluxed for 8 hours at a temperature of 80° C. After the completion of the reaction, the resulting mixed solution was filtered and evaporated under a reduced pressure. Solid products obtained therefrom were washed 3 times, each time with 50 mL of acetone, and then, dried, thereby obtaining 3.37 g (yield: 61%) of Compound 5-(4).

H NMR (300 MHz, CDCl3) 7.96 (s, 2H), 7.91-7.84 (m, 4H), 7.66 (s, 2H), 7.53-7.43 (m, 4H)

(4) Synthesis of Compound 5

2.17 g (5.78 mmol) of Compound (4), 2.94 g (11.57 mmol) of 4,4,5,5-tetramethyl-2-(naphthalene-2-yl)-1,3,2-dioxaborolane, 10 mL of 2M $K_2CO_3$, and 50 mL of toluene were mixed together, and then, the reaction mixture was subjected to out-gassing in a nitrogen atmosphere. Then, 0.8 g (0.7 mmol) of $Pd(PPh_3)_4$ was added thereto, and then, the mixed solution was refluxed at a temperature of 90° C. for 24 hours. After the mixed solution was cooled to room temperature, the resulting mixed solution was extracted with ethyl acetate, washed with distilled water, dried with $MgSO_4$, and then, evaporated under a reduced pressure. The residuals were subjected to chromatography for separation (eluent: hexane:ethyl acetate=10:1(v/v)), thereby obtaining 2.60 g (yield: 64%) of the final product, i.e., Compound 5.

¹H NMR (300 MHz, CDCl3) 8.33-7.90 (m, 10H), 7.70-7.67 (m, 8H), 7.30-7.32 (m, 8H)

Example 1

As a front anode substrate, a glass substrate on which ITO/Ag/ITO was formed was sonicated by using isopropyl alcohol and pure water each for 5 minutes, and cleaned by the exposure to UV ozone. Then, the glass substrate was equipped with a vacuum deposition apparatus.

HT-D1 was deposited on the anode to form a hole injection layer having a thickness of 100 Å. HT3 was deposited on the hole injection layer to form a hole transport layer having a thickness of 1,100 Å. Compound 2 (host) and FD9 (dopant) were co-deposited on the hole transport layer at a weight ratio of 200:3 to form an emission layer having a thickness of 200 Å. Afterwards, ET1 and LiQ were co-deposited on the emission layer at a weight ratio of 50:50 to form an electron transport layer having a thickness of 360 Å. LiQ was deposited on the electron transport layer to form an electron injection layer having a thickness of 10 Å, and then, Mg and Ag were deposited on the electron injection layer at a weight ratio of 110:10 to form a cathode having a thickness of 110 Å, thereby manufacturing a top-emission organic light-emitting device.

Example 2

An organic light-emitting device was manufactured in the same manner as in Example 1, except that in forming the emission layer Compound 4 was used instead of Compound 2.

Example 3

An organic light-emitting device was manufactured in the same manner as in Example 1, except that in forming the emission layer Compound 6 was used instead of Compound 2.

Example 4

An organic light-emitting device was manufactured in the same manner as in Example 1, except that in forming the emission layer Compound 8 was used instead of Compound 2.

Comparative Example

An organic light-emitting device was manufactured in the same manner as in Example 1, except that in forming the emission layer ADN was used instead of Compound 2.

Evaluation Example 1

Driving voltages, current densities, efficiencies, and color coordinates of the organic light-emitting devices prepared in Examples 1 to 4 were evaluated by using a current-voltmeter (Keithley SMU 236) and a luminance meter PR650, and the results are shown in Table 1 below:

TABLE 1

| | Emission layer host | Driving voltage (V) | Current density (mA/cm²) | Efficiency (cd/A) | CIE color coordinates | |
|---|---|---|---|---|---|---|
| | | | | | CIE_x | |
| Example 1 | Compound 2 | 4.6 | 10.4 | 3.3 | 0.137 | 0.070 |
| Example 2 | Compound 4 | 4.9 | 9.9 | 4.0 | 0.125 | 0.087 |
| Example 3 | Compound 6 | 5.1 | 13.6 | 3.5 | 0.130 | 0.075 |
| Example 4 | Compound 8 | 5.3 | 13.3 | 3.9 | 0.136 | 0.080 |
| Comparative Example | ADN | 4.6 | 10.8 | 2.8 | 0.133 | 0.068 |

Referring to Table 1, it was confirmed that the organic light-emitting devices of Examples 1 to 4 had excellent technical features, as compared to those of the organic light-emitting device of Comparative Example.

Figure 2:
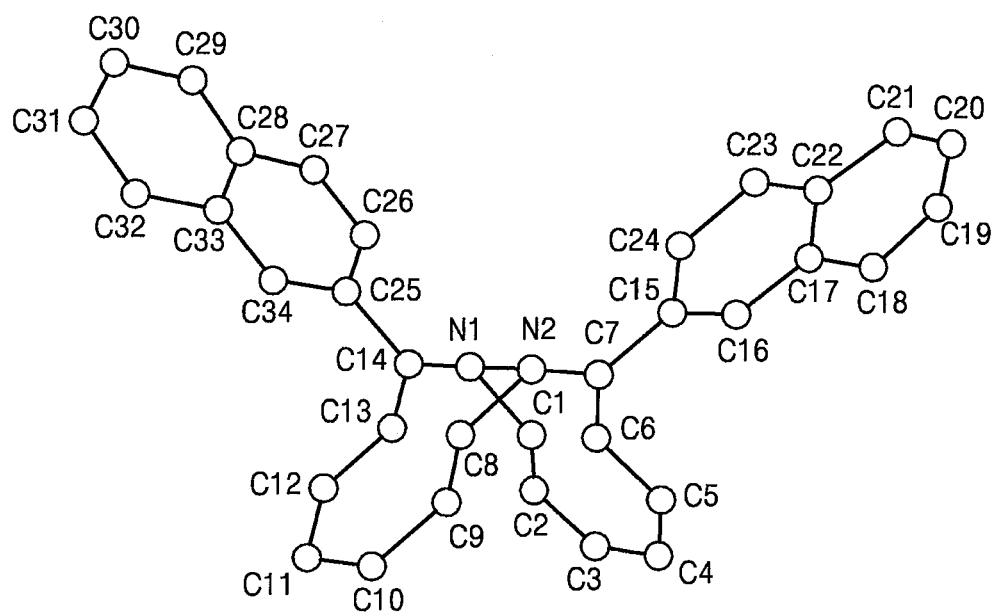
FIG. 2 illustrates a crystal structure of Compound 1.
Figure 3:
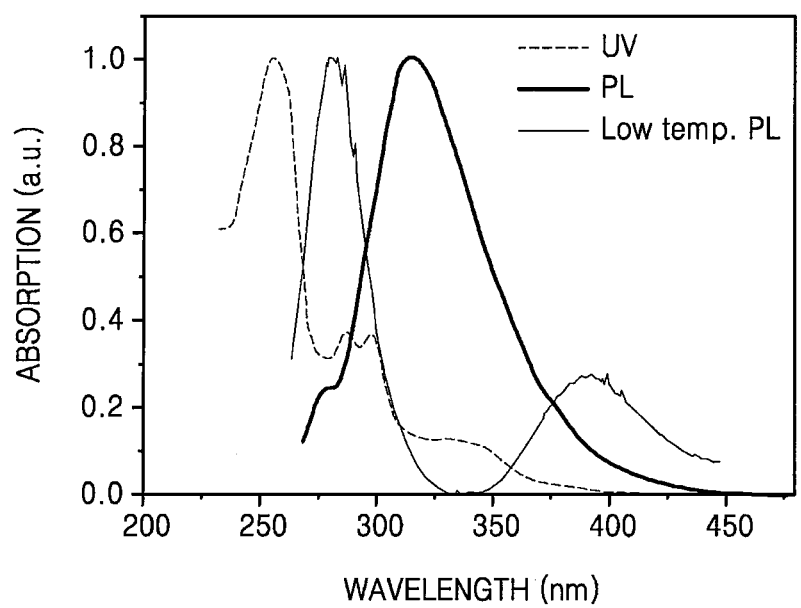
FIG. 3 is a graph showing UV absorption spectra and photoluminescence (PL) emission spectra of Compound 1.
Figure 4:
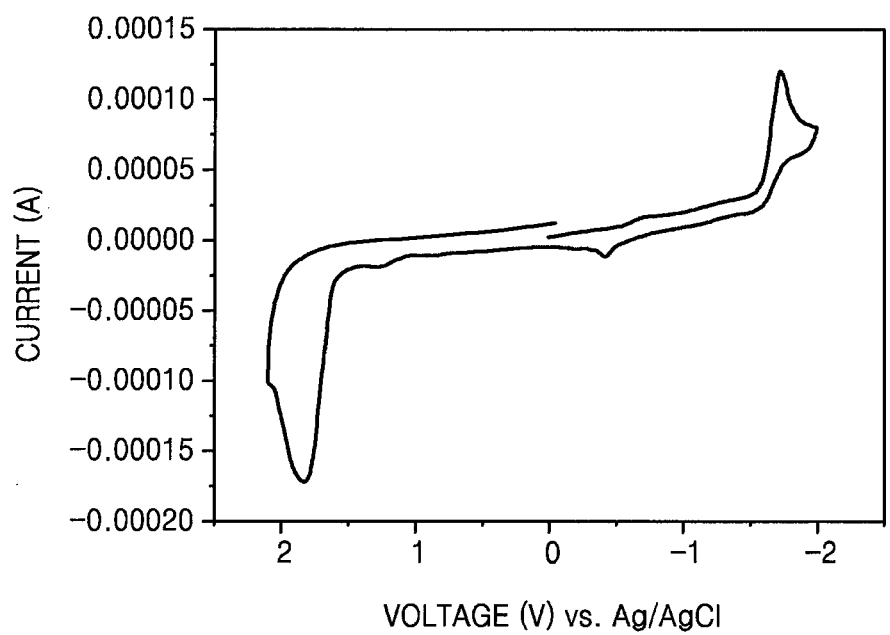
FIG. 4 is a graph showing cyclic voltammetry measurements for Compound 1.
Figure 5:
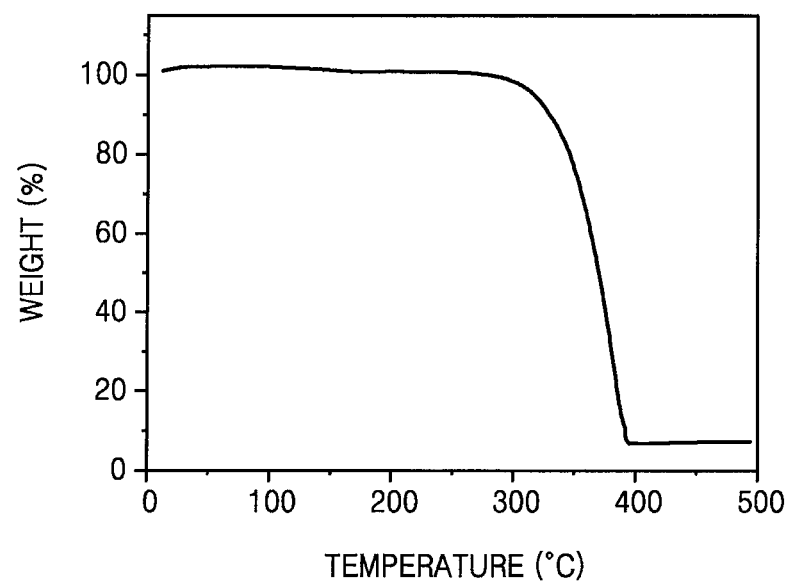
FIG. 5 is a graph showing thermogravimetric analysis (TGA) results of Compound 1.
Figure 6:
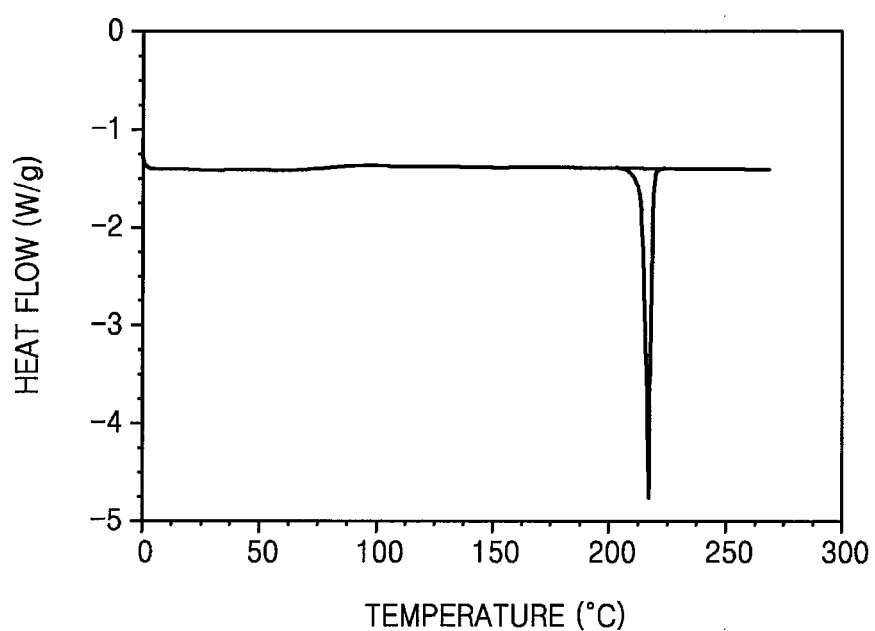
FIG. 6 is a graph showing differential scanning calorimetry (DSC) results of Compound 1.
Figure 7:
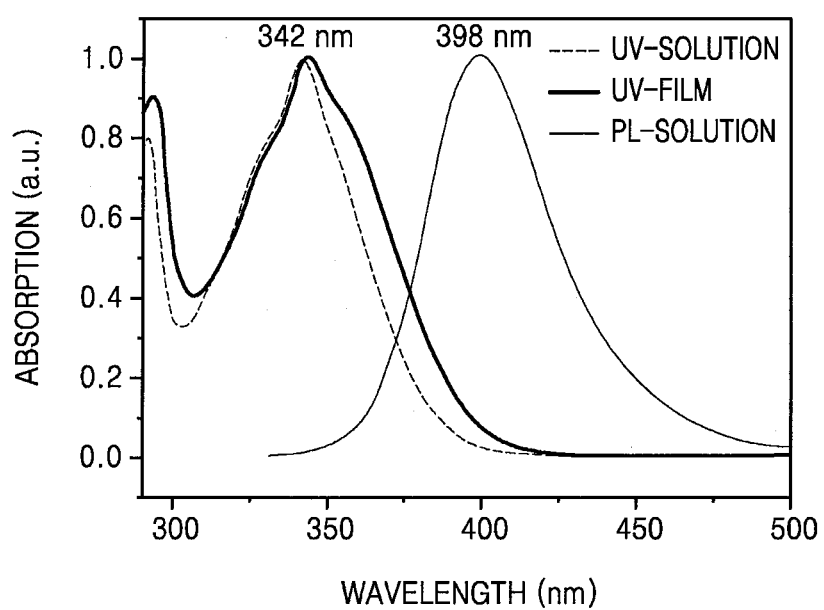
FIG. 7 is a graph showing UV absorption spectra of Compound 42 and UV absorption spectra for thin films of Compound 42.

A crystal structure of Compound 1 was obtained by way of x-ray diffraction. The crystal structure of Compound 1 is shown in FIG. 2. Additionally, UV absorption and photoluminescence emission spectra were obtained for Compound 1 and are shown in FIG. 3. FIGS. 4 to 6 show the results of cyclic voltammetry measurements, thermogravimetric analysis results, and differential scanning calorimetry results, respectively, for Compound 1. UV absorption spectra were obtained for Compound 42 and thin films of Compound 42, and are shown in FIG. 7.

As described above, according to one or more of the above example embodiments, an organic light-emitting device including an antiaromatic compound has high efficiency characteristics.

It should be understood that example embodiments described herein should be considered in a descriptive sense only and not for purposes of limitation. Descriptions of features or aspects within each example embodiment should typically be considered as available for other similar features or aspects in other example embodiments.

While one or more example embodiments have been described with reference to the figures, it will be understood by those of ordinary skill in the art that various changes in form and details may be made therein without departing from the spirit and scope as defined by the following claims, and equivalents thereof.

What is claimed is:

1. An organic light-emitting device comprising:
a first electrode;
a second electrode; and
an organic layer between the first electrode and the second electrode, and comprising an emission layer,
wherein the organic layer comprises an antiaromatic compound selected from Compounds 1 to 43 below:

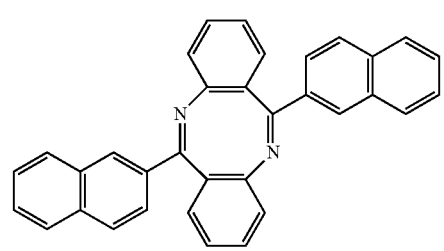

2
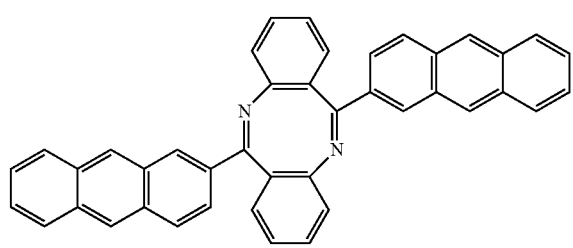
3
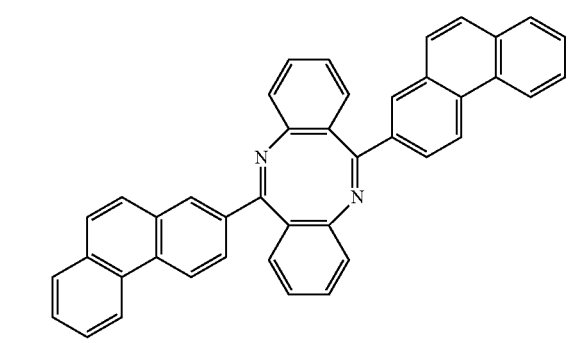
4
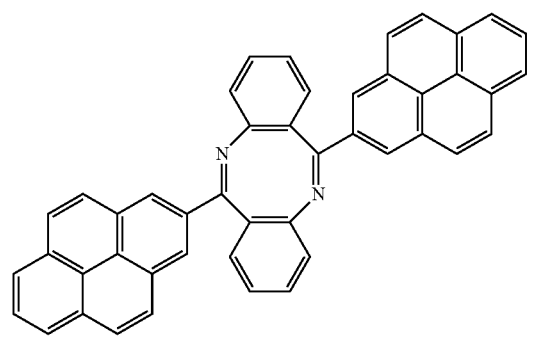
5
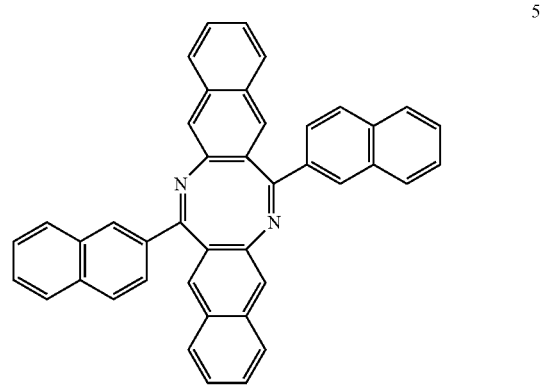
6
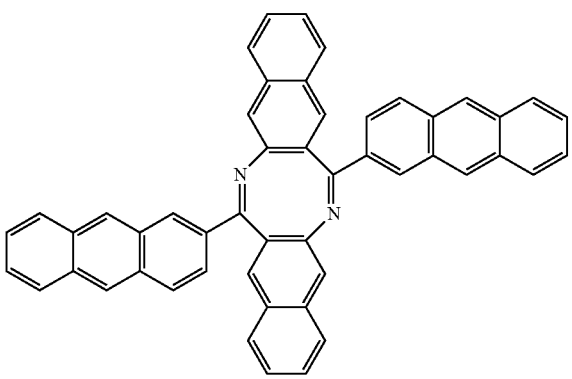
7
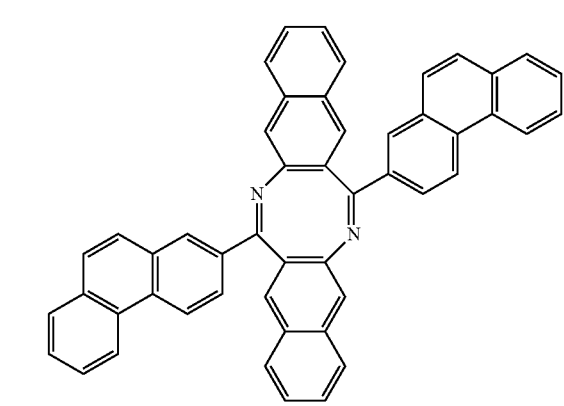
8
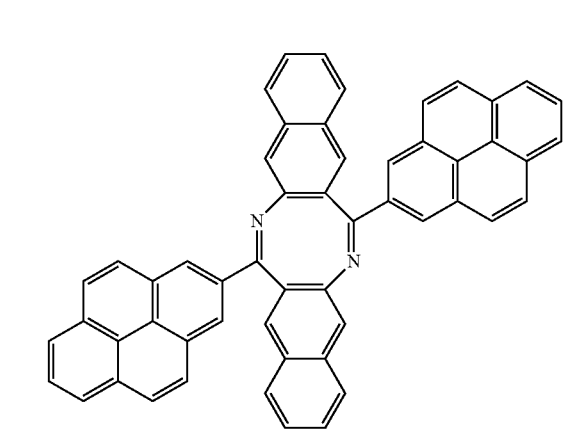
9
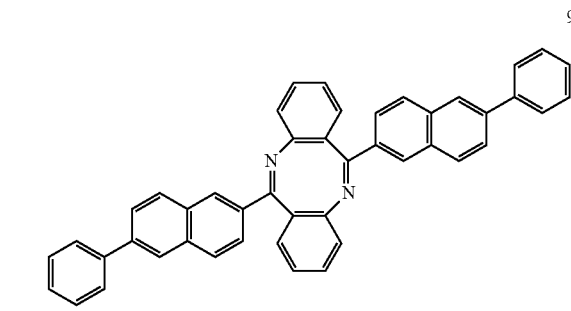

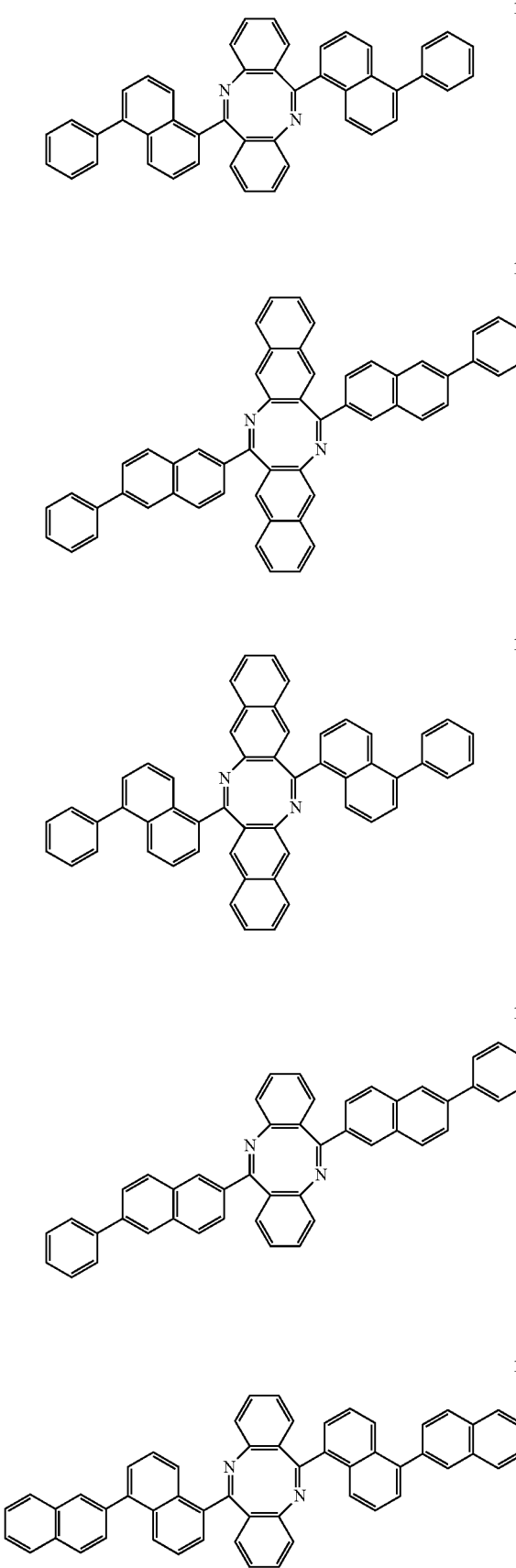
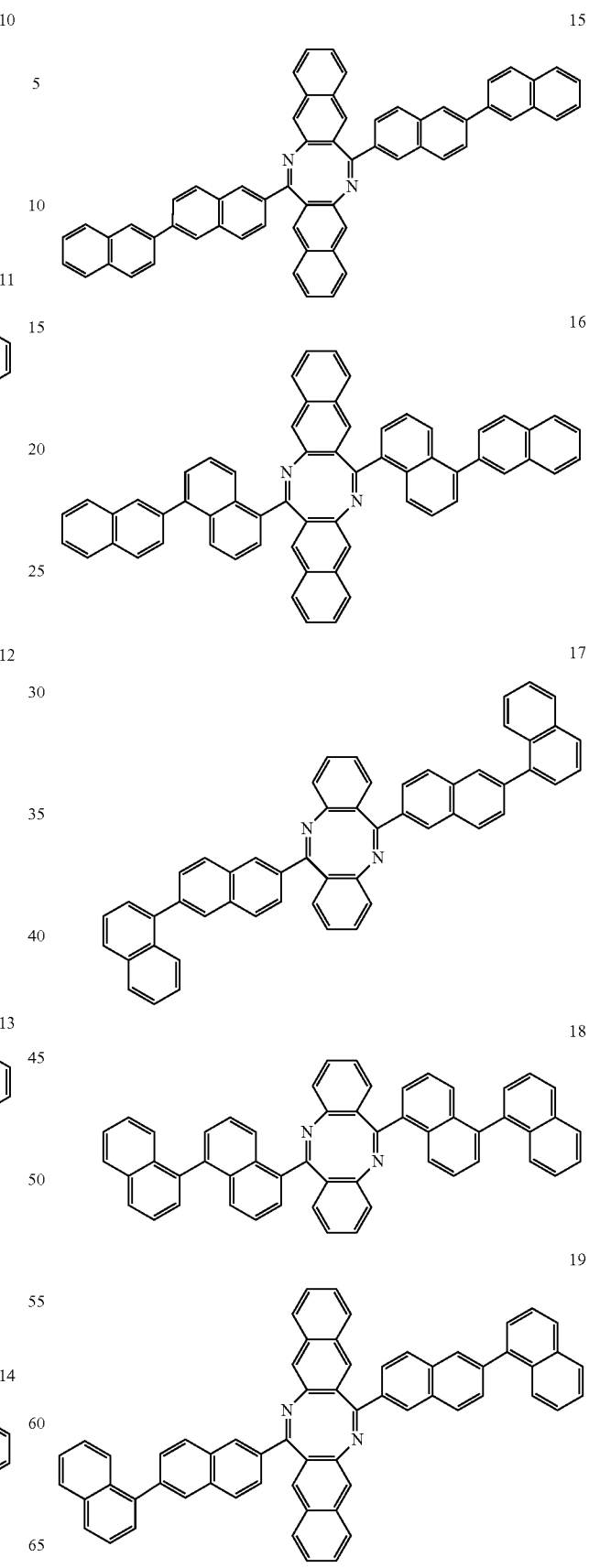

20
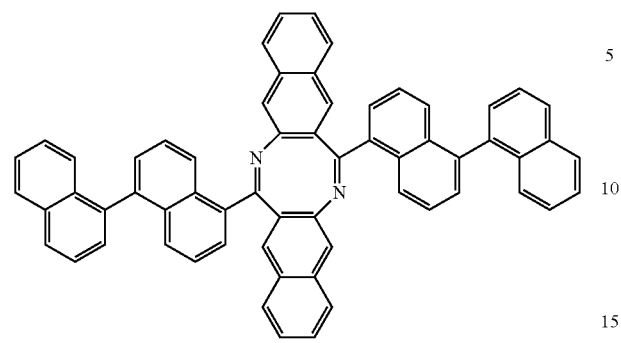
21
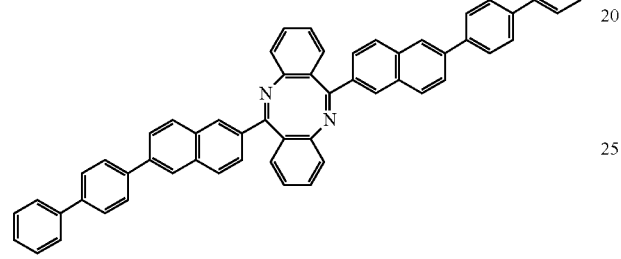
22
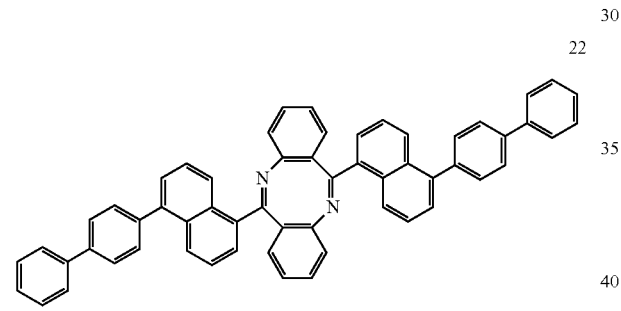
23
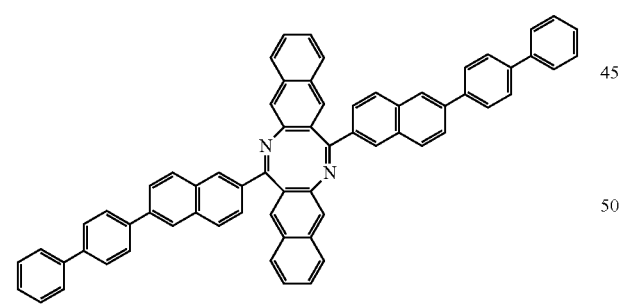
24
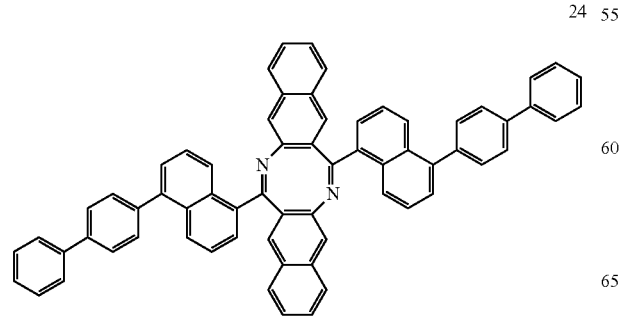
25
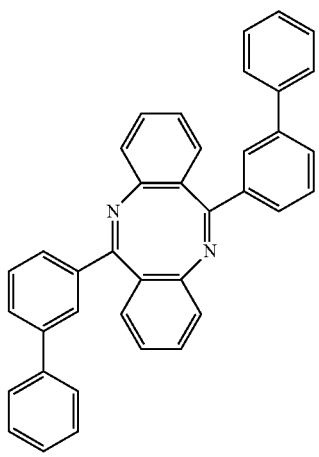
26
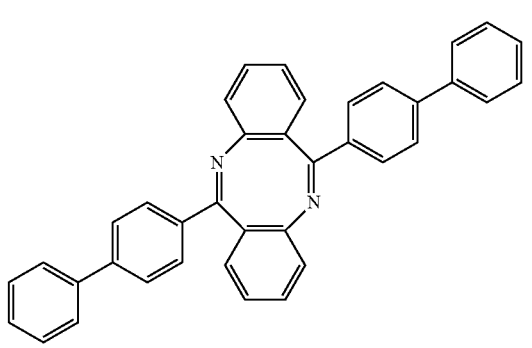
27
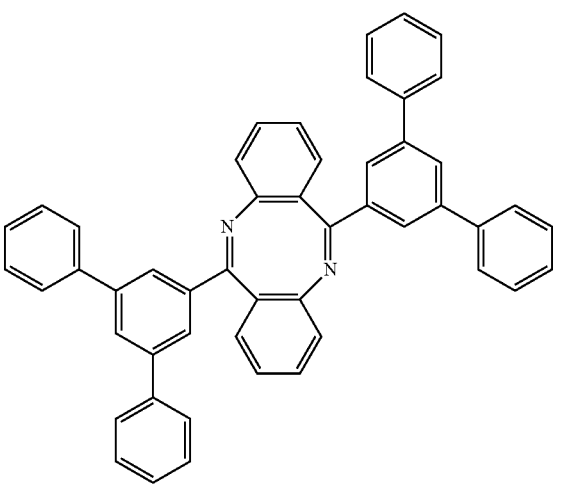

111 112
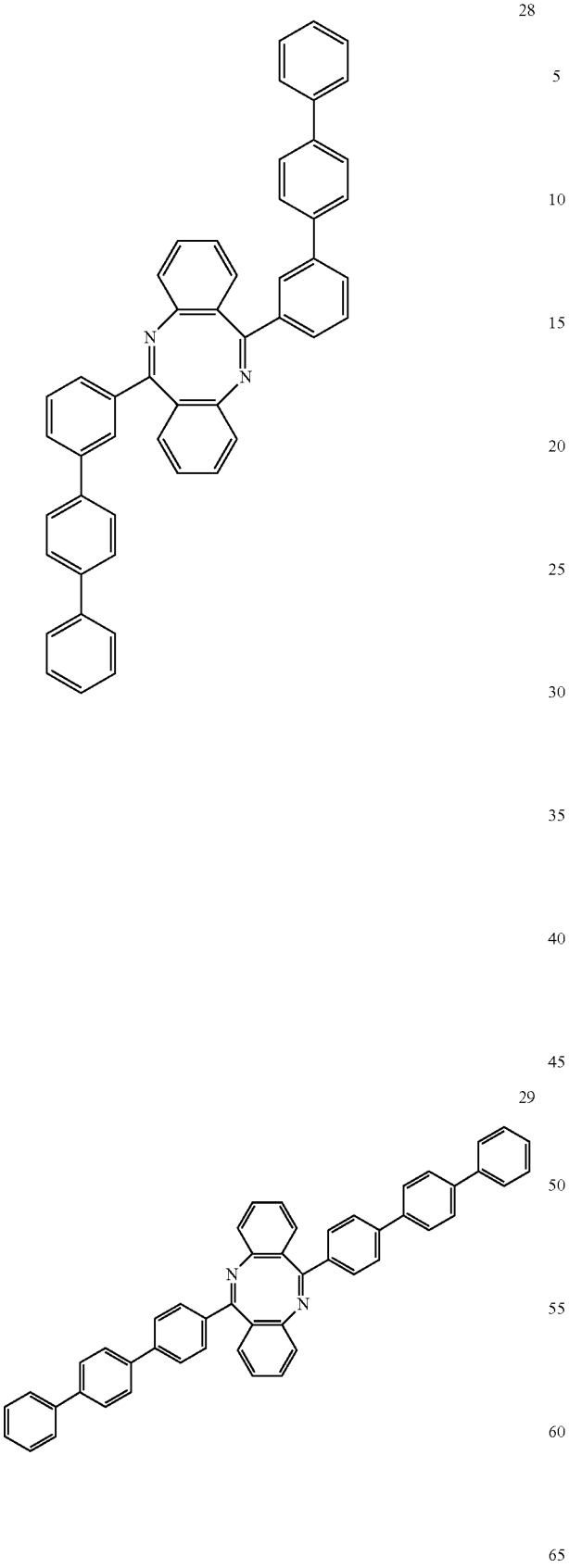
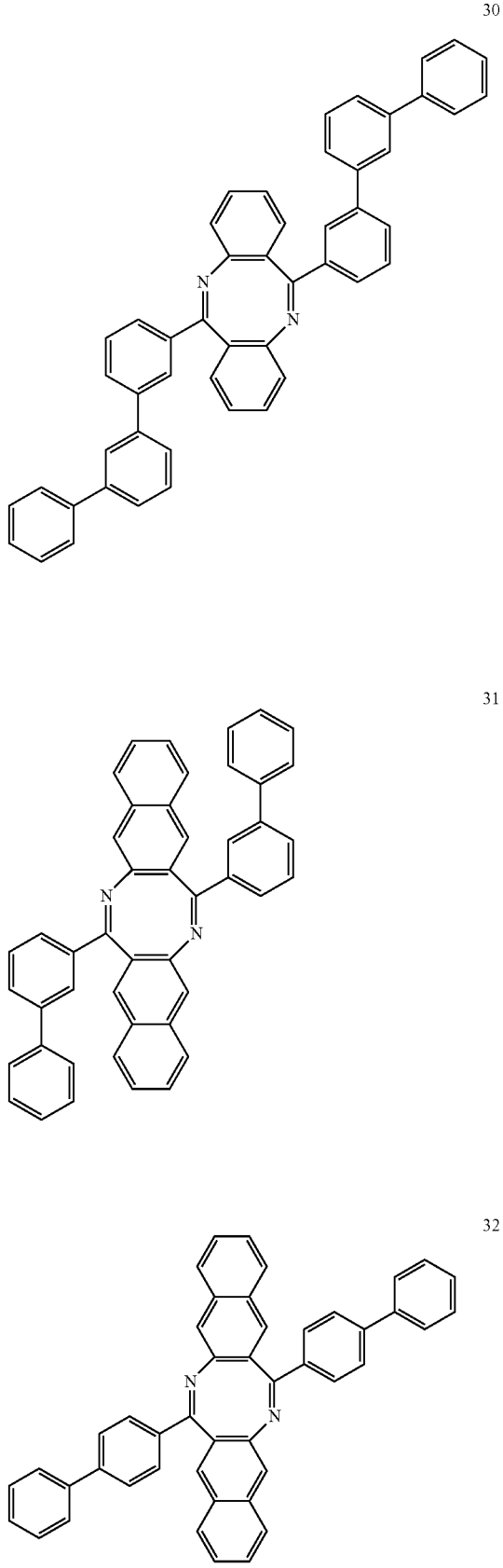

33
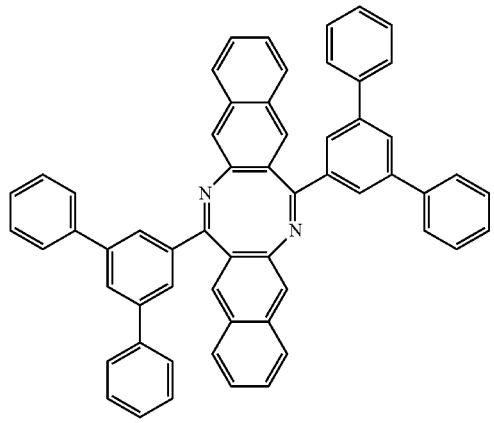
36
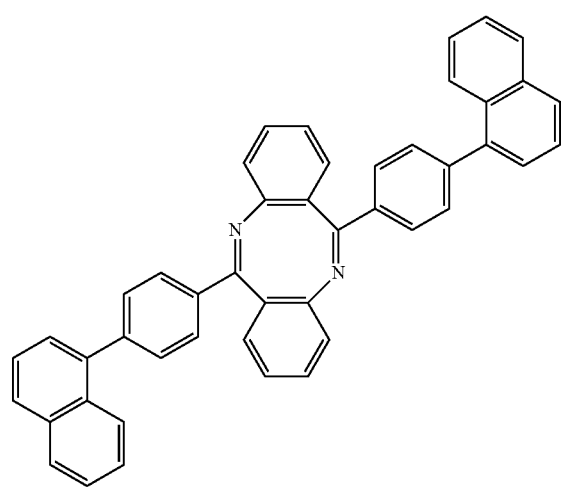
34
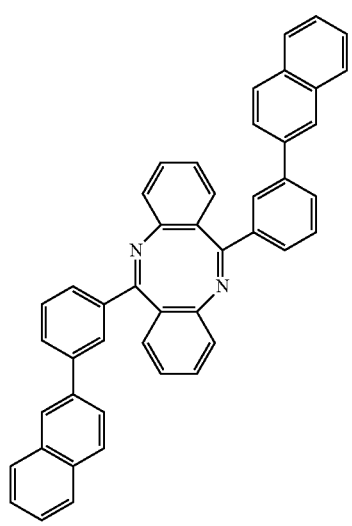
37
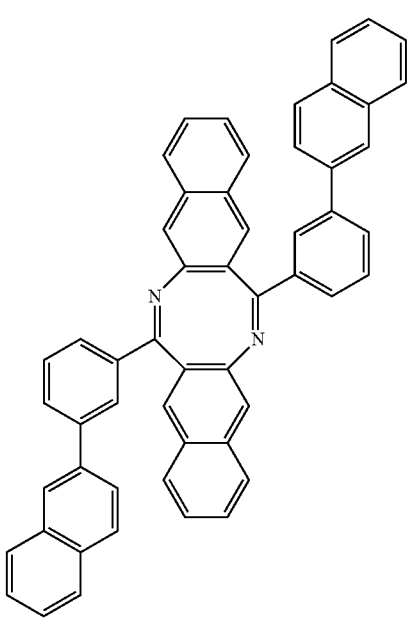
35
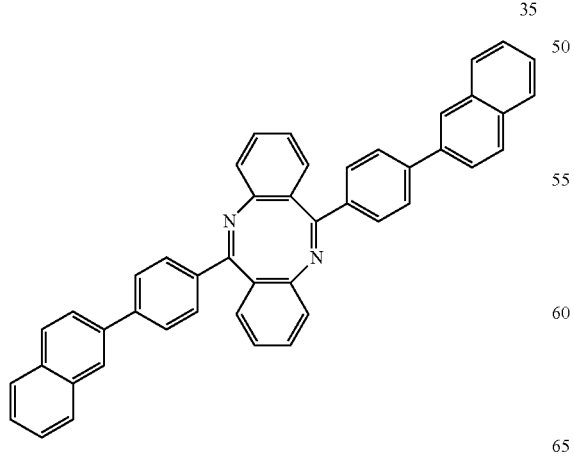
38
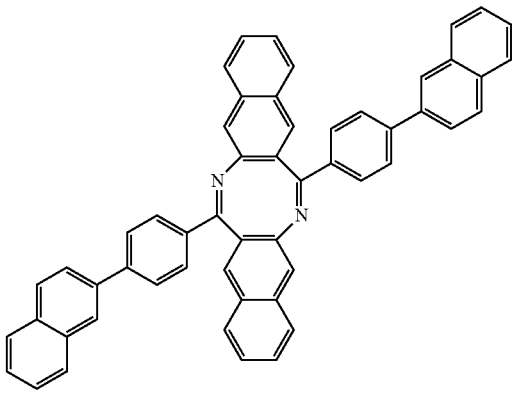

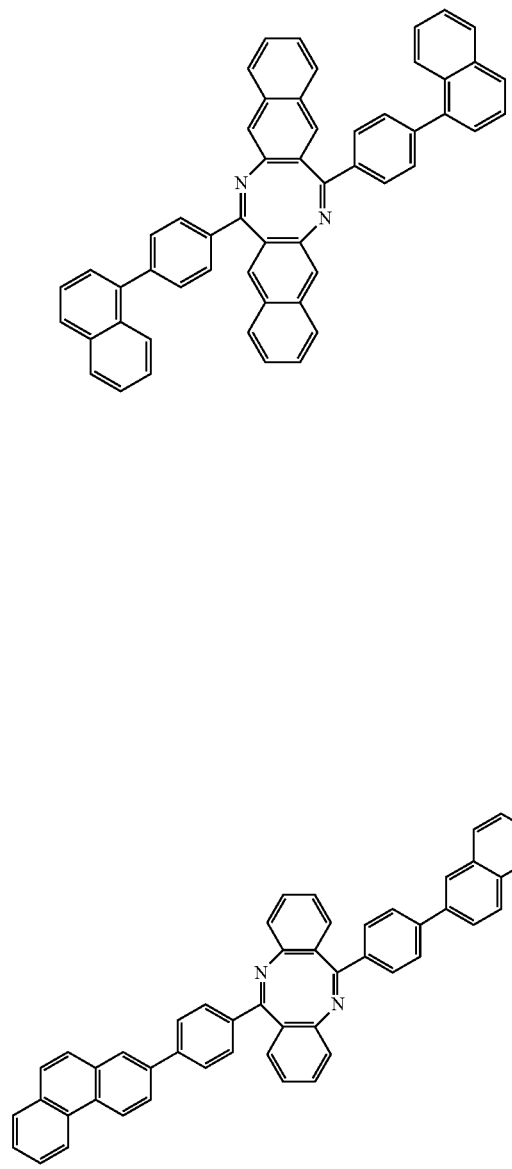
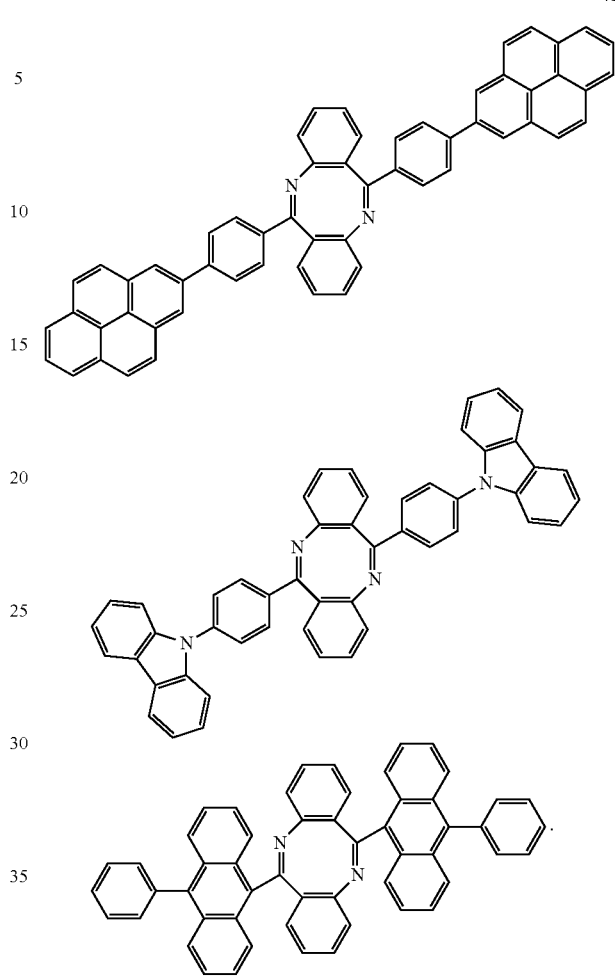
2. The organic light-emitting device of claim 1, wherein the antiaromatic compound is comprised in the emission layer.
3. The organic light-emitting device of claim 2, wherein the emission layer further comprises a dopant and the antiaromatic compound is a host.
* * * * *